US012419940B2

(12) United States Patent
Khan et al.

(10) Patent No.: US 12,419,940 B2
(45) Date of Patent: *Sep. 23, 2025

(54) COMPOSITIONS AND METHODS FOR MODIFIED DENDRIMER NANOPARTICLE DELIVERY

(71) Applicants: Massachusetts Institute of Technology, Cambridge, MA (US); Whitehead Institute for Biomedical Research, Cambridge, MA (US)

(72) Inventors: Omar F. Khan, Cambridge, MA (US); Jasdave S. Chahal, Arlington, MA (US); Daniel G. Anderson, Cambridge, MA (US); Hidde Ploegh, Brookline, MA (US); Robert S. Langer, Cambridge, MA (US); Tyler E. Jacks, Cambridge, MA (US); David A. Canner, Cambridge, MA (US)

(73) Assignees: Massachusetts Institute of Technology, Cambridge, MA (US); Whitehead Institute For Biomedical Research, Cambridge, MA (US)

( * ) Notice: Subject to any disclaimer, the term of this patent is extended or adjusted under 35 U.S.C. 154(b) by 283 days.

This patent is subject to a terminal disclaimer.

(21) Appl. No.: 17/198,037

(22) Filed: Mar. 10, 2021

(65) Prior Publication Data
US 2021/0338789 A1 Nov. 4, 2021

Related U.S. Application Data

(60) Continuation of application No. 16/692,624, filed on Nov. 22, 2019, now abandoned, which is a division of
(Continued)

(51) Int. Cl.
*A61K 9/00* (2006.01)
*A61K 9/51* (2006.01)
(Continued)

(52) U.S. Cl.
CPC ........ *A61K 39/0012* (2013.01); *A61K 9/0019* (2013.01); *A61K 9/5146* (2013.01);
(Continued)

(58) Field of Classification Search
CPC .................................................... A61K 9/0019
See application file for complete search history.

(56) References Cited

U.S. PATENT DOCUMENTS

| 5,714,166 | A | 2/1998 | Tomalia |
| 2008/0114077 | A1 | 5/2008 | Yin |

(Continued)

FOREIGN PATENT DOCUMENTS

WO 2006040579 4/2006

OTHER PUBLICATIONS

Al-Dosari, et al., "Nonviral gene delivery: principle, limitations, and recent progress", AAPS J. 11:671-81 (2009).
(Continued)

*Primary Examiner* — Paul W Dickinson
(74) *Attorney, Agent, or Firm* — Pabst Patent Group LLP

(57) ABSTRACT

Compositions and methods for modified dendrimer nanoparticle ("MDNP") delivery of therapeutic, prophylactic and/or diagnostic agent such as large repRNA molecules to the cells of a subject have been developed. MDNPs efficiently drive proliferation of antigen-specific T cells against intracellular antigen, and potentiate antigen-specific antibody responses. MDNPs can be multiplexed to deliver two or more different repRNAs to modify expression kinetics of encoded antigens and to simultaneous deliver repRNAs and mRNAs including the same UTR elements that promote expression of encoded antigens.

23 Claims, 30 Drawing Sheets

Related U.S. Application Data application No. 15/274,954, filed on Sep. 23, 2016, now Pat. No. 10,548,959.

(60) Provisional application No. 62/222,515, filed on Sep. 23, 2015.

(51) Int. Cl.

| | |
|---|---|
| *A61K 31/713* | (2006.01) |
| *A61K 39/00* | (2006.01) |
| *A61K 39/002* | (2006.01) |
| *A61K 39/12* | (2006.01) |
| *A61K 39/145* | (2006.01) |
| *A61K 48/00* | (2006.01) |
| *C12N 15/87* | (2006.01) |
| *C12N 15/88* | (2006.01) |

(52) U.S. Cl.
CPC .......... *A61K 31/713* (2013.01); *A61K 39/002* (2013.01); *A61K 39/12* (2013.01); *A61K 39/145* (2013.01); *A61K 48/00* (2013.01); *C12N 15/87* (2013.01); *C12N 15/88* (2013.01); *A61K 2039/53* (2013.01); *A61K 2039/645* (2013.01); *A61K 2039/70* (2013.01); *C12N 2740/16234* (2013.01); *C12N 2760/14134* (2013.01); *C12N 2760/16034* (2013.01); *C12N 2770/24134* (2013.01); *C12N 2770/36143* (2013.01); *Y02A 50/30* (2018.01)

(56) References Cited

U.S. PATENT DOCUMENTS

| | | |
|---|---|---|
| 2014/0255472 A1 | 9/2014 | Geall |
| 2015/0366997 A1 | 12/2015 | Guild |

OTHER PUBLICATIONS

Atkins, et al., "Therapeutic and prophylactic applications of alphavirus vectors", Expert Rev Mol Med, 10: e33 (2008).
Baum and Garcia-Sastre, "Induction of type I interferon by RNA viruses: cellular receptors and their substrates", Amino Acids, 38(5):1283-99 (2010).
Bernstein, et al., "Role for a bidentate ribonuclease in the initiation step of RNA interference", Nature, 409:363-6 (2001).
Bhadury, et al., "Identification of tumorigenic and therapeutically actionable mutations in transplantable mouse tumor cells by exome sequencing", Oncogenesis, 2(e44):1-5 (2013).
Biswas, et al., "Dendrimers for siRNA delivery", Pharmaceuticals, 6:161-83 (2013).
Bogers, et al., "Potent immune responses in rhesus macaques induced by nonviral delivery of a self-amplifying RNA vaccine expressing HIV type 1 envelope with a cationic nanoemulsion", J Infect Dis., 211(6):947-55(2015).
Brito, et al., "A cationic nanoemulsion for the delivery of next-generation RNA vaccines", Mol Ther., 22(12):2118-29 (2014).
Cho, "Design and development of degradable polyethylenimines for delivery of DNA and small interfering RNA: An updated review", ISRN Mats Sci,, 2(16):2903-24 (2012).
Cong, et al., "Multiplex genome engineering using CRISPR/Cas systems", Science, 339:819-23 (2013).
Conti, et al., "Poly(amidoamine) dendrimer nanocarriers and their aerosol formulations for siRNA delivery to the lung epithelium", Mol. Pharmaceutics, 11:1808-22 (2014).
Cullis, et al., "Interactions of liposomes and lipid-based carrier systems with blood proteins: Relation to clearance behaviour in vivo", Adv Drug Deliv Rev., 32(1-2):3-17 (1998).
Dougan, et al., "Antigen-specific B-cell receptor sensitizes B cells to infection by influenza virus", Nature 503(7476):406-409 (2013).
Elbashir, et al., "Duplexes of 21-nucleotide RNAs mediate RNA interference in cultured mammalian cells", Nature, 411:494-8 (2001b).
Elbashir, et al., "RNA interference is mediated by 21- and 22-nucleotide RNAs", Genes Dev., 15:188-200 (2001a).
Felgner, et al., "Enhanced gene delivery and mechanism studies with a novel series of cationic lipid formulations", J. Biol. Chem., 269:2550-61 (1994).
Fire, et al., "Potent and specific genetic interference by double-stranded RNA in Caenorhabditis elegans", Nature, 391:806-11 (1998).
Fuchs, et al., "First-in-Human Evaluation of the Safety and Immunogenicity of a Recombinant Vesicular Stomatitis Virus Human Immunodeficiency Virus-1 gag Vaccine (HVTN 090).", Open Forum Infect Dis., 2:1-9 (2015).
Gao, et al., "The association of autophagy with polyethylenimine-induced cytotoxicity in nephritic and hepatic cell lines", Biomaterials, 32:8613-25 (2011).
Geall, et al., "Nonviral delivery of self-amplifying RNA vaccines", PNAS, 109(36):14604-9 (2012).
Gupta, et al., "Adjuvants—a balance between toxicity and adjuvanticity", Vaccine, 11(3):293-306 (1993).
Hammond, et al., "An RNA-directed nuclease mediates post-transcriptional gene silencing in *Drosophila* cells", Nature, 404:293-6 (2000).
Hannon, "RNA interference", Nature, 418:244-51 (2002).
Heil, et al., "Species-specific recognition of single-stranded RNA via toll-like receptor 7 and 8", Science, 303(5663):1526-9 (2004).
Hekele, et al., "Rapidly produced SAM(®) vaccine against H7N9 influenza is immunogenic in mice", Emerg Microbes Infect 2(e52):1-7 (2013).
Henriksen-Lacey, et al., "Comparison of the depot effect and immunogenicity of liposomes based on dimethyldioctadecylammonium (DDA), 3ß-[N-(N',N'-Dimethylaminoethane)carbomyl] cholesterol (DC-Chol), and 1,2-Dioleoyl-3-rimethylammonium propane (DOTAP): prolonged liposome retention mediates stronger Th1 responses", Mol Pharm., 8(1):153-61 (2011).
Hoerr, et al., "In vivo application of RNA leads to induction of specific cytotoxic T lymphocytes and antibodies", Eur J Immunol, 30(1):1-7 (2000).
Hoffmann, et al., "Annual cost of illness and quality-adjusted life year losses in the United States due to 14 foodborne pathogens", J Food Prot., 75(7):1292-302 (2012).
Hofland, et al., "Formation of stable cationic lipid/DNA complexes for gene transfer", PNAS, 93(14):7305-9 (1996).
International Search report and Written Opinion for corresponding PCT application PCT/US2016/053520 mailed Jan. 4, 2017.
Jinek, et al., "A programmable dual-RNA-guided DNA endonuclease in adaptive bacterial immunity", Science, 337(6096):816-21 (2012).
Kafil, et al., "Cytotoxic impacts of linear and branched polyethylenimine nanostructures in a431 cell", BioImpacts, 1(1):23-30 (2011).
Kariko, et al., "mRNA is an endogenous ligand for Toll-like receptor 3", J Biol Chem, 279(13):12542-50 (2004).
Khan, et al., "Dendrimer-Inspired Nanomaterials for the in Vivo Delivery of siRNA to Lung Vasculature", Nano Lett 15(5):3008-16 (2015).
Khan, et al., "Ionizable amphiphilic dendrimer-based nanomaterials with alkyl-chain-substituted amines for tunable siRNA delivery to the liver endothelium in vivo", Angew Chemie, 53(52):14397-401 (2014).
Khromykh, "Replicon-based vectors of positive strand RNA viruses", Curr Opin Mol Ther, 2:555-69 (2000).
Kofler, et al.,"Mimicking live flavivirus immunization with a non-infectious RNA vaccine", PNAS, 101:1951-6 (2004).
Kreiter, et al., "Intranodal vaccination with naked antigen-encoding RNA elicits potent prophylactic and therapeutic antitumoral immunity", Cancer Res, 70(22):9031-9040 (2010).
Kreiter, et al., "Tumor vaccination using messenger RNA: prospects of a future therapy", Curr Opin Immunol, 23(3):399-406 (2011).
Kuhn, et al., "Virus nomenclature below the species level: a standardized nomenclature for laboratory animal-adapted strains and variants of viruses assigned to the family Filoviridae", Arch Virol, 158(6):1425-32 (2013).
Levin, et al., "Characterization of purified double-stranded RNA-activated elF-2 alpha kinase from rabbit reticulocytes", J Biol Chem, 256(14):7638-41 (1981).

(56) References Cited

OTHER PUBLICATIONS

Li, et al., "Characterization of cationic lipid-protamine-DNA (LPD) complexes for intravenous gene delivery", Gene Ther., 5:930-7 (1998).
Liljestrom and Garoff, "A new generation of animal cell expression vectors based on the Semliki Forest virus replicon", Biotechnology, 9(12):1356-61 (1991).
Lopez-Gordo, et al., "Circumventing antivector immunity: potential use of nonhuman adenoviral vectors", Hum Gene Ther., 25(4):285-300 (2014).
Lundstrom, "Alphavirus-based vaccines", Curr Opin Mol Ther, 4:28-34 (2002).
Lundstrom, "Alphaviruses in gene therapy", Viruses, 7(5):2321-33 (2015).
Lv, et al., "Toxicity of cationic lipids and cationic polymers in gene delivery", J. Control. Release, 114(1):100-9 (2006).
Martinez, et al., "Single-stranded antisense siRNAs guide target RNA cleavage in RNAi", Cell, 110:563-74 (2002).
McCullough, et al., "Self-Amplifying Replicon RNA Vaccine Delivery to Dendritic Cells by Synthetic Nanoparticles", Vaccines, 2:735-54 (2014b).
McCullough, et al., "Self-replicating Replicon-RNA Delivery to Dendritic Cells by Chitosan-nanoparticles for Translation In Vitro and In Vivo", Mol Ther-Nucleic Acids, 3(e173):1-17 (2014a).
Mirska, et al., "Biophysical and biochemical properties of a binary lipid mixture for DNA transfection", Colloids Surf B Biointerfaces, 40(1):51-9 (2005).
Mockey, et al., "mRNA-based cancer vaccine: prevention of B16 melanoma progression and metastasis by systemic injection of MART1 mRNA histidylated lipopolyplexes", Cancer Gene Ther., 14(9):802-14 (2007).
Napoli, et al., Introduction of a Chimeric Chalcone Synthase Gene into Petunia Results in Reversible Co-Suppression of Homologous Genes in trans., Plant Cell, 2(4):279-289 (1990).
Nykanen, et al., "ATP requirements and small interfering RNA structure in the RNA interference pathway", Cell, 107:309-21 (2001).
Partridge, et al., "Global production of seasonal and pandemic (H1N1) influenza vaccines in 2009-2010 and comparison with previous estimates and global action plan targets", Vaccine 28(30):4709-12 (2010).
Petsch, et al., "Protective efficacy of in vitro synthesized, specific mRNA vaccines against influenza A virus infection", Nat Biotechnol, 30:1210-6 (2012).
Phua, et al., "Intranasal mRNA nanoparticle vaccination induces prophylactic and therapeutic anti-tumor immunity", Sci Rep, 4(5128):1-7 (2014).
Pichlmair, et al., "RIG-I-mediated antiviral responses to single-stranded RNA bearing 5'-phosphates", Science, 314(5801):997-1001 (2006).
Pollard, et al., "Type I IFN counteracts the induction of antigen-specific immune responses by lipid-based delivery of mRNA vaccines", Mol Ther, 21(1):251-9 (2013).
Rayner, et al., "Alphavirus vectors and vaccination", Rev Med Virol., 12:279-96 (2002).
Rittig, et al., "Intradermal vaccinations with RNA coding for TAA generate CD8+ and CD4+ immune responses and induce clinical benefit in vaccinated patients", Mol Ther., 19(5):990-9 (2011).
Sahin, et al., "mRNA-based therapeutics developing a new class of drugs", Nature Rev., 13(10):759-80 (2014).
Schijns, et al., "Trends in vaccine adjuvants", Expert Rev Vaccines, 10(4):539-50 (2011).
Sledz and Williams, "RNA interference in biology and disease", Blood, 106(3):787-94 (2005).
Small, et al., "Viruses—from pathogens to vaccine carriers", Curr Opin Virol., 1(4):241-5 (2011).
Srivastava, et al., "Gene vaccines", Ann Intern Med., 138(7):550-9 (2003).
Tros de Ilarduya, et al., "Gene delivery by lipoplexes and polyplexes", Eur. J. Pharm. Sci., 40:159-70 (2010).
Ui-Tei, et al., "Sensitive assay of RNA interference in *Drosophila* and Chinese hamster cultured cells using firefly luciferase gene as target", FEBS Lett, 479(3):79-82 (2000).
Ulmer, et al., "RNA-based vaccines", Vaccine, 30(30):4414-8 (2012).
Van Lint, et al., "Preclinical evaluation of TriMix and antigen mRNA-based antitumor therapy", Cancer Res, 72:1661-71 (2012).
Van Lint, et al., "The ReNAissance of mRNA-based cancer therapy", Expert Rev Vaccines, 14(2):235-251 (2015).
Wang, et al., "Non-viral gene delivery methods", Curr Pharma Biotech., 14:46-60 (2013).
Warren, et al., "Highly efficient reprogramming to pluripotency and directed differentiation of human cells with synthetic modified mRNA", Cell Stem Cell, 7:618-30 (2010).
Weide, et al., "Direct injection of protamine-protected mRNA: results of a phase 1/2 vaccination trial in metastatic melanoma patients", J Immunother, 32(5):498-507 (2009).
Weide, et al., "Results of the first phase I/II clinical vaccination trial with direct injection of mRNA", J Immunother, 31(2):180-8 (2008).
Weiner, "RNA-based vaccination: sending a strong message", Mol Ther., 21(3):506-8 (2013).
White, et al., "Role of alpha/beta interferon in Venezuelan equine encephalitis virus pathogenesis: effect of an attenuating mutation in the 5' untranslated region", J Virol., 75(8):3706-18 (2001).
Winslow, et al., "Suppression of lung adenocarcinoma progression by Nkx2-1", Nature, 473(7345):101-4 (2011).
Xu, et al., "RNA replicon delivery via lipid-complexed PRINT protein particles", Mol Pharm., 10(9):3366-74 (2013).
Yang, et al., "Surface-engineered dendrimers in gene delivery", Chem Rev., 115:5274-5300 (2015).
Yang, et al.,"Kupfer-type immunological synapse characteristics do not predict anti-brain tumor cytolytic T-cell function in vivo", PNAS, 107:4716-21 (2010).
Ying, et al., "Cancer therapy using a self-replicating RNA vaccine", Nat Med., 5:823-7 (1999).
Zhang, et al. "Vaccines against Toxoplasma gondii: new developments and perspectives", Expert Rev Vaccines, 12(11):1287-99 (2013).
Zhang, et al., "Identification and characterization of interferon-induced proteins that inhibit alphavirus replication", J Virol, 81(20):11246-55 (2007).
Zhou, et al., "RNA melanoma vaccine: induction of antitumor immunity by human glycoprotein 100 mRNA immunization", Hum Gene Ther, 10(16):2719-24 (1999).
Zimmer, "RNA replicons-A new approach for influenza virus immunoplylaxis", Viruses, 2:413-34 (2010).
Ayatollahi, et al., "Synthesis of efficient gene delivery systems by grafting pegylated alkylcarbox chainsto PAMAM dendrimers: Evaluation of transfection efficiency and cytooxicity in cancerous and mesenchymal stem cells." Journal of Biomaterial vol. 30(5) 632-648(2015).
Sofla, et al., "Specific gene delivery mediated by poly(ethylene glycol)-grafted polyamidoamine dendrimer modified with a novel HER2-targeting nanobody" Journal of Bioactive vol. 30(2) 129-144 (2015).

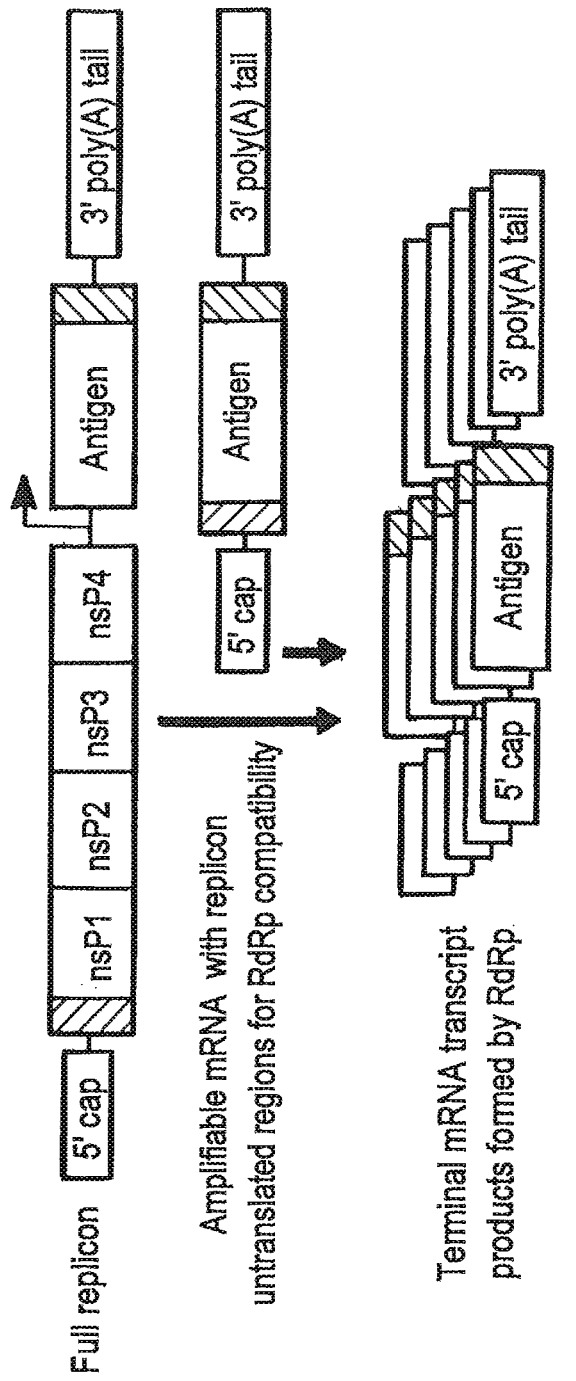

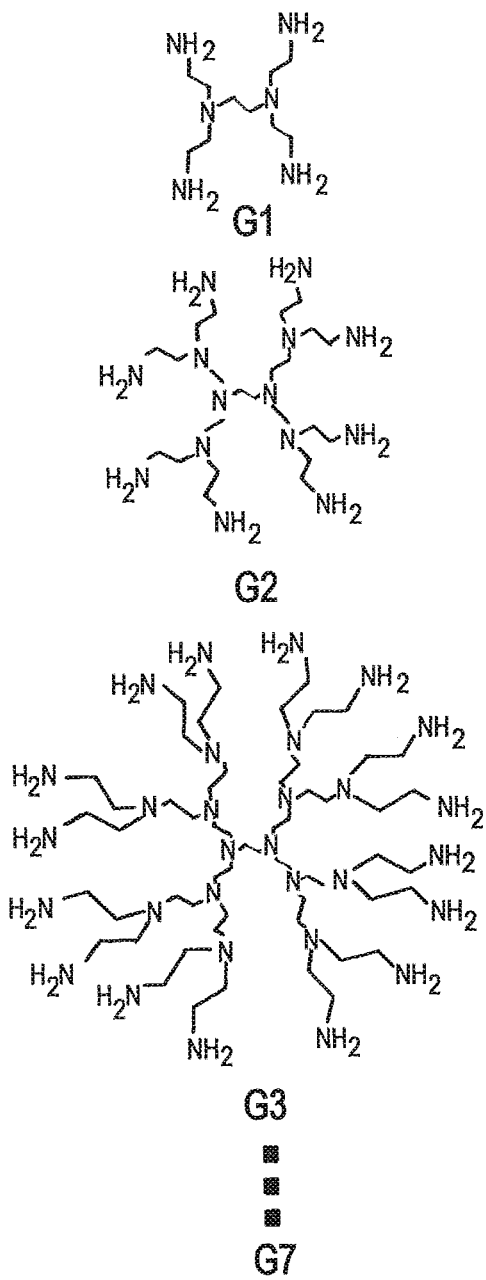
FIG. 2A/1

Poly(ethyleneimine) dendrimers, generations 1-7

G1

G2

G3

⋮

G7

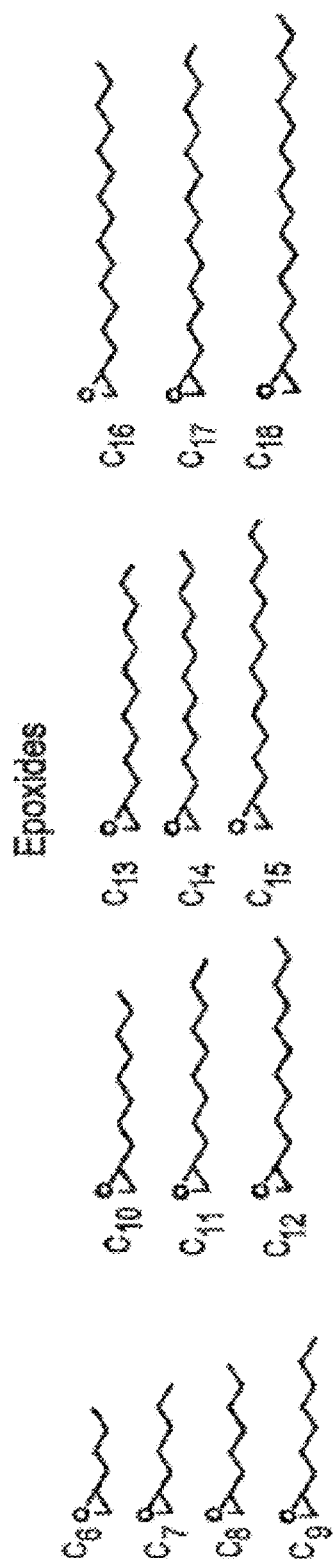

Nanoencapsulated (VEEV RepRNA)

FIG. 5D

Free RNA (SFV repRNA)

FIG. 5E

Nanoencapsulated (SFV repRNA)

1:100 Serum-Day 14 post-boost

COMPOSITIONS AND METHODS FOR MODIFIED DENDRIMER NANOPARTICLE DELIVERY

CROSS-REFERENCE TO RELATED APPLICATIONS

This application is a continuation of U.S. Ser. No. 16/692,624 filed Nov. 22, 2019, which is a divisional of U.S. Ser. No. 15/274,954 filed Sep. 23, 2016, now U.S. Pat. No. 10,548,959, issued Feb. 4, 2020, which claims priority to and the benefit of U.S. Ser. No. 62/222,515, filed on Sep. 23, 2015, which are incorporated herein in their entirety.

STATEMENT REGARDING FEDERALLY SPONSORED RESEARCH OR DEVELOPMENT

This invention was made with Government Support under Grant Nos U54 CA151884, and P30 CA01451 awarded by the National Institute of Health (NIH), and W81XWH-14-1-0100 awarded by The United States Army Medical Research and Development Command (ARMY/MRMC). The Government has certain rights in the invention.

FIELD OF THE INVENTION

The invention generally relates to the field of molecular delivery systems, and more specifically, to dendrimeric nanoparticles for the delivery of nucleic acids, antigens or small molecules to a subject to prevent or treat diseases and/or conditions.

BACKGROUND OF THE INVENTION

Vaccination remains the most effective method of preventing infectious diseases. The World Health Organization (WHO) reports that licensed vaccines are currently available to prevent or contribute to the prevention and control of twenty-five infections (World Health Organization, Global Vaccine Action Plan 2011-2020, Geneva, 2012).

However, current approaches to the delivery of peptide vaccine antigens often rely on technology that is limited in rapid production capability and associated engineering parameters to influence the type, duration, and potency of an immune response. Whilst some vaccine strategies effectively employ protein antigen, custom peptides often lack immunogenic potential and require extensive adjuvanting, and may be most useful as in vitro screening tools.

Recently, RNA has emerged as an attractive antigen vector. mRNAs have been used in mouse models to demonstrate the immunotherapeutic potential of short (<30 aa) neoantigen sequences (Bhadury, et al., Oncogenesis 2, e44, doi:10.1038/oncsis (2013). However, as a vector for immunization, pure mRNA has been investigated with varying degrees of success, particularly in the field of cancer immunotherapy. Administration of naked mRNA can confer antitumor immunity when injected directly into lymph nodes (Kreiter, et al., Cancer Res 70, 9031-9040, (2010); Van Lint, et al. Cancer Res 72, 1661-1671, (2012)). Large, replicating RNAs (repRNAs) have also been developed for delivery of vaccine antigens to cells. RepRNA translates and replicates by interacting with the ribosomal machinery of the host cell. Thus, RepRNA provides the template for increasing the number of RNA molecules translating, which in turn increases the rounds of antigen production to elicit prolonged antigen expression relative to an mRNA (McCullough, et al., *Molecular Therapy-Nucleic Acids*, 3, e173 (2014).

However, purified RNAs are notoriously unstable and are extremely vulnerable to degradation, for example, by nucleases, hydroxyl radicals, UV light, and $Mg^{2+}$-mediated inline attack. Further, the limited translocation across the cell membrane and a substantial liver clearance severely limits the potential applications for RNA-based pharmaceutical compounds such as siRNAs, mRNAs and especially large replicating RNAs. Both the translation and subsequent replication of RepRNA render it particularly sensitive to RNase, which can easily destroy ribosomal entry or gene translation. Thus, delivery of intact, functionally-viable RNA molecules to the intracellular remains a central challenge to the therapeutic application of RNA-based technologies.

Live and attenuated virus-based vaccines, such as non-infectious virions and virus-like particles (VLPs) have been developed with some degree of success. Unfortunately, current live and attenuated virus-based vaccine production methods require long production times. Fertilized egg-based methodology and newer cell bioreactor methods require lead times of months. For production, VLPs also depend on cultured cells. Gene vaccines administered in the form of virus-like particles based on adenovirus, AAV, CMV, rVSV and various alphaviruses, are of limited use due to pre-existing or induced anti-vector immunity, which precludes repeated administration.

The ability to deliver nucleic acids and proteins to mammalian cells has also been demonstrated with biomaterial-based nanoparticles, such as "Polyplexes" of cationic polymers (CPs). However, CP polyplexes and associated nucleic acids are often destabilized by salts and serum components, and can break apart or aggregate in physiological fluids (Al-Dosari, et al. *AAPS J.* 11, 671-681 (2009); Tros de Ilarduya, et al. *Eur. J. Pharm. Sci.* 40, 159-170 (2010)) and are considered inefficient as vehicles for the in vivo delivery of encapsulated agent to cells. Further, many cationic polymers exhibit cytotoxicity (Tros de Ilarduya, et al. *Eur. J. Pharm. Sci.* 40, 159-170 (2010); Gao, et al. *Biomaterials* 32, 8613-8625 (2011); Felgner, et al. *J. Biol. Chem.* 269, 2550-2561 (1994); Kafil, et al. *BioImpacts* 1, 23-30 (2011); Lv, et al. *J Contr. Rel.* 114, 100-109 (2006)).

Various nanoparticle formats have demonstrated efficacy through intradermal (Hoerr, et al., *Eur J Immunol*, 30, 1-7 (2000)), intra-splenic (Zhou, et al., *Hum Gene Ther*, 10, 2719-2724 (1999)), subcutaneous (Pollard, C. et al., *Mol Ther*, 21, 251-259 (2013)), intravenous (Hoerr, et al., *Eur J Immunol*, 30, 1-7 (2000); Mockey, et al., *Cancer Gene Ther*, 14, 802-814 (2007)) and even intranasal (Phua, et al., *Sci Rep*, 4, 5128, (2014)) routes of administration. However, few such approaches have graduated to clinical trials. While correlates of immune protection in humans have been reported, clinical efficacy has been disappointing (Weide, et al., *J Immunother*, 31, 180-188, (2008); Wcidc, et al., *J Immunother*, 32, 498-507, (2009); Rittig, et al., *Mol Ther*, 19, 990-999, (2011); Kreiter, et al., *Curr Opin Immunol*, 23, 399-406, (2011)). The administration of protamine-complexed mRNA has shown signs of success in intra-dermally immunized murine, ferret, and porcine models of influenza infection (Petsch, et al., *Nat Biotechnol*, 30, 1210-1216, (2012)).

Large RNA molecules, such as repRNA-based therapeutics, present additional problems for effective in vivo delivery. RNA molecules are susceptible to intracellular degradation when left unmodified, mRNA expression is transient, and translational repression due to inherent immunogenicity of the RNA itself (Kariko, et al., *J Biol Chem,* 279, 12542-12550, (2004); Pichlmair, et al., *Science,* 314, 997-1001, (2006); Levin, et al., *J Biol Chem,* 256, 7638-7641 (1981)), all limit efficacy. Immunogenicity and/or toxicity of the delivery compound used to deploy the vaccine is an additional complication. Cationic lipids, efficacious in some applications, (Geall, et al., *Proc Natl Acad Sci USA,* 109, 14604-14609, (2012)) are toxic when used at higher doses and if incompletely complexed (Hofland, et al., *Proc Natl Acad Sci USA,* 93, 7305-7309 (1996); Li, et al., *Gene Ther* 5, 930-937, (1998); Lv, et al., *J Control Release,* 114, 100-109, (2006). They depend on a high positive zeta potential for efficient delivery which can become a limiting factor due to neutralization in serum in vivo (Mirska, et al., *Colloids Surf B Biointerfaces,* 40, 51-59 (2005)). Furthermore, cationic lipids are immunogenic, which can limit transgene expression and raises jeopardizing safety concerns (Henriksen-Lacey, et al. *Mol Pharm,* 8, 153-161, (2011)). IFN production in response to mRNA can indeed limit efficacy of mRNA-based vaccines (Pollard, et al., *Mol Ther,* 21, 251-259 (2013)). Lipid nanoparticles created using cationic lipids also generally require additional stabilizing excipients in their formulation, raising cost and complexity of the final product.

There exists a need for improved systems for effectively delivering an encapsulated agent, such as intact genetic material, into the cells of a subject.

Therefore, it is an object of the invention to provide compositions and methods for intracellular delivery of nucleic acids, proteins and small molecules, by delivery vehicles that exert minimal or no immunogenicity and cytotoxicity.

It is a further object of the invention to provide methods and compositions for the simultaneous delivery of two or more repRNA molecules to the interior of cells.

It is a further object of the invention to provide compositions, methods, and devices for sustained expression of exogenous genes by target host cells.

It is a further object of the invention to provide methods and compositions for the delivery of therapeutic molecules into the cells of subject.

SUMMARY OF THE INVENTION

Modified dendrimer nanoparticles ("MDNPs") for the delivery of therapeutic, prophylactic and/or diagnostic agents such as nucleic acids, antigens or small molecules to a subject are provided, including large repRNA molecules, to the cells of a subject have been developed. The MDNPs efficiently drive proliferation of antigen-specific CD8+ T cells against intracellular antigen, and potentiate antibody responses against specific antigens. The nanoparticles include one or more alkylated dendrimer; one or more amphiphilic polymers such as a PEG-lipid polymers which is attached to the NPs via the hydrophobic end portion; and therapeutic, prophylactic or diagnostic agent to be delivered.

The agent to be delivered will typically be a polynucleotide, protein or peptide, or small molecule. Preferred examples include replicating RNA, most preferably a replicating RNA encoding an antigen. In some embodiments, the nanoparticles include two or more replicating RNAs which can encode the same or different antigens, which may be expressed at different rates in the cells of the subject. In some embodiments, the nanoparticles include one or more replicating RNAs and one or more messenger RNAs. One or more of the messenger RNAs can be modified to include the 5' and 3' untranslated regions of the replicating RNA.

In other embodiments, the nanoparticles include one or more RNAs capable of causing interference activity against the corresponding target gene, such as micro RNAs (miRNA); short interfering RNAs (siRNA) and double-stranded RNAs (dsRNA) that are at least 24 nucleotides in length. In some embodiments, the RNA is packaged within the nanoparticle at a molar ratio of RNA:dendrimer of about 5:1. The nanoparticles typically have a size that is between 30 nm and 450 nm, inclusive, preferably between 60 nm and 190 nm inclusive.

Typically the nanoparticles are formed of one or more alkylated dendrimers such as polypropylenimine tetramine and poly(amido amine). Exemplary akylated dendrimers include generation 1 to 7 dendrimers. In some embodiments, one or more of the dendrimers are modified by the addition of epoxide-terminated alkyl chains. The epoxide-terminated alkyl chains can range in size between 1 and 30 carbons, inclusive, preferably between 6 and 16 carbons inclusive, most preferably 6 carbons.

In some embodiments, the polymer component of the hydrophobic-anchored polymer can be polyethylene glycol (PEG), poly(propylene glycol) (PPG), and copolymers of ethylene glycol and propylene glycol, poly(saccharides), or copolymers, and mixtures thereof. In some embodiments, the polymer component of the hydrophobic-anchored polymer is polyethylene glycol with a molecular weight between 120 Da and 25,000 Da, inclusive, preferably 2,000 Da. In certain embodiments, the hydrophobic-anchored polymer is 1,2-dimyristoyl-sn-glycero-3-phosphoethanolamine-N-[methoxy (polyethylene glycol)-2000]. Typically, the mass ratio of dendrimer to polyethylene glycol of the nanoparticles is between 20:1 and 5:1, preferably 11.5:1. In some embodiments, the nanoparticles include one or more ribonucleic acid sequences that are approximately 10 to 15,000 nucleotides in length. The mass ratio of the dendrimer to ribonucleic acid can be between 10:1 and 1.5:1, preferably 5:1.

Vaccines including nanoparticles for the delivery of nucleic acids, antigens or small molecules and a pharmaceutically-acceptable excipient for administration to a subject are also provided. In some embodiments, the vaccines include nanoparticles including two or more replicating RNAs that express one or more antigens in the cells of a subject at different rates.

BRIEF DESCRIPTION OF THE DRAWINGS

FIGS. 1A-1C are schematic representations of RNA payloads. FIG. 1A shows a "full replicon" of replicating RNA, illustrating from right to left the 5' cap; 5' untranslated region; the multi-subunit RNA-dependent RNA polymerase (RdRp) including the nsP1, nsP2, nsP3 and nsP4 domains, respectively; antigen; 3' untranslated region and 3'-poly(A) tail. Multiple terminal mRNA transcript products, produced by the RdRp from the full replicon RNA are depicted below the full replicon, including from right to left, the 5' cap; antigen; 3' untranslated region and 3' poly(A)tail, respectively. FIG. 1B depicts a payload including the same "full replicon" of replicating RNA as in FIG. 1A, as well as a messenger RNA (mRNA) construct including the same untranslated region as the RdRp encoded by the replicating mRNA. Multiple terminal mRNA transcript products produced by the RdRp from both the full replicon and also the mRNA construct are depicted below the full replicon, including from right to left, the 5' cap; antigen; 3' untranslated region and 3' poly(A)tail, respectively. FIG. 1C is a schematic that depicts the relative sizes of siRNA, mRNA and replicon RNA, respectively.

FIG. 2A the molecular structures of generations 1-3 (G1-G3) of PEI dendrimers, generations 1-4 (G1-G4) of DAB-Am 4 dendrimers and generations 0-3 (G0-G3) of PAMAM dendrimers, as well as the molecular structures of epoxides ranging in size from C6-C18 that can be used to formulate ionizable dendrimer-based nanomaterials. FIG. 2B is a cartoon depicting the three components including an RNA encapsulated agent (ionizable dendrimers, lipid-anchored PEG, and RNA). FIG. 2C is a drawing of the modified dendrimer-based nanoparticle (10) formulated as depicted in FIG. 2B to include dendrimeric material in a lamellar form (12), amphiphilic polymer (14), including hydrophobic (16) and hydrophilic (18) components, and encapsulated RNA (20).

FIGS. 5A-5G are graphs showing Count (cells) over CFSE for Free mRNA (FIG. 5A) and Nanoencapsulated mRNA (FIG. 5B); Free VEE repRNA (FIG. 5C) and Nanoencapsulated VEE repRNA (FIG. 5D); and Free SFV repRNA (FIG. 5E) and Nanoencapsulated SFV repRNA (FIG. 5F). FIG. 5G shows CFSE over cell count for both Negative and Positive controls. Detectable protein expression is indicated in each panel by a cross (no expression-see negative control in FIG. 5G) and a tick for expression (see Positive control in FIG. 5G), respectively.

FIG. 6G shows CFSE over cell count for an unimmunized control. Detectable protein expression is indicated in each FIGS. 6A-6G by a cross for no expression (see negative control in FIG. 6G) and a tick for expression (see FIG. 6D).

FIG. 10B is a schematic representation of a modified dendrimer-based nanoparticle (50) including dendrimeric material in a lamellar form (52), amphiphilic polymer (54), and containing multiple nucleic acid payloads, including three nanoencapsulated repRNAs (56), (58), (60), each encoding a different antigen (Antigen A-C), and a mRNA construct (62), encoding a fourth antigen (Antigen D), where the 5' untranslated sequence of the nanoencapsulated repRNA (64) is the same as that of the mRNA. (66).

FIG. 11A is a graph showing cell count (normalized to mode, 0-100) over HA protein counts for each of untransfected and VEE HA transfected samples, respectively. FIG. 11D is a line graph showing % survival over time post H1N1 infection (Days) for vaccinated ( - - - ) and unvaccinated ( . . . ) mice, respectively.

FIG. 12A is a line graph showing OD for EBOV GP IgG in serum diluted 1/100 at day 14 post-boost for each samples containing of adjuvant (●), GP (■), GP/VP40 (▲) and Adjuvant/GP/VP40 (▼), respectively.

DETAILED DESCRIPTION OF THE INVENTION

I. Definitions

Figure 1A:
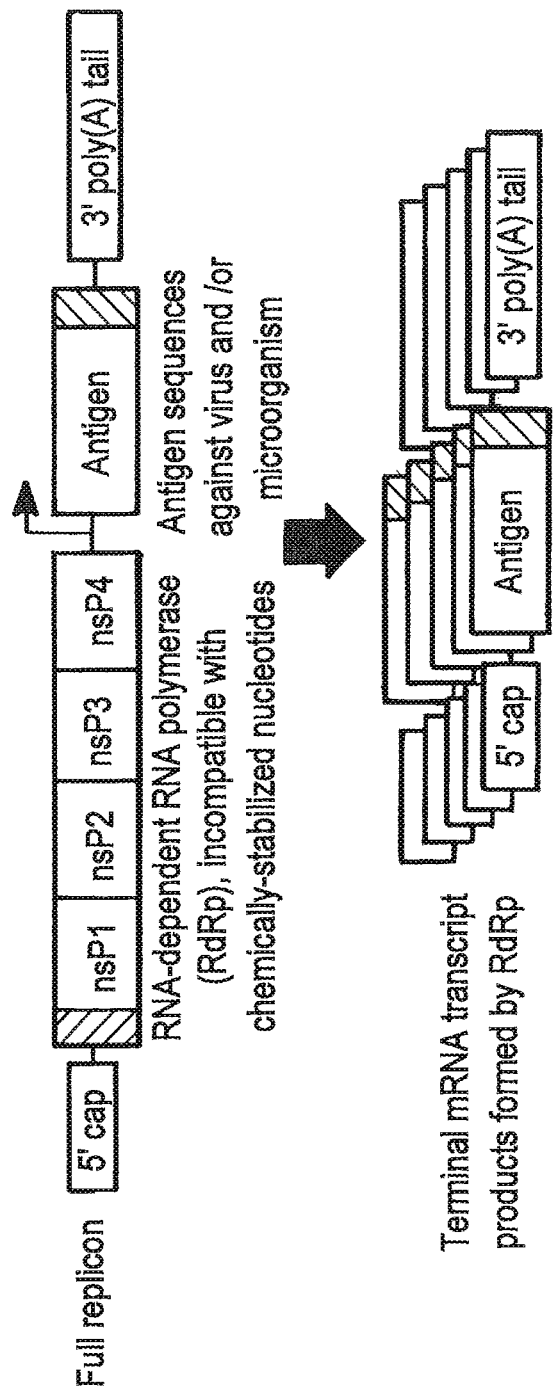

The term "host cell" refers to prokaryotic and eukaryotic cells into which a recombinant expression vector can be introduced.

The terms "hydrophobic-anchored polymers", amphiphilic polymer and "lipidic polymer" are used interchangeably to refer to a polymer that is covalently bound to one or more aliphatic groups.

The term "dendrimer" is intended to include, but is not limited to, a molecular architecture with an interior core and layers (or "generations") of repeating units which are attached to and extend from this interior core, each layer having one or more branching points, and an exterior surface of terminal groups attached to the outermost generation. Dendrimers have regular dendrimeric or "starburst" molecular structures.

The term "Alkyl" refers to saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., C1-C30 for straight chain, C3-C30 for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The alkyl groups can also be substituted with one or more groups including, but not limited to, halogen, hydroxy, amino, thio, ether, ester, carboxy, oxo, and aldehyde groups. The alkyl groups may also contain one or more heteroatoms. "Lower alkyl", means 1-6 carbons, preferably 1-5 carbons, more preferably 1-4 carbons, most preferably 1-3 carbons.

The terms "amine" and "amino" are art-recognized and refer to both unsubstituted and substituted amines, e.g., a moiety that can be represented by the general formula:

$$-N\begin{matrix}R_{10}\\ \\R_9\end{matrix} \quad \text{or} \quad -\overset{R'_{10}}{\underset{R_9}{N}}-R_{10}$$

wherein, $R_9$, $R_{10}$, and $R'_{10}$ each independently represent a hydrogen, an alkyl, an alkenyl, $-(CH_2)_m-R_8$ or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In still more preferred embodiments, the term "amine" does not encompass amides, e.g., wherein one of $R_9$ and $R_{10}$ represents a carbonyl. In even more preferred embodiments, $R_9$ and $R_{10}$ (and optionally $R'_{10}$) each independently represent a hydrogen, an alkyl or cycloalkyl, an alkenyl or cycloalkenyl, or alkynyl. Thus, the term "alkylamine" refers to an amine group, as defined above, having a substituted (as described above for alkyl) or unsubstituted alkyl attached thereto, i.e., at least one of $R_9$ and $R_{10}$ is an alkyl group.

The term "amide" is art-recognized as an amino-substituted carbonyl and includes a moiety that can be represented by the general formula:

$$\underset{R_{10}}{\overset{O}{\underset{\|}{\underset{}{\overset{}{\text{-}}}}}}\underset{}{\overset{}{\underset{N}{\overset{}{\text{-}}}}}R_9$$

wherein, $R_9$ and $R_{10}$ are as defined above.

The term "nanomaterial" refers to a material having at least one dimension which is between approximately one nanometer and one micron.

The term "dendrimer-based nanoparticle", or "MDNP" refers to a nanoscale particle, delivery vehicle, including an outer surface including dendrimers and hydrophobic-anchored polymers, and typically a payload molecule. Typically, the payload molecules are enclosed within the particle.

The terms "transformed" and "transfected" encompass the introduction of a nucleic acid (e.g., a vector) into a cell by a number of techniques known in the art.

The term "specifically binds" to a target refers to a binding reaction which is determinative of the presence of the molecule in the presence of a heterogeneous population of other biologics.

"Localization Signal" or "Localization Sequence" or "Recognition Sequence" or "Targeting Signal" or "Recognition Sequence" or "Recognition Tag" or "Recognition polynucleotide" are used interchangeably and refer to a signal that directs a molecule to a specific cell, tissue, organelle, or intracellular region. The signal can be polynucleotide, polypeptide, or carbohydrate moiety or can be an organic or inorganic compound sufficient to direct an attached molecule to a desired location.

The term "vector" refers to a nucleic acid molecule or 'polynucleotide, such as a replicating RNA, plasmid, phage, or cosmid, into which another nucleic acid sequence segment may be inserted so as to bring about the replication of the inserted segment. The described vectors can be expression vectors.

The terms "replicating RNA", "repRNA", "replicon mRNA", "mRNA replicon," and "replicon RNA" are used interchangeably and refer to a replication-competent, progeny-defective RNA virus genome that is incapable of producing infectious progeny virions. Viral genomes that are typically modified for use as repRNAs include 'positive strand' RNA viruses. These modified viral genomes function as both mRNA and templates for replication.

The term "expression vector" refers to a vector that includes one or more expression control sequences.

The term "nucleic acid" refers to any natural or synthetic linear and sequential arrays of nucleotides and nucleosides, for example, DNA including complementary DNA (cDNA), replicating RNA (repRNA), messenger RNA (mRNA), small interfering RNA (siRNA), transfer RNA (tRNA), microRNA (miRNA), guide strand RNA (sgRNA), polynucleotides, oligo-nucleotides, oligo-nucleosides and derivatives thereof. Such nucleic acids may be collectively referred to as "constructs," or "plasmids. Representative examples of the nucleic acids include bacterial plasmid vectors including expression, cloning, cosmid and transformation vectors such as, but not limited to, viral vectors, vectors derived from bacteriophage nucleic acid, and synthetic oligonucleotides like chemically synthesized DNA or RNA. The term "nucleic acid" further includes modified or derivatized nucleotides and nucleosides such as, but not limited to, halogenated nucleotides such as, but not only, 5-bromouracil, and derivatized nucleotides such as biotin-labeled nucleotides.

The term "gene" or "genes" refers to isolated or modified nucleic acid sequences, including both RNA and DNA, that encode genetic information for the synthesis of a whole RNA, a whole protein, or any portion of such whole RNA or whole protein. Genes that are not naturally part of a particular organism's genome are referred to as "foreign genes", "heterologous genes" or "exogenous genes" and genes that are naturally a part of a particular organism's genome are referred to as "endogenous genes". The term "gene" as used with reference to genomic DNA includes intervening, non-coding regions as well as regulatory regions and can include 5' and 3' ends.

The term "expressed" or "expression" refers to the transcription from DNA to an RNA nucleic acid molecule at least complementary in part to a region of one of the two nucleic acid strands of the gene. The term "expressed" or "expression" also refers to the translation from said RNA nucleic acid molecule to give a protein or polypeptide or a portion thereof.

The term "antigen" refers to any substance (e.g., peptide, protein, nuclei acid, lipid, small molecule, such as a moiety expressed by or otherwise associated with a pathogen or cancerous or pre-cancerous cell) that serves as a target for the receptors of an adaptive immune response. The antigen may be a structural component of a pathogen, cancerous or pre-cancerous cell.

The term "pathogen" refers to an organism or other entity that causes a disease. For example, pathogens can be prions, viruses, prokaryotes such as bacteria, eukaryotes such as protozoa and fungi. A pathogen can be the source of an antigen to which an adaptive immune response can be generated.

The term "polypeptide" includes proteins and fragments thereof. Polypeptides are described as amino acid residue sequences. Those sequences are written left to right in the direction from the amino (N) to the carboxyl (C) terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "antibody" is used in the broadest sense unless clearly indicated otherwise. Therefore, an "antibody" can be naturally occurring or man-made, such as monoclonal antibodies produced by conventional hybridoma technology. Antibodies include monoclonal and polyclonal antibodies as well as fragments containing the antigen-binding domain and/or one or more complementarity determining regions of these antibodies. "Antibody" refers to any form of antibody or antigen binding fragment thereof and includes monoclonal antibodies (including full length monoclonal antibodies), polyclonal antibodies, multi-specific antibodies (e.g., bi-specific antibodies), and antibody fragments.

The terms "individual," "individual," "subject," and "patient" are used interchangeably, and refer to a mammal, including, but not limited to, humans, rodents, such as mice and rats, and other laboratory animals.

The term "biocompatible" refers to one or more materials that are neither themselves toxic to the host (e.g., an animal or human), nor degrade (if the polymer degrades) at a rate that produces monomeric or oligomeric subunits or other byproducts at toxic concentrations in the host.

The term "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

II. Compositions for Delivery of Proteins, Small Molecules and Nucleic Acids to the Interior of Cells Compositions for the enhanced delivery of therapeutic, prophylactic and diagnostic agents to the cells of a subject have been developed. The efficacy of delivery of molecules, such as nucleic acids, to the interior of cells is strongly correlated with overcoming barriers such as uptake by antigen-presenting cells, phagosomal/lysosomal escape, nucleic acid un-packaging, intracellular translocation, etc. In the case of genetic material, sustained gene expression is also a consideration. To effectively persist in the blood stream and enable uptake by a target cell, the delivery vehicles must exhibit minimal immunogenicity. To be clinically relevant, delivery vehicles must exert minimal cytotoxicity.

Compositions include therapeutic, prophylactic and diagnostic agents enclosed or encapsulated within non-toxic, non-immunogenic, biodegradable nanoparticles and have a size amenable for uptake by eukaryotic cells in vivo for the efficient delivery of the therapeutic, prophylactic and diagnostic agents to the intracellular space. The delivery vehicles can protect therapeutic, prophylactic and diagnostic agents from immune surveillance and degradation in the body and enhance the serum half-life of the encapsulated active-agents. The delivery vehicles can optionally include one or more targeting motifs to enhance specificity and uptake by target cells.

A. Modified Dendrimer-Based Nanoparticle (MDNPs)

MDNPs are useful delivery vehicle for a broad range of molecules to the interior of cells. MDNPs are synthetic, multi-component structures that self-assemble into 100 nm-scale particles with lipidoid-like morphology. The MDNPs are spherical lamellar structures that encapsulate one or more nucleic acids, such as large replicating RNAs, mRNAs, proteins and small molecules. Compositions for the intracellular delivery of therapeutic, prophylactic and diagnostic agents which employ MDNPs as vessels containing nucleic acids, protein and small-molecules are described for a range of applications, including vaccine reagents, therapeutics, as well as tools for basic research.

MDNPs are formulated from dendrimers that are ionizable and positively charged at low pH; one or more amphiphilic polymers; and one or more therapeutic, prophylactic and/or diagnostic agents for delivery to the cells of a subject. Typically, MDNPs are non-toxic, non-immunogenic, and typically have a size amenable for uptake by eukaryotic cells. In some embodiments, the MDNPs are sized to prevent or enhance uptake by a particular cell type or group of cell types. For example, MDNPs can be engineered to enhance or prevent uptake by antigen-presenting cells, such as macrophages. An exemplary size for a single modified dendrimer-based nanoparticle is in the range of 30 nm to 1,000 nm in the longest dimension, for example, MDNPs can have an average size from 30 nm to 450 nm, inclusive, for example, from 50 nm to 300 nm, inclusive, more preferably 60 nm to 250 nm, inclusive. Nanoparticle size can be influenced by the length of the alkyl chain that substitutes the core dendrimer. It can also be influenced by the amount of amphiphilic polymer and the size of the encapsulated agent.

1. Ionizable Dendrimer-Based Nanomaterial

Typically, the dendrimers are ionizable and positively charged at low pH values. The dendrimers are typically constructed of iterative layers, or generations, derived from a defined core structure having a specific number of reactive groups, onto which successive generations are attached. The dendrimers can be zero to seven generations. Higher generations of dendrimers have significantly decreased solubility. The structural diversity of dendrimers, the number of generations and the range of potential lipid modifications offer extraordinary combinatorial potential toward the development of drug delivery systems. Typically, dendrimer-based nanomaterials are formulated with epoxide-terminated molecules.

Each successive dendrimer generation can be covalently bound to the previous generation. The number of reactive groups of the core structure determines n-directionality and defines the number of structures that can be attached to form the next generation.

The number of branches in a dendritic structure is dependent on the branching valency of the monomeric building blocks, including the core. For example, if the core is a primary amine, the amine nitrogen would then be divalent, resulting in a 1→2 branching motif.

The dendrimers are preferably alkylated dendrimers, referred to herein as "alkylated dendrimers". Exemplary dendrimeric materials include, but are not limited to, Poly (amido-amine) (PAMAM), Poly (ethyleneimine) (PEI), polyester, polylysine, Polypropyleneimine (PPI), Diaminobutane amine polypropylenimine tetramine (DAB-Am 4), Polypropylamine (POPAM), polylysine, polyester, iptycene, aliphatic poly(ether), and/or aromatic polyether dendrimers.

The dendrimers can have carboxylic, amine and hydroxyl terminations and can be of any generation including, but not limited to, generation 1 dendrimers (G1), generation 2 dendrimers (G2), generation 3 dendrimers (G3), generation 4 dendrimers (G4), generation 5 dendrimers (G5), generation 6 dendrimers (G6), generation 7 dendrimers (G7), generation 8 dendrimers (G8), generation 9 dendrimers (G9), or generation 10 dendrimers (G10). MDNPs can also be formed from generations of dendrimers greater than 10.

The PAMAM class of dendrimers contains internal amide bonds which may enhance their biodegradability, thus improving tolerance in terms of human therapeutic applications. The amino surface includes polar, highly reactive primary amine surface groups. The surfaces of the amino-functional PAMAM dendrimers are cationic and can be derivatized, either through ionic interactions with negatively charged molecules, or using many well-known reagents for covalent functionalization of primary amines.

FORMULA I: Molecular structure of a generation 0(G0) Poly(amido-amine) (PAMAM).

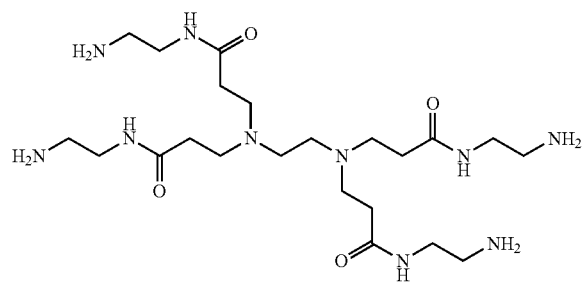

When MDNPs are formed from PAMAM dendrimers, generations from 0 to 7 PAMAM dendrimers are typically used. For example, MDNPs can be formed from generation 0 PAMAM dendrimers (G0); generation 1 (G1) PAMAM dendrimers; generation 2 (G2) PAMAM dendrimers; generation 3 (G3) PAMAM dendrimers; generation 4 (G4) PAMAM dendrimers; generation 5 (G5) PAMAM dendrimers; generation 6 (G6) PAMAM dendrimers; or generation 7 (G7) PAMAM dendrimers. An exemplary scheme showing the structures of successively increasing generations (G0-G3) of PAMAM dendrimers is depicted in Scheme I, below.

PAMAM is commercially available from multiple sources, including Sigma-Aldrich (Cat. No. 597309).

Figure 2A:
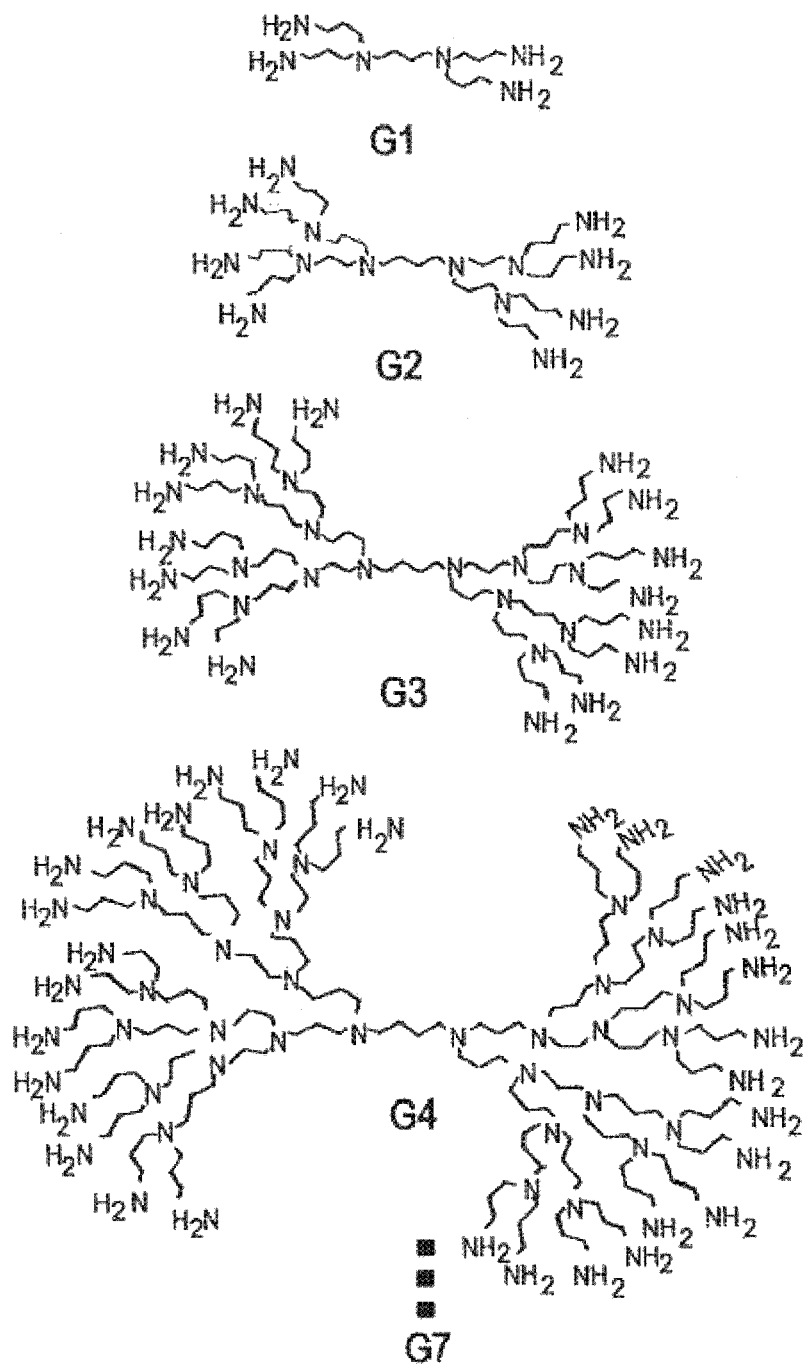
FIGS. 2A-2C are schematic representations showing the three-component system for delivery of intracellular cargo.
Figure 2A:
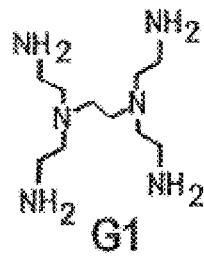
Figure 2A:
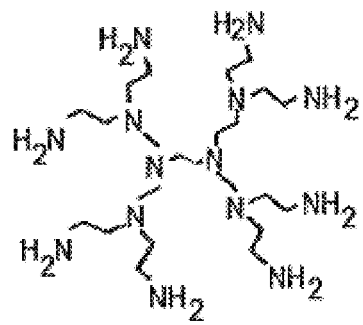
Figure 2A:
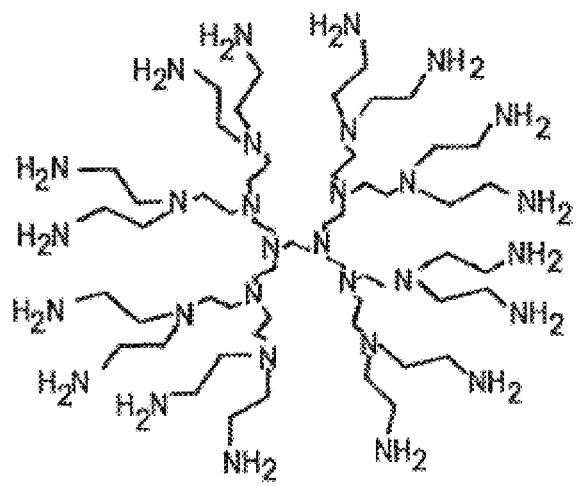
Figure 2A:
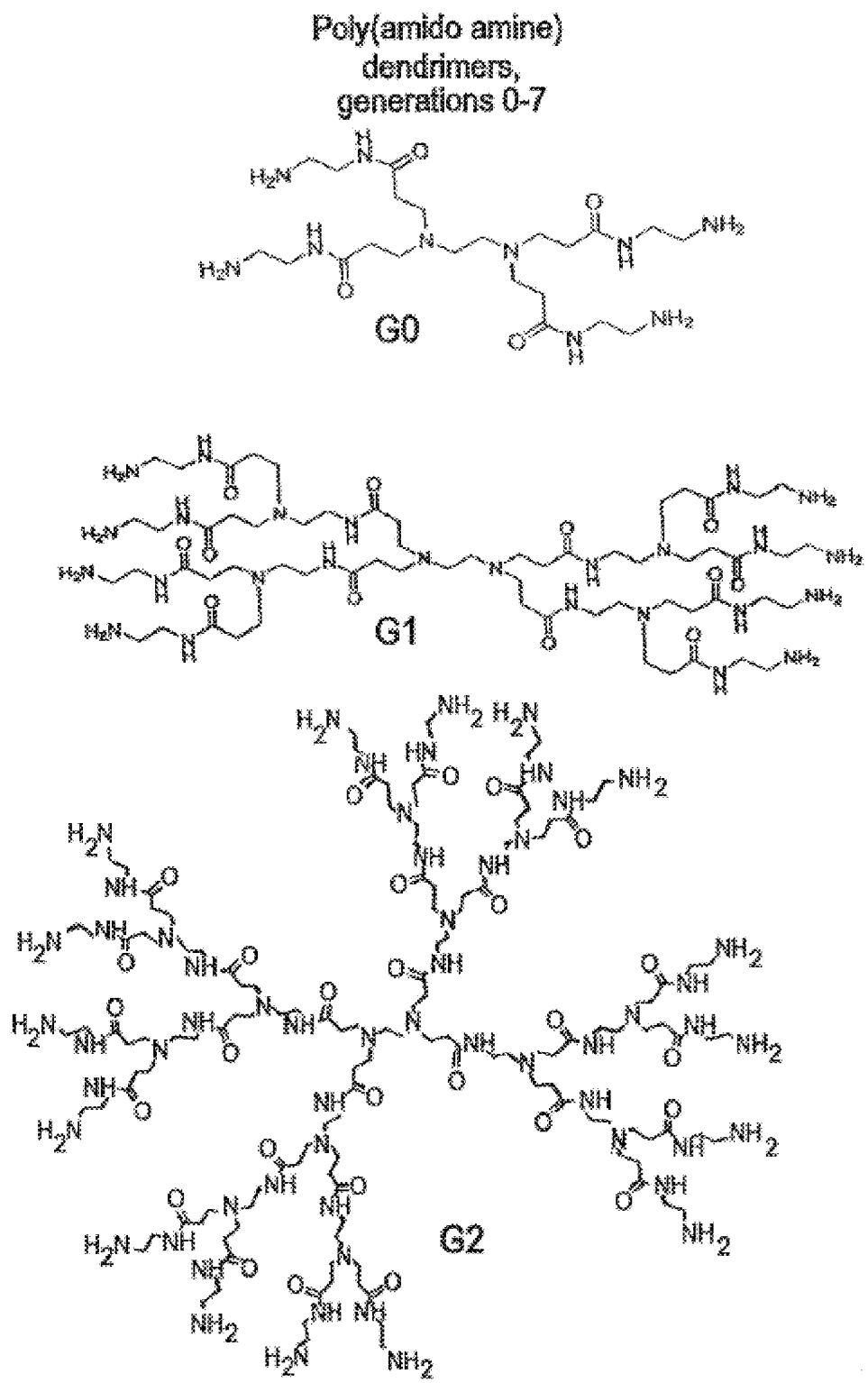
Figure 2A:
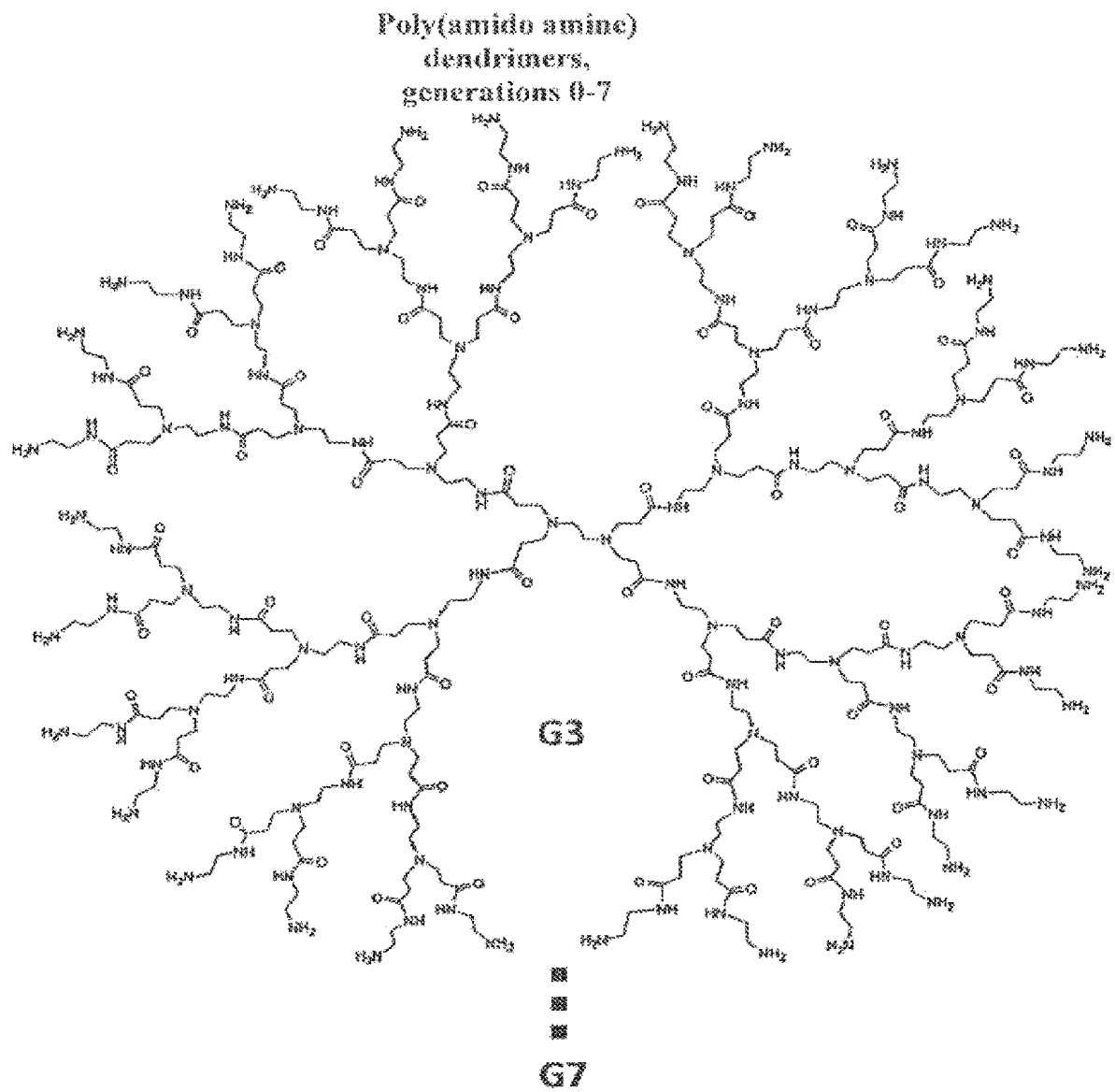
Figure 2B:
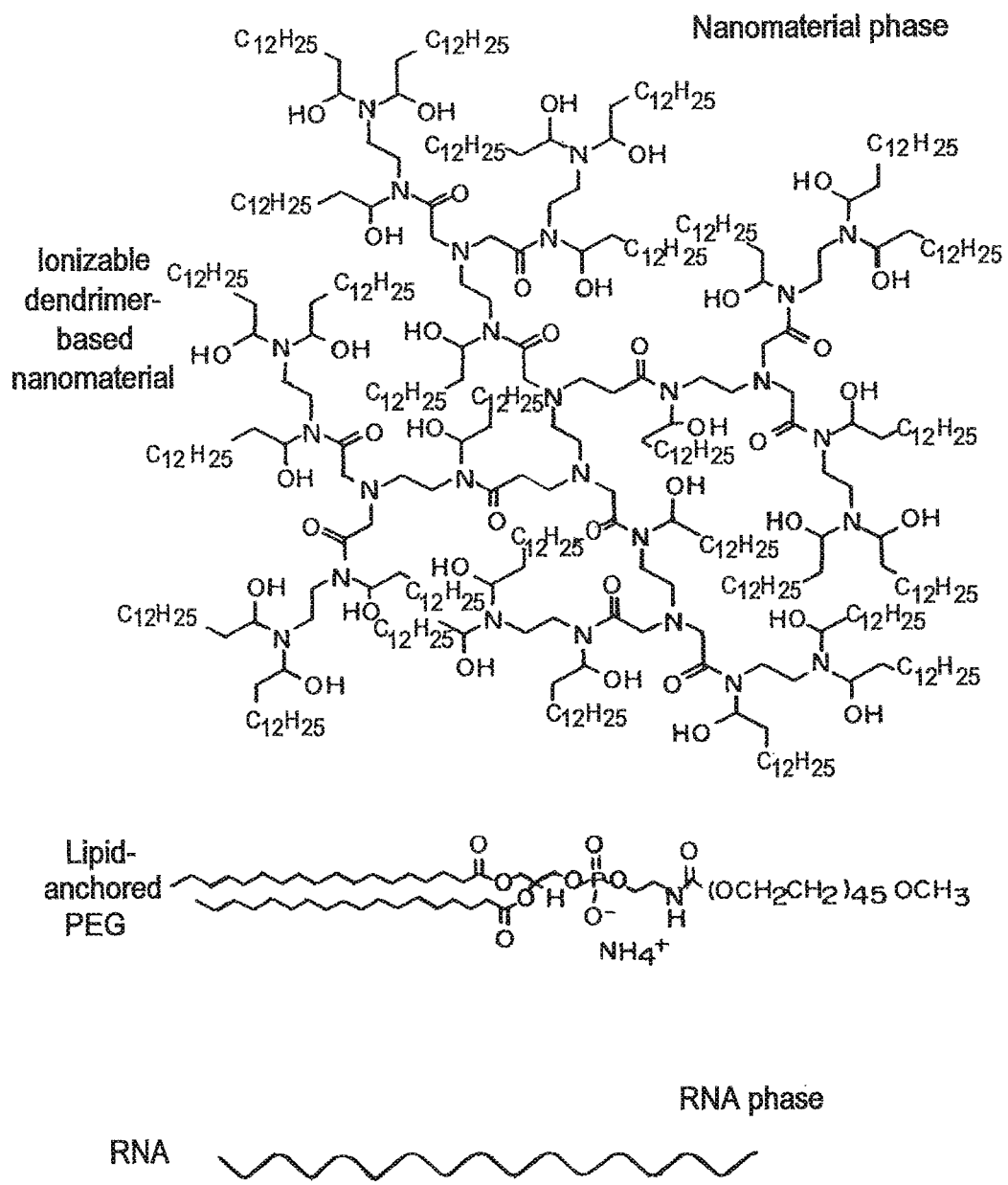
Figure 2C:
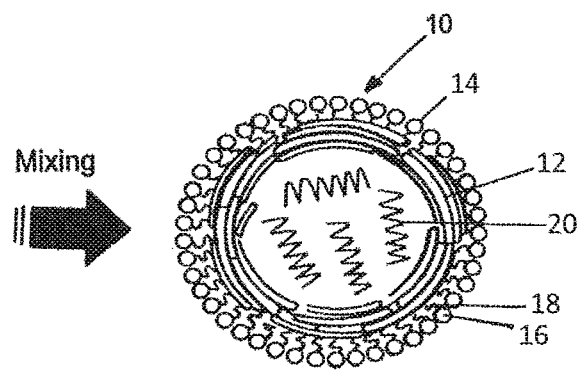

Molecular structures of generations 0-3 (G0-G3) of PAMAM dendrimers are provided in FIG. 2A.

Polyethylenimine (also known as polyaziridine) is a polymer with repeating units of an amine group and a two-carbon aliphatic ($CH_2CH_2$) spacer.

FORMULA II: A polyethylene imine monomer and repeating units of a Poly(ethylene-imine) (PEI) monomer.

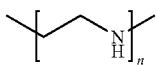

When MDNPs are formed from PEI dendrimers, generations from 0 to 7 PEI dendrimers are typically used. For example, MDNPs can be formed from generation 0 PEI dendrimers (G0); generation 1 (G1) PEI dendrimers; generation 2 (G2) PEI dendrimers; generation 3 (G3) PEI dendrimers; generation 4 (G4) PEI dendrimers; generation 5 (G5) PEI dendrimers; generation 6 (G6) PEI dendrimers; or generation 7 (G7) PEI dendrimers. An exemplary scheme for the structures of successively increasing generations (G1-G3) of PEI dendrimers is depicted in Scheme II, below.

PEI is commercially available from multiple sources, including Sigma-Aldrich (Cat. No. 482595).

Molecular structures of generations 1-3 (G1-G3) of PEI dendrimers are provided in FIG. 2A.

Diaminobutane amine polypropylenimine tetramine (DAB Am 4) is a polymer with a 1,4-diaminobutane core (4-carbon core) with 4 surface primary amino groups.

FORMULA III: Molecular structure of a generation 1 (G1) Diaminobutane amine polypropylenimine tetramine (DAB-Am 4).

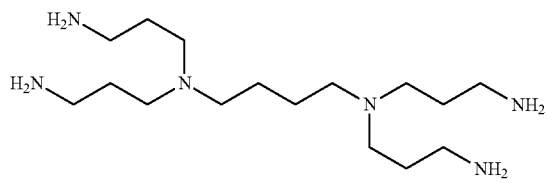

When MDNPs are formed from DAB-AM 4 dendrimers, generations from 0 to 7 DAB-AM 4 dendrimers are typically used. For example, MDNPs can be formed from generation 0 DAB-AM 4 dendrimers (G0); generation 1 (G1) DAB-AM 4 dendrimers; generation 2 (G2) DAB-AM 4 dendrimers; generation 3 (G3) DAB-AM 4 dendrimers; generation 4 (G4) DAB-AM 4 dendrimers; generation 5 (G5) DAB-AM 4 dendrimers; generation 6 (G6) DAB-AM 4 dendrimers; or generation 7 (G7) DAB-AM 4 dendrimers. An exemplary scheme for the structures of successively increasing generations (G1-G3) of DAB-AM 4 dendrimers is depicted in Scheme III, below.

DAB-Am 4 is commercially available from multiple sources, including Sigma-Aldrich (Cat. No. 460699).

The molecular structure of generations 1-4 (G1-G4) of DAB-Am 4 dendrimers is provided in FIG. 2A.

The MDNPs may be formed of one or more different dendrimers. Each dendrimer of the dendrimer complex may be of similar or different chemical nature than the other dendrimers (e.g., the first dendrimer can be a PAMAM dendrimer, while the second dendrimer can in be a POPAM dendrimer). In some embodiments, the first or second dendrimer may further include an additional agent. The dendrimer complex can include multiple dendrimers. For example, the nanoparticle can include a third dendrimer; wherein the third-dendrimer is complexed with at least one other dendrimer. A third agent can be complexed with the third dendrimer. In another embodiment, the first and second dendrimers are each complexed to a third dendrimer, wherein the first and second dendrimers are PAMAM dendrimers and the third dendrimer is a POPAM dendrimer. Additional dendrimers can be incorporated. When multiple dendrimers are utilized, multiple agents can also be incorporated. Typically, reaction between the primary and secondary amines on the dendrimers with terminal epoxides creates dendrimers substituted with alkyl chains.

a. Epoxides

Typically, dendrimers are modified by reaction with alkyl epoxides. In some embodiments, the alkyl epoxides react with amino groups present on the dendrimers to form an alkylated dendrimer.

Epoxides can have the structure shown in Formula IV, where R can be any linear alkyl group between C1 and C30, inclusive, preferably between C6 and C18.

FORMULA IV: General structural formulae for an epoxide with repeating units, where R can be any linear alkyl group between C1 and C30 inclusive.

Formula V:
Structural formulae for a representative group of epoxides ($C_6$-$C_{18}$)

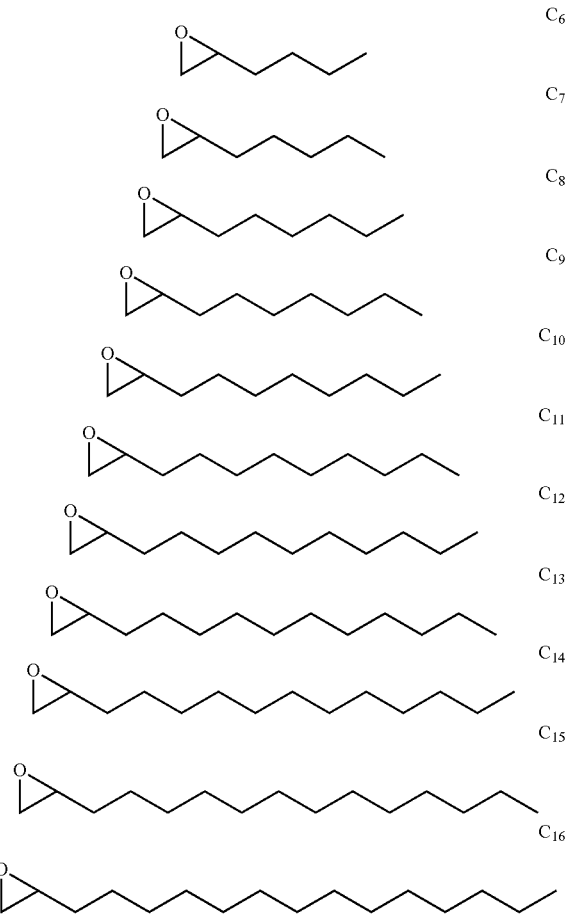

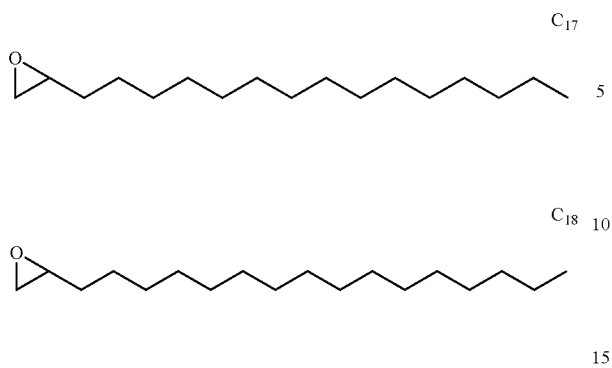

C17

C18

Exemplary epoxides include 2-tridecyloxirane ($C_{15}H_{30}O$) and 1,2-Epoxydodecane ($C_{12}H_{24}O$).

An exemplary scheme for modification of dendrimers with epoxides is provided in scheme I, below. Scheme I depicts the synthetic route of the dendrimer-lipid via reaction between the primary and secondary amines within a dendrimer with the terminal epoxide on an alkyl chain. Typically, reactions require ethanol solvent; 90° C. reaction temperature; and a minimum 72 hour reaction time in the dark.

SCHEME I: Exemplary reaction scheme to form ionizable dendrimer-based nanomaterials for use in the formation of MDNPs.

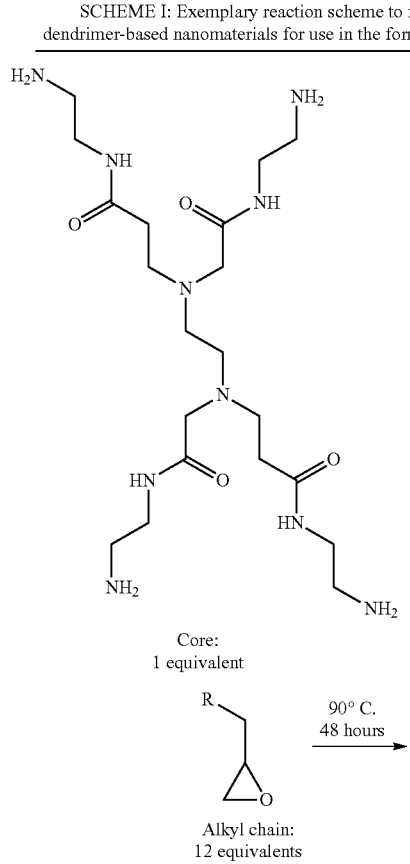

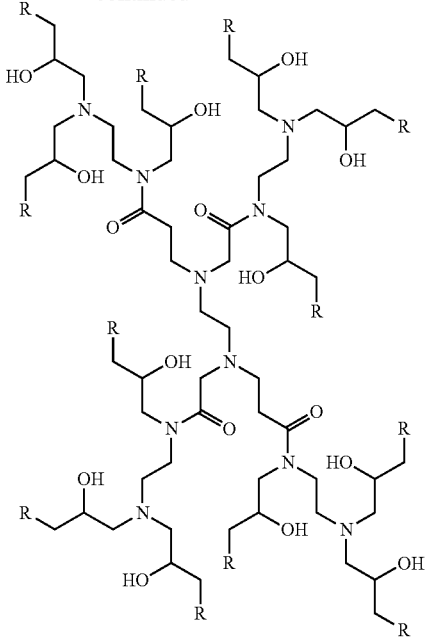

2. Amphiphilic Polymers

The MDNPs include hydrophililic-hydrophobic polymers such as PEG-lipid conjugates which are biocompatible, non-immunogenic and are non-toxic.

a. Hydrophobic Component

One type of hydrophobic component which is well adapted to association within a hydrophobic or lipidic bilayer is a phospholipid such as phosphatidylethanolamine (PE), cholesterol, ceramides, lysolipids, lysophospholipids and sphingolipids. The linkage between PE and the bound polymer can include esters and/or carbamate derivatives. The PE can be a saturated or unsaturated PE. Ceramides can be short chain (e.g., C8), intermediate chain (e.g., C14) or long chain (e.g. C20) fatty amides, or fatty acid (e.g., oleic acid) derivatives. Neutral and anionic lipids include, but are not limited to, phosphatidylcholines (PC) (such as egg PC, soy PC), 1,2-diacyl-glycero-3-phosphocholines; phosphatidylserine (PS), phosphatidylglycerol, phosphatidylinositol (PI); glycolipids; sphingophospholipids such as sphingomyelin, sphingoglycolipids (also known as 1-ceramidyl glucosides) such as ceramide galactopyranoside, gangliosides and cerebrosides; fatty acids, sterols containing a carboxylic acid group such as cholesterol or derivatives thereof; and 1,2-diacyl-sn-glycero-3-phosphoethanolamines, including 1,2-dioleoyl-sn-Glycero-3-phosphoethanolamine or 1,2-dioleolylglyceryl phosphatidylethanolamine (DOPE), 1,2-dihexadecylphosphoethanolamine (DHPE), 1,2-distearoylphosphatidylcholine (DSPC), 1,2-dipalmitoylphosphatidylcholine (DPPC), and 1,2-dimyristoylphosphatidylcholine (DMPC).

Trimethyl ammonium salts, also referred to as TAP lipids, for example as a methylsulfate salt. Suitable TAP lipids include, but are not limited to, DOTAP (dioleoyl-), DMTAP (dimyristoyl-), DPTAP (dipalmitoyl-), and DSTAP (distearoyl-). Other suitable cationic lipids include dimethyldioctadecyl ammonium bromide (DDAB), 1,2-diacyloxy-3-trimethylammonium propanes, N-[1-(2,3-dioloyloxy)propyl]-N,N-dimethyl amine (DODAP).

b. Hydrophilic Component

A wide variety of hydrophilic polymers can be included, including poly β-amino esters and 1, 2-amino alcohol lipids. In some embodiments, the polymers are alkyl-modified polymers, such as alkyl modified poly(ethylene glycol). Other exemplary polymers include poly(alkylene glycol), polysaccharides, poly(vinyl alcohol) s, polypyrrolidones, polyoxyethylene block copolymers (e.g., PLURONIC®), polyethylene glycol (PEG) and copolymers thereof. Preferred hydrophilic polymers are biocompatible (i.e., do not induce a significant inflammatory or immune response) and non-toxic. Examples of suitable hydrophilic polymers include, but are not limited to, poly(alkylene glycols) such as polyethylene glycol (PEG), poly(propylene glycol) (PPG), and copolymers of ethylene glycol and propylene glycol, poly(oxyethylated polyol), poly(olefinic alcohol), polyvinylpyrrolidone), poly(hydroxyalkylmethacrylamide), poly(hydroxyalkylmethacrylate), poly(saccharides), poly(amino acids), poly(hydroxy acids), poly(vinyl alcohol), and copolymers, terpolymers, and mixtures thereof.

In preferred embodiments, the one or more hydrophilic polymer component contains a poly(alkylene glycol) chain. The poly(alkylene glycol) chains may contain between 1 and 500 repeat units, more preferably between 40 and 500 repeat units. Suitable poly(alkylene glycols) include polyethylene glycol, polypropylene 1,2-glycol, poly(propylene oxide), polypropylene 1,3-glycol, and copolymers thereof.

In some embodiments, the one or more hydrophilic polymer components are copolymers containing one or more blocks of polyethylene oxide (PEO) along with one or more blocks composed of other biocompatible polymers (for example, poly(lactide), poly(glycolide), poly(lactide-co-glycolide), or polycaprolactone). The one or more hydrophilic polymer segments can be copolymers containing one or more blocks of PEO along with one or more blocks containing polypropylene oxide (PPO). Specific examples include triblock copolymers of PEO-PPO-PEO, such as POLOXAMERS™ and PLURONICS™.

Polyethylene glycol (PEG). PEG is one of the most commonly used shielding agents. The size, relative quantity and distribution of the amphiphilic PEG included in the MDNPs can influence the biophysical characteristics of the resulting modified dendrimer-based nanoparticle (MDNPs), such as structural features and charge density.

The physical properties of the MDNPs is directly associated with the size, relative quantity and distribution of the amphiphilic PEG (i.e., the extent of pegylation). Exemplary properties that can be modified include the efficacy of uptake of the MDNPs by one or more types of eukaryotic cells, the speed and efficacy of the intra-cellular delivery of therapeutic, prophylactic and diagnostic agents, and the immunogenicity and cytotoxicity of the MDNP. In certain embodiments, pegylation results in charge neutralization of the MDNP.

Typically, the amphiphilic PEG includes a short-chain oligo-ethylene glycol. Exemplary oligoi-ethylene glycols include di-ethylene glycol, tri-ethylene glycol, tetra-ethylene glycol, penta-ethylene glycol, hexa-ethylene glycol, etc.

Formula VI: Repeating unit of a short chain oligo-ethylene glycol (n = 1-6) PEG monomers.

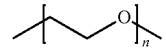

In some embodiments, the amphiphilic polymer is a phospholipid conjugated to monomethoxy polyethyleneglycol (mPEG). In certain embodiments, the lipid-associated PEG or mPEG is a branched or "multi-arm" PEG. MDNPs can include multiarm polyethylene glycol having at least two branches bearing sulfhydryl or thiopyridine terminal groups; however, PEG polymers bearing other terminal groups such as succinimidyl or maleimide terminations can be used.

The MDNPs can include polyethylene glycol polymers having different molecular weights. For example, the PEGs can have molecular weights between approximately 100 Da (i.e., PEG 100 Da) and approximately 12,000 kDa (i.e., PEG 12 KDa), inclusive. MDNPs can be formed from a single species of amphiphilic PEG, or from two or more different species of amphiphilic PEGs. For example, MDNPs can be formed with multiple different species of lipid-anchored PEGs having different molecular weights.

MDNPs can be formed using a single amphiphilic polymer species, or a mixture of multiple different amphiphilic polymer species. The amphiphilic polymers can be modified with adducts. For example, amphiphilic polymers can be modified with the same or different the one or more different adducts. Therefore, modified dendrimer-based nanoparticle can be formed using one or more lipid-anchored polymers, optionally including mixtures of the same or different adducts.

In some embodiments, MDNPs are formulated with 1,2-dimyristoyl-sn-glycero-3-phosphoethanolamine-[methoxy (polyethylene glycol)] ($C_{14}$-MPEG) molecules. $C_{14}$-MPEG typically include an mPEG component with a molecular weight of between 350 Da and 12,000 Da, more preferably between 1,000 Da and 5,000 Da, most preferably 2,000 Da.

An exemplary lipid-anchored mPEG is a 1,2-dimyristoyl-sn-glycero-3-phosphoethanolamine-N-[methoxy (polyethylene glycol)-2000], with the molecular structure illustrated in Formula VII, ($C_{14}$-mPEG (2000)).

Formula VII: Molecular structure of 1,2-dimyristoyl-sn-glycero-3-phosphoethanolamine-N-[methoxy(polyethylene glycol)-2000].

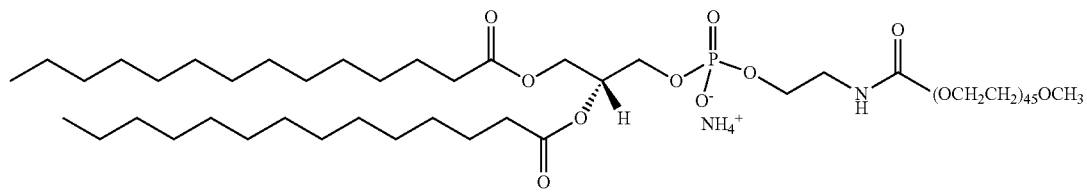

In some embodiments, MDNPs are formulated with the amphiphilic polymer $C_{14}$-mPEG2000. In other embodiments, MDNPs are formulated with $C_{14}$-mPEG molecules having different molecular weight mPEG, such as $C_{14}$- mPEG (350); C₁₄-mPEG (550); C₁₄-mPEG (750); C₁₄-mPEG (1000); C₁₄-mPEG (3000); or C₁₄-mPEG (5000). In some embodiments the PEG is mPEG 5000 (i.e., 1,2-dioleoyl-sn-glycero-3-phosphoethanolamine-N-[methoxy (polyethylene glycol)-5000]). The lipidic component can include saturated or non-saturated fatty acidic moieties.

In some embodiments, MDNPs are formulated with 1,2-distearoyl-sn-glycero-3-phosphoethanolamine-N-[amino (polyethylene glycol)-2000] (DSPE-MPEG) molecules. DSPE-MPEG typically include an mPEG component with a molecular weight of between 350 Da and 12,000 Da, more preferably between 1,000 Da and 5,000 Da, most preferably 2,000 Da.

An exemplary lipid-anchored mPEG is a 1,2-distearoyl-sn-glycero-3-phosphoethanolamine-N-[amino (polyethylene glycol)-2000], with the molecular structure illustrated in Formula VIII, (DSPE-mPEG (2000)).

Ceramide; C8 MPEG2000 Ceramide; C16 MPEG2000 Ceramide; C8 MPEG5000 Ceramide; or C16 MPEG5000 Ceramide.

In some embodiments, one or more amphiphilic polymers are modified by addition of one or more moieties that impart distinct structural and functional properties to the polymers. For example, in some embodiments, one or more amphiphilic polymers are modified by addition of polypeptides or other small molecules. Modified lipid-bound polymers can be used to impart one or more distinct functional or structural properties to modified dendrimer-based nanoparticle (MDNPs), as compared to the same MDNPs in the absence of the modification. Exemplary functional or structural properties include variation of the hydrodynamic volume, hydrophobicity, antigenicity, receptor-binding specificity and serum half-life of the modified dendrimer-based nanoparticle (MDNPs).

Formula VIII: Molecular structure of 1,2-dimyristoyl-sn-glycero-3-phosphoethanolamine-N-[methoxy(polyethylene glycol)-2000].

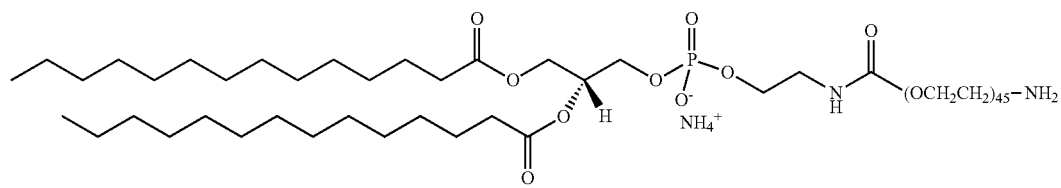

In some embodiments, MDNPs are formulated with the amphiphilic polymer DSPE-mPEG. In other embodiments, MDNPs are formulated with DSPE-mPEG molecules having different molecular weight mPEG, such as DSPE-mPEG (350); DSPE-mPEG (550); DSPE-mPEG (750); DSPE-mPEG (1000); DSPE-mPEG (2000); DSPE-mPEG (3000); or DSPE-mPEG (5000). The lipidic component can include saturated or non-saturated fatty acidic moieties.

In other embodiments, MDNPs are formulated with the amphiphilic polymer N-octanoyl-sphingosine-1-{succinyl [methoxy (polyethylene glycol)]} (C8 MPEG Ceramide) molecules. C8 MPEG Ceramide molecules typically include an mPEG component with a molecular weight of between 750 Da and 5,000 Da, more preferably between 1,000 Da and 5,000 Da, most preferably 2,000 Da.

An exemplary ceramide-anchored mPEG is a N-octanoyl-sphingosine-1-{succinyl [methoxy (polyethylene glycol) 2000]} with the molecular structure illustrated in Formula IX, (C8 MPEG2000 Ceramide).

3. Therapeutic, Prophylactic and Diagnostic Agents

MDNPs include one or more therapeutic, prophylactic and diagnostic agents for delivery to the intra-cellular space. In some embodiments, one or more therapeutic, prophylactic and diagnostic agents are nucleic acids, such as mRNAs or repRNAs that encode exogenous gene sequences. In some embodiments, the exogenous gene sequences encode one or more antigens specific to a virus, pathogen, micro-organism or a cancer.

MDNPs protect the enclosed therapeutic, prophylactic and diagnostic agents from chemical, photo- and enzymatic degradation. RNA molecules enclosed within a MDNP are stabilized against degradation by nucleases, hydroxyl radical, UV light, and Mg²⁺-mediated inline attack, avoiding the need for chemical modification to stabilize and deliver RNA to cells in vivo. The high-stability of MDNPs enables storage for long periods of time and allows for a broad range of application methods, including distribution as aerosols, solutions, powders, etc.

Formula IX: Molecular structure of N-octanoyl-sphingosine-1-{succinyl[methoxy(polyethylene glycol)2000]}.

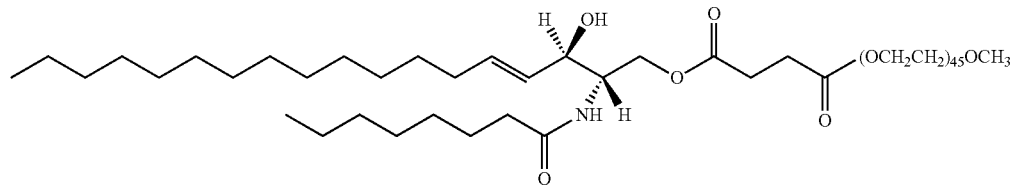

In some embodiments, MDNPs are formulated with the ceramide-anchored polymer C8 MPEG2000 Ceramide. In other embodiments, MDNPs are formulated with C8 MPEG Ceramide molecules having different molecular weight mPEG, such as C8 MPEG750 Ceramide; C16 MPEG750 a. Nucleic Acids

In some embodiments, the therapeutic, prophylactic and diagnostic agents encapsulated within the MDNPs include one or more nucleic acids. Representative examples of nucleic acid therapeutic, prophylactic and diagnostic agents include DNA plasmid vectors such as expression vectors, RNA molecules such as iRNA, siRNA, ribozymes, aptamers, repRNAs, gRNA/sgRNA (guide RNA/single guide RNA for CRISPR-based gene editing), and mRNAs.

In some embodiments, the therapeutic, prophylactic and diagnostic agents encapsulated within the MDNPs include one or more nucleic acid expression vectors for expression of one or more genes in the recipient cell. In some embodiments, the genes are exogenous to the host organism. In other embodiments the genes are native to the host organism. In certain embodiments, the genes are a modified variant of those typically associated with the organism, such as a mutant form of one or more alleles.

Representative examples of nucleic acid expression vectors include DNA plasmid vectors such as expression, cloning, cosmid and transformation vectors such as, but not limited to, viral vectors, vectors derived from bacteriophage nucleic acid, and synthetic oligonucleotides including chemically synthesized DNA; and RNA vectors, including replicating RNA. In general, any expression vector into which a gene segment may be inserted so as to bring about the replication and expression of the inserted segment can be included in the modified dendrimer-based nanoparticles, for delivery into the cells of a subject.

Typically, nucleic acid expression vectors of the MDNPs are engineered to express a heterologous nucleic acid sequence in a target cell, such as the cells of a subject, and include one or more expression control sequences. Expression vectors can include a promoter, a heterologous nucleic acid sequence operably linked to the promoter, a eukaryotic transcription terminator operably linked to the heterologous nucleic acid sequence, and an origin of replication.

In general, plasmid vectors containing replicon and control sequences that are derived from species compatible with the host cells are used in connection with these hosts. The vector ordinarily carries a replication site, as well as marking sequences that are capable of providing phenotypic selection in transformed cells. Different host cells have characteristic and specific mechanisms for the post-translational processing and modification of proteins. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences.

In certain embodiments, the MDNP includes one or more ribonucleic acid (RNA) molecules. RNA is cost-effective to produce in large quantities and can be generated endotoxin-free from any given discovered sequence from commercially synthesized DNA precursors with nearly same-day rapidity. It is safer and easier to administer than DNA because it poses no risk of genome integration, and only requires access to cell cytoplasm to function. Moreover, due to the availability of self-replicating mRNAs (repRNAs) based on alphavirus or flavivirus genomes, very low doses can be employed to achieve maximal immunogenicity and antigen production levels.

In certain embodiments, the MDNP includes one or more replicating ribonucleic acids (repRNAs), also known as replicons. Replicating RNAs are self-amplifying RNAs that have the potential to deliver genes, including genes encoding vaccine antigens. RepRNAs are attenuated virus genomes lacking viral structural proteins required for the production of progeny virions. However, repRNAs retain the capability of translation and replication and can therefore effectively increase the half-life of translation of mRNA. Thus, delivery of RepRNAs encoding one or more exogenous genes to cells can effectively increase the translation and expression of the exogenous genes in the cells relative to that resulting from delivery of an equal molar amount of conventional mRNAs encoding the one or more exogenous genes to the cells. In some embodiments, the RepRNAs are non-cyto-pathogenic RepRNAs.

Alphaviral self-amplifying repRNA typically includes a 5' Cap; 5' untranslated region (5'UTR), non-structural genes (e.g., NSP1-4) encoded within a first open reading frame, a genomic promoter region (e.g., 26S sub-genomic promoter), a second open reading frame, a 3' untranslated region (3'UTR) and a 3' poly-adenylated tail. repRNA molecules are typically between 9,000 and 20,000 nucleotides in length, depending upon the size of the encoded genic sequence (See FIGS. 1A-1C).

The non-structural genes encode an RNA-dependent RNA polymerase (RdRp). Typically, the RdRp does not tolerate classical nucleotide modifications that are used to protect conventional mRNA against endonucleose and auto-catalytic degradation. Thus, nano-encapsulation is necessary for the effective deployment in vaccine platforms. The repRNA is modular and the second open reading frame can be engineered to sequence for a complete gene, such as an exogenous gene of interest (GOI).

repRNAs including one or more desired gene sequences, such as an antigen gene, encoded within the second open reading frame can be used. When the repRNA is deposited into the cytoplasm of a host cell, the RNA dependent RNA polymerase (RdRp) encoded by the repRNA NS genes is expressed within the cell. The RdRp can then replicate the entire repRNA, or the RdRp copies of the repRNA-encoded antigen only (i.e., by virtue of a sub-genomic promoter).

Replicon RNAs increase the overall efficiency of RNA-mediated gene delivery, because the repRNA can synthesize more copies of the full-length replicon, as well as more copies of mRNAs encoding the genes included within the second open reading frame. The host cell ribosomes continue to translate the full-length replicon copies or the shorter antigen-only mRNAs, leading to enhanced expression of the genes encoded by the repRNA (see FIG. 1A).

Self-replicating RNA can generate a larger number of mRNA templates than could easily be delivered and guaranteed to arrive in the correct cytosolic localization of the targeted cell. The self-replicative nature of repRNAs closely mimics that of a natural infectious viral particle, and will be more efficient at inducing both humoral and cytotoxic cellular immune defense arms.

A single repRNA can include nucleic sequences encoding one or more exogenous genes. Therefore, in some embodiments, MDNPs include one or more repRNAs encoding one or more exogenous gene sequences each.

repRNAs derived from different viral genomes can impart different functional properties to the expression and transcription of exogenous genes. For example, different repRNA species encoding the same exogenous gene can give rise to different rates and different half-lives of transcription of the exogenous gene. Generally, translational efficiency (including activation or complete inhibition of translation) of genes can be controlled by the UTRs.

In some embodiments, a single MDNP includes more than one different repRNA derived from different viral genomes. When two or more repRNAs derived from different viral genomes are encapsulated within the same MDNP, the repRNAs can encode one or more of the same or different exogenous genes. When more than one repRNA is encapsulated within a single MDNP, the repRNAs can be the same or different species of repRNA.

Typically, repRNAs are generated by modification of 'positive strand' RNA viruses. The modified viral genomes function as both mRNA and templates for intracellular self-replication. This contrasts with 'negative strand' viruses, which must be delivered with their own polymerase to promote the initial replication and formation of mRNA templates. Delivery of the latter is more reliant on the use of virus-like particles, and not so pertinent to synthetic particle-based delivery. Exemplary repRNAs include modified viral genomes of viruses belonging to the Alphavirus and Flavivirus genuses.

Alphaviruses belong to the group IV Togaviridae family of viruses. Typically, these viruses have a total genome length ranging between 11,000 and 12,000 nucleotides, including a 5' cap and 3' poly-A tail. The four non-structural protein genes are encoded in the 5' two-thirds of the genome. Replication occurs within the cytoplasm of the host cell. The formation of repRNAs based on the modification of Alphavirus genomes is well established in the art (Atkins, et al., *Expert Rev Mol Med*, 10: e33 (2008); Khromykh, *Curr Opin Mol Ther*, 2:555-569 (2000); Lundstrom *Curr Opin Mol Ther* 4:28-34. (2002); and Rayner, *Rev Med Virol.*, 12:279-296. (2002)).

In some embodiments, repRNAs encapsulated within MDNPs are derived from a modified alphavirus species, including, but not limited to, a Venezuelan equine encephalitis virus (VEEV) (including the Cabassou virus, Everglades virus, Mosso das Pedras virus, Mucambo virus, Paramana virus, Pixuna virus, Rio Negro virus, Trocara virus and Venezuelan equine encephalitis virus subtypes); a Semliki Forest virus (SFV) (including Bebaru virus, Chikungunya virus, Mayaro virus, O'Nyong Nyong virus, Ross River virus and Semliki Forest virus subtypes); a Sindbis virus (SV); an Eastern Equine Encephalosis virus (EEEV); a Barmah Forest virus (BFV); a Middelburg virus (MV); a Ndumu virus (NV); and a Western equine encephalitis (WEEV), including the Aura virus, Babanki virus Kyzylagach virus, Sindbis virus, Ockelbo virus and Whataroa virus subtypes).

Flaviviruses belong to the genus of viruses in the family Flaviviridae. Flaviviruses are positive-sense, single-stranded RNA viruses of approximately 10,000-11,000 nucleotides, including a 5' cap, but lacking a 3' poly-A tail. Typically, the Flavivirus genome encodes 3 structural proteins and 8 non-structural proteins. Flaviviruses replicate and assemble in the cytoplasm and primarily infect mammalian hosts, including humans. The formation of repRNAs based on the modification of Flavivirus genomes is well established in the art (Kofler, et al., *Proc. Natl. Acad. Sci. USA*, 101, 1951-1956 (2004); Mccullough, et al., Vaccines 2014, 2, 735-754 (2004)).

In some embodiments, repRNAs encapsulated within MDNPs are derived from a modified Flavivirus species, including, but not limited to, West Nile virus (WNV), Aroa virus; Japanese encephalitis virus; Dengue virus (DV), tick-borne encephalitis virus, and Yellow fever virus.

In some embodiments, the MDNPs include messenger ribonucleic acid sequences (mRNA). mRNA is a single-stranded transcript of a gene, including a 5' cap, 5' untranslated region (5'UTR), a coding region that includes a translational start codon, the nucleotide sequence for a complete gene, a translation stop codon, a 3' untranslated region (3'UTR) a poly-A addition site, including 100-200 Adenines added to the 3' end. mRNA molecules are typically between 200 and 10,000 nucleotides in length, depending upon the size of the encoded genic sequence.

Eukaryotic mRNA within the cytoplasm of a host cell is translated by ribosomes, and translational efficiency (including activation or complete inhibition of translation) can be controlled by the UTRs. Proteins that bind to either the 3' or 5' UTRs can influence translation by mediating the ribosome's ability to bind to the mRNA. Translation can occur at ribosomes free-floating in the cytoplasm, or directed to the endoplasmic reticulum by the signal recognition particle.

In some embodiments, the therapeutic, prophylactic and diagnostic agents encapsulated within MDNPs are mRNA molecules encoding genes that can be expressed in the cells of a subject. The mRNAs can encode exogenous genes, such as peptide antigens. One or more mRNAs encoding one or more exogenous genes can be enclosed within a single MDNP. In some embodiments, the MDNP includes two or more molecules of the same mRNA. In other embodiments, the MDNP includes two or more different mRNAs. For example, a single MDNP can include 2, 3, 4, 5, 6, 7, 8, 9, 10, 20, or more than 20 different mRNAs. When two or more different mRNAs are encapsulated within a single MDNP, the two or more different mRNAs can be present in equal (i.e., 1:1) or unequal (i.e., >1:1) molar ratios. For example, two mRNAs can be present within the MDNP at a molar ratio of 1:1, 2:1, 3:1, 4:1, 10:1 or greater than 10:1.

When the therapeutic, prophylactic and diagnostic agents encapsulated within the MDNPs include one or more nucleic acids, such as expression vectors or mRNAs, the vectors can encode one or more genic regions for expression within the recipient cell. Typically the genes are exogenous (i.e., heterologous) genes to the target cell. The heterologous nucleic acid sequence can be any nucleic acid sequence that that encodes genetic information for the synthesis of a portion of or a whole RNA, or a portion of or a whole protein, for the purpose of production of one or more gene products, and/or modulating gene expression in the recipient. In some embodiments, the heterologous nucleic acid encodes an antigen. In other embodiments the heterologous nucleic acid sequence encodes an element that initiates and/or moderates a biological response in the host cell. For example, the heterologous protein can inhibit expression of one or more genes.

An exemplary list of heterologous nucleic acid sequences include genes encoding antigens, ribozymes, enzymes, peptides, structural proteins, structural RNA, shRNA, siRNA, miRNA, gRNA/sgRNA (guide RNA/single guide RNA for CRISPR-based gene editing), transcription factors, signaling molecules and fragments or variants thereof. In an embodiment, the heterologous sequence encodes an antigen.

The heterologous sequence may optionally contain a nucleic acid sequence (i.e., a targeting sequence) that enables targeting to a specific location (e.g. organelle within the cell). In some embodiments, the heterologous sequence encodes an antigen.

In certain embodiments, the heterologous nucleic acid sequence is a functional nucleic acid. Functional nucleic acids that inhibit the transcription, translation or function of a target gene are described.

Functional nucleic acids are nucleic acid molecules that have a specific function, such as binding a target molecule or catalyzing a specific reaction. As discussed in more detail below, functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the target polypeptide itself. Functional nucleic acids are often designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place. Therefore the compositions can include one or more functional nucleic acids designed to reduce expression or function of a target protein.

Methods of making and using vectors for in vivo expression of the described functional nucleic acids such as antisense oligonucleotides, siRNA, shRNA, miRNA, EGSs, gRNA, sgRNA, ribozymes, and aptamers are known in the art.

In certain embodiments, the functional nucleic acids are antisense molecules. Antisense molecules are designed to interact with a target nucleic acid molecule through either canonical or non-canonical base pairing. The interaction of the antisense molecule and the target molecule is designed to promote the destruction of the target molecule through, for example, RNAsc H mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant (Kd) less than or equal to 10-6, 10-8, 10-10, or 10-12.

In certain embodiments, the functional nucleic acids are aptamers. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with Kds from the target molecule of less than 10-12 M. It is preferred that the aptamers bind the target molecule with a Kd less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a Kd with the target molecule at least 10, 100, 1000, 10,000, or 100,000 fold lower than the Kd with a background binding molecule. It is preferred when doing the comparison for a molecule such as a polypeptide, that the background molecule be a different polypeptide.

The functional nucleic acids can be ribozymes. Ribozymes are nucleic acid molecules that are capable of catalyzing a chemical reaction, either intra-molecularly or inter-molecularly. It is preferred that the ribozymes catalyze intermolecular reactions. Different types of ribozymes that catalyze nuclease or nucleic acid polymerase-type reactions which are based on ribozymes found in natural systems, such as hammerhead ribozymes are described. Ribozymes that are not found in natural systems, but which have been engineered to catalyze specific reactions de novo are also described. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for targeting specific cleavage of nucleic acids because recognition of the target substrate is based on the target substrates sequence.

The functional nucleic acids can be triplex forming oligonucleotide molecules. Triplex forming functional nucleic acid molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a Kd less than $10^{-6}$, $10^{-8}$, $10^{-10}$, or $10^{-12}$.

The functional nucleic acids can be external guide sequences. External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA: EGS complex to mimic the natural tRNA substrate. Similarly, eukaryotic EGS/RNAse P-directed cleavage of RNA can be utilized to cleave desired targets within eukaryotic cells. Representative examples of how to make and use EGS molecules to facilitate cleavage of a variety of different target molecules are known in the art.

In some embodiments, the functional nucleic acids induce gene silencing through RNA interference (siRNA). Expression of a target gene can be effectively silenced in a highly specific manner through RNA interference.

An RNA polynucleotide with interference activity of a given gene will down-regulate the gene by causing degradation of the specific messenger RNA (mRNA) with the corresponding complementary sequence and preventing the production of protein (see Sledz and Williams, *Blood,* 106 (3):787-794 (2005)). When an RNA molecule forms complementary Watson-Crick base pairs with an mRNA, it induces mRNA cleavage by accessory proteins. The source of the RNA can be viral infection, transcription, or introduction from exogenous sources.

Gene silencing was originally observed with the addition of double stranded RNA (dsRNA) (Fire, et al. (1998) *Nature,* 391:806-11; Napoli, et al. (1990) *Plant Cell* 2:279-89; Hannon, (2002) *Nature,* 418:244-51). Once dsRNA enters a cell, it is cleaved by an RNase III-like enzyme called Dicer, into double stranded small interfering RNAs (siRNA) 21-23 nucleotides in length that contain 2 nucleotide overhangs on the 3' ends (Elbashir, et al., *Genes Dev.,* 15:188-200 (2001);

Bernstein, et al., *Nature*, 409:363-6 (2001); Hammond, et al., *Nature*, 404:293-6 (2000); Nykanen, et al., *Cell*, 107: 309-21 (2001); Martinez, et al., *Cell*, 110:563-74 (2002)). The effect of iRNA or siRNA or their use is not limited to any type of mechanism.

In one embodiment, a siRNA triggers the specific degradation of homologous RNA molecules, such as mRNAs, within the region of sequence identity between both the siRNA and the target RNA. Sequence specific gene silencing can be achieved in mammalian cells using synthetic, short double-stranded RNAs that mimic the siRNAs produced by the enzyme dicer (Elbashir, et al., *Nature*, 411:494-498 (2001)) (Ui-Tei, et al., *FEBS Lett*, 479:79-82 (2000)). siRNA can be chemically or in vitro-synthesized or can be the result of short double-stranded hairpin-like RNAs (shRNAs) that are processed into siRNAs inside the cell. For example, WO 02/44321 describes siRNAs capable of sequence-specific degradation of target mRNAs when base-paired with 3' overhanging ends, and is herein specifically incorporated by reference for the method of making these siRNAs. Synthetic siRNAs are generally designed using algorithms and a conventional DNA/RNA synthesizer. Suppliers include Ambion (Austin, Texas), ChemGenes (Ashland, Massachusetts), Dharmacon (Lafayette, Colorado), Glen Research (Sterling, Virginia), MWB Biotech (Esbersberg, Germany), Proligo (Boulder, Colorado), and Qiagen (Vento, The Netherlands). siRNA can also be synthesized in vitro using kits such as Ambion's SILENCER® siRNA Construction Kit.

Therefore, in some embodiments, the MDNP includes one or more siRNAs, or one or more vectors expressing an siRNA. The production of siRNA from a vector is more commonly done through the transcription of a short hairpin RNAse (shRNAs). Kits for the production of vectors including shRNA are available, such as, for example, Imgenex's GENESUPPRESSOR™ Construction Kits and Invitrogen's BLOCK-IT™ inducible RNAi plasmid and lentivirus vectors. In some embodiments, the functional nucleic acid is siRNA, shRNA, or miRNA.

b. Antigens

In some embodiments, the exogenous nucleic acid sequence encodes a vaccine antigen. An antigen can include any protein or peptide that is forcign to the subject organism. Preferred antigens can be presented at the surface of antigen presenting cells (APC) of a subject for surveillance by immune effector cells, such as leucocytes expressing the CD4 receptor (CD4 T cells) and Natural Killer (NK) cells. Typically, the antigen is of viral, bacterial, protozoan, fungal, or animal origin. In some embodiments, the antigen is a cancer antigen. Cancer antigens can be antigens expressed only on tumor cells and/or required for tumor cell survival. Certain antigens are recognized by those skilled in the art as immuno-stimulatory (i.e., stimulate effective immune recognition) and provide effective immunity to the organism or molecule from which they derive.

B cell antigens can be peptides, proteins, polysaccharides, saccharides, lipids, nucleic acids, small molecules (alone or with a hapten) or combinations thereof. T cell antigens are proteins or peptides. The antigen can be derived from a virus, bacterium, parasite, plant, protozoan, fungus, tissue or transformed cell such as a cancer or leukemic cell and can be a whole cell or immunogenic component thereof, e.g., cell wall components or molecular components thereof. Suitable antigens are known in the art and are available from commercial government and scientific sources. The antigens may be purified or partially purified polypeptides derived from tumors or viral or bacterial sources. The antigens can be recombinant polypeptides produced by expressing DNA encoding the polypeptide antigen in a heterologous expression system. All or part of an antigenic protein can be encoded by a DNA or RNA molecule for delivery. Antigens may be provided as single antigens or may be provided in combination. Antigens may also be provided as complex mixtures of polypeptides or nucleic acids.

Viral Antigens

In some embodiments, the antigen is a viral antigen. A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (EBOV) (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenza virus A, such as H1N1 strain, and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue DINS3. Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis. Typically, viral antigens encoded by repRNAs are not derived from the native viral genome from which the repRNA was developed.

In some embodiments, the viral antigen in derived from one or more viruses from the Orthomyxovirus family, for example, the Influenza virus A, Influenza virus B, Influenza virus C, Isavirus, Thogotovirus and Quaranjavirus. Exemplary influenza A virus subtypes include H1N1, H1N2, H3N2, H3N1, H5N1, H2N2, and H7N7. Exemplary influenza virus antigens include one or more proteins or glycoproteins such as hemagglutinin, such as HA1 and HA2 subunits, neurominidase, viral RNA polymerase, such as one or more of PB1, PB2 PA and PB1-F2, reverse transcriptase, capsid protein, non-structured proteins, such as NS1 and NEP, nucleoprotein, matrix proteins, such as M1 and M2 and pore proteins. In some embodiments, Influenza A virus antigens include one or more of the Hemagglutinin (HA) or Neuraminidase (NA) glycoproteins or fragments of the HA or NA, including the antigenic sites of the Hemagglutinin HA1 glycoprotein. In an exemplary embodiment, MDNPs include RNA encoding the influenza A/WSN/33 HA protein.

In some embodiments, the viral antigen in derived from one or more viruses from the genus Ebolavirus, for example, the Zaire ebolavirus (EBOV), Sudan ebolavirus (SUDV), Taï Forest ebolavirus (TAFV), Reston ebolavirus (RESTV), and Bundibugyo ebolavirus (BDBV). In an exemplary embodiment, MDNPs include RNA, such as repRNA, encoding the Zaire ebolavirus glycoprotein (GP), or one or more fragments of the Zaire ebolavirus glycoprotein (GP).

In some embodiments, the viral antigen in derived from one or more viruses from the genus Flavivirus, for example, the Zika virus (ZIKV).

Bacterial Antigens

In some embodiments, the antigen is a bacterial antigen. Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria*, Meningococcus A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio*, and *Yersinia*.

Parasite Antigens

In some embodiments, the antigen is a parasite antigen. Exemplary parasite allergens, include but are not limited to, *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

In some embodiments, the parasite antigen is one or more antigens from a protozoan, such as one or more protozoans from the genus *Toxoplasma*, for example *T. gondii* and species from a related genus, such as Ncospora, Hammondia, Frenkelia, *Isospora* and *Sarcocystis*. Exemplary antigens derived from *T. gondii* include the GRA6, ROP2A, ROP18, SAG1, SAG2A and AMA1 gene products.

Allergens and Environmental Antigens

In some embodiments, the antigen is an allergen or environmental antigen.

Exemplary allergens and environmental antigens, include but are not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens.

Important pollen allergens from trees, grasses and herbs originate from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.e. grasses of the genera *Lolium, Phleum, Poa, Cynodon, Dactylis, Holcus, Phalaris, Secale*, and Sorghum, the orders of Asterales and Urticales including i.a. herbs of the genera *Ambrosia, Artemisia*, and *Parietaria*. Other allergen antigens that may be used include allergens from house dust mites of the genus *Dermatophagoides* and *Euroglyphus*, storage mite e.g. *Lepidoglyphys, Glycyphagus* and *Tyrophagus*, those from cockroaches, midges and fleas, e.g., *Blatella, Periplaneta, Chironomus* and *Ctenocepphalides*, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

Exemplary food allergens include cow's milk (e.g., lactose), eggs, nuts, shellfish, fish, and legumes (peanuts and soybeans), fruits and vegetables such as tomatoes.

When the antigen is an allergen, the MDNPs can include one or more immuno-modulatory molecules, or one or more nucleic acids encoding immuno-modulatory molecules to direct the immune response specifically toward a Th1 (cellular) or Th2 (humoral) polarization for the delivered allergen.

Tumor Antigens

In some embodiments, the antigen is a tumor antigen. There are many classes of tumor antigens, including, but not limited to, oncogene expression products, alternatively spliced expression products, mutated gene products, overexpressed gene products, aberrantly expressed gene products, antigens produced by an oncogenic viruses, oncofetal antigens, as well as proteins with altered cell surface glycolipids, and proteins having altered glycosylation profiles.

Exemplary tumor antigens included or encoded by MDNPs include tumor-associated or tumor-specific antigens, such as, but not limited to, alpha-actinin-4, Alphafetoprotein (AFP), Bcr-Abl fusion protein, Carcinoembryonic antigen (CEA), CA-125, Casp-8, beta-catenin, cdc27, cdk4, cdkn2a, coa-1, dek-can fusion protein, epithelial tumor antigen, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARa fusion protein, PTPRK, K-ras, N-ras, Triosephosphate isomeras, Bage-1, Gage 3,4,5,6,7, GnTV, Herv-K-mel, Lage-1, Melanoma-associated antigen (MAGE); Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15 (58), CEA, RAGE, NY-ESO (LAGE), SCP-1, Hom/Mcl-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, b-Catenin, CDK4, Mum-1, p16, TAGE, PSMA, PSCA, CT7, telomerasc, 43-9F, 5T4, 791Tgp72, a-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, MUC-1, NB\70K, NY-CO-1, RCAS1, SDCCAG16, TA-90 (Mac-2 binding protein\cyclophilin C-associated protein), TAAL6, TAG72, TLP, tyrosinase, and TPS. An exemplary tumor antigen is the model melanoma tumor antigen Trp1.

In certain embodiments, the tumor antigen is the gene product of a gene that is normally expressed during embryogenesis, and whose expression in normal adult tissues is limited, such as an "oncofetal" protein, or an alternatively-spliced variant of a normal protein. Oncofetal antigens are proteins which are typically present only during fetal development but are found in adults with certain kinds of cancer. These proteins are often measurable in the blood of individuals with cancer and may be used to both diagnose and follow treatment of the tumors. Therefore, in some embodiments, the MDNPs include or encode one or more oncofetal proteins. An exemplary oncofetal protein is the Hmga2 protein.

c. Other Therapeutic or Prophylactic Agents

A non-limiting list of active agents that can be encapsulated within, or associated with the surface of the MDNPs includes antiinfectives, immunomodifying agents, hormones, antioxidants, steroids, anti-proliferative agents and diagnostic agents. Therapeutic agents can include a drug or modified form of drug such as prodrugs and analogs. In some embodiments, the MDNPs are used for the delivery of a peptide drug, a dye, an antibody, or antigen-binding fragment of an antibody.

Therapeutic Agents

In some embodiments, the MDNPs encapsulate one or more therapeutic, agents. Examples of therapeutic agents that can be associated with the MDNP include, but are not limited to, beta-lactam antibiotics (including penicillins such as ampicillin, cephalosporins selected in turn from cefuroxime, cefaclor, cephalexin, cephydroxil and cepfodoxime proxetil); tetracycline antibiotics (doxycycline and minocycline); microlides antibiotics (azithromycin, erythromycin, rapamycin and clarithromycin); fluoroquinolones (ciprofloxacin, enrofloxacin, ofloxacin, gatifloxacin, levofloxacin) norfloxacin, an antioxidant drug includes N-acetylcysteine (NAC); anti-inflammatory drugs, such as nonsteroidal drugs (e.g., indomethacin, aspirin, acetaminophen, diclofenac sodium and ibuprofen); steroidal anti-inflammatory drug (e.g., dexamethasone); antiproliferative agents (e.g., Paclitaxel (Taxol), QP-2 Vincristin, Methotrexat, Angiopeptin, Mitomycin, BCP 678, Antisense c-myc, ABT 578, Actinomycin-D, RestenASE, 1-Chlor-deoxyadenosin, PCNA Ribozym, and Celecoxib) sirolimus, everolimus and ABT-578), paclitaxel and antineoplastic agents, including alkylating agents (e.g., cyclophosphamide, mechlorethamine, chlorambucil, melphalan, carmustine, lomustine, ifosfamide, procarbazine, dacarbazine, temozolomide, altretamine, cisplatin, carboplatin and oxaliplatin), antitumor antibiotics (e.g., bleomycin, actinomycin D, mithramycin, mitomycin C, etoposide, teniposide, amsacrine, topotecan, irinotecan, doxorubicin, daunorubicin, idarubicin, epirubicin, mitoxantrone and mitoxantrone), antimetabolites (e.g., deoxycoformycin, 6-mercaptopurine, 6-thioguanine, azathioprine, 2-chlorodeoxyadenosine, hydroxyurea, methotrexate, 5-fluorouracil, capecitabine, cytosine arabinoside, azacytidine, gemcitabine, fludarabinc phosphate and aspariginasc); antimitotic agents (e.g., vincristine, vinblastine, vinorelbine, docetaxel, estramustine); molecularly targeted agents including antibodies, antibody fragments, or carbohydrates/polysaccharides (e.g., imatinib, tretinoin, bexarotene, bevacizumab, gemtuzumab ogomicin and denileukin diftitox); and corticosteroids (e.g., fluocinolone acetonide and methylprednisolonc).

Immuno-Modulatory Agents

In certain embodiments, the MDNPs encapsulate one or more immuno-modulatory molecules, or nucleic acids encoding immuno-modulatory proteins, which are generated to direct the immune response specifically toward a T-helper cell 1 (Th1; cellular) or T-helper cell 2 (Th2; humoral) polarization for a delivered antigen.

This may be to enhance functional immunity against the disease associated with the antigen by promoting the Th pathway correlated with protection, or to achieve tolerance by directing the immune response away from the Th pathway correlated with an inappropriate immune response to the antigen. Therefore, in some embodiments, MDNPs include molecules or RNAs encoding proteins that drive cellular immunity against an allergen in order to decrease the humoral response and thus treat an allergy. This principle may be applied to tolerize against self-antigens responsible for autoimmune diseases, for example, by driving a Th2 response to curtail the Th1-associated pathology of multiple sclerosis or rheumatoid arthritis. Exemplary immuno-modulatory molecules include synthetic receptor ligand or protein, cytokines or other signaling molecules.

In some instances, class-switching of B cells toward non-inflammatory antibody isotypes (i.e., immunoglobulin A (IgA) and immunoglobulin G (IgG4)), and away from the immunoglobulin E (IgE) isotype associated with allergic responses, may be desired. Therefore, in some embodiments, MDNPs enclose or encode molecules that can drive class-switching of B cells toward non-inflammatory antibody isotypes. Exemplary immune-modulatory molecules include Interleukins, such as IL-10.

4. Multiplexed Modified Dendrimer-Based Nanoparticles

In some embodiments, the MDNPs include more than one type of encapsulated agent molecule (i.e., "Multiplexed" MDNPs). For example, MDNPs can include more than one species of RNA, such as an mRNA and a repRNA. The mRNA and repRNA can encode the same or different genes. In some embodiments, multiplexed MDNPs are engineered to include more than one species of repRNA and more than one species of mRNA. The repRNAs and mRNAs can encode the same or different genes.

When an mRNA and a repRNA are enclosed within the same multiplexed MDNP, the mRNA and repRNAs can be engineered to contain complementary 5' and 3' untranslated regions (UTRs). For example, the mRNA can be modified to include UTRs that are recognized by RNA dependent RNA polymerase (RdRp) encoded by the repRNA ("modified mRNA").

When the modified mRNA and repRNA species including the same or complementary UTRs are simultaneously deposited into the cytoplasm of a host cell, the RNA dependent RNA polymerase (RdRp) encoded by the repRNA can replicate the modified mRNA through recognition of the replicon UTRs.

For this strategy, the two types of amplifiable payloads are co-delivered into the cytoplasm of cells. The addition of the modified mRNA with replicon UTRs increases the overall efficiency of the system because two amplifiable payloads are simultaneously delivered into cells, instead of one. Therefore, the repRNA can synthesize more copies of the full-length replicon, or copies of the repRNA-encoded antigen only (i.e., by virtue of a sub-genomic promoter), or more copies of the modified mRNA included within the multiplexed MDNP. The host cell ribosomes continue to translate the full-length replicon copies or the shorter antigen-only mRNAs, leading to enhanced expression of the genes encoded by the modified mRNA and repRNA (see FIG. 1B).

Therefore, in some embodiments, the MDNPs are multiplexed MDNPS that simultaneously carry two or more payload types. For example, the MDNPs can carry one or more repRNAs, and one or more mRNAs that incorporate the 5' and 3' untranslated regions (UTRs) of the replicon. The one or more repRNAs and one or more mRNAs can encode the same or different genes. In some embodiments, the MDNPs include two or more genes encoding two or more different peptide antigens.

In further embodiments, the multiplexed MDNPs can be formulated to include one or more repRNAs, and one or more mRNAs that incorporate the 5' and 3' untranslated regions (UTRs) of the replicon additional nucleic acid and optionally one or more additional active agents, such as a functional nucleic acid, protein or small molecule.

In some embodiments, a multiplexed MDNP is formulated to include one or more repRNAs encoding more than one protozoan antigen. In an exemplary embodiment, a multiplexed MDNP encodes the GRA6, ROP2A, ROP18, SAG1, SAG2A and AMA1 gene products of *T. gondii*.

In some embodiments, a multiplexed MDNP is formulated to include two or more viral antigens derived from one or more viruses from the Orthomyxovirus family, for example, Influenza virus A, Influenza virus B, and Influenza virus C. In an exemplary embodiment, multiplexed MDNPs include RNA encoding two or more antigens from the same or different influenza A virus subtypes, including seasonal and pandemic influenza virus strains. For example, in some embodiments, multiplexed MDNPs include two or more antigens from one or more of the H1N1, H1N2, H3N2, H3N1, H5N1, H2N2, and H7N7 subtypes. In some embodiments, multiplexed MDNPs include two or more proteins or glycoproteins derived from one or more of the H1N1, H1N2, H3N2, H3N1, H5N1, H2N2, and H7N7 influenza virus subtypes, such as the HA1 subunit of hemagglutinin, the HA2 subunit of hemagglutinin, neuraminidase, viral RNA polymerase, such as one or more of PB1, PB2 PA and PB1-F2, reverse transcriptase, capsid protein, non-structured proteins, such as NS1 and NEP, nucleoprotein, matrix proteins, such as M1 and M2 and pore proteins. In some embodiments, multiplexed MDNPs include two or more HA antigens from two or more of the H1N1, H1N2, H3N2, H3N1, H5N1, H2N2, and H7N7 influenza subtypes.

B. Excipients, Delivery Vehicles and Devices

MDNPs can be formulated into compositions including suitable excipient for administering the nanoparticles into the body of a subject.

In certain embodiments, MDNPs are formulated in a carrier or excipient suitable for delivery into a subject by injection, for example, via intramuscular (i.m.) intravenous (i.v.), subcutaneous (s.c.), intraperitoneal (i.p.), or via skin scarification. Typical carriers are saline, phosphate buffered saline, glucose solutions, and other injectable carriers.

Therefore, formulations including MDNPs with or without delivery vehicles are described. The MDNPs can be formulated into pharmaceutical compositions including one or more pharmaceutically acceptable carriers. Pharmaceutical compositions can be formulated for different mechanisms of administration, according to the desired purpose of the MDNPs and the intended use. Pharmaceutical compositions formulated for administration by parenteral (intramuscular, intraperitoneal, intravenous (IV), intraocular or subcutaneous injection), topical or transdermal (either passively or using iontophoresis or electroporation) routes of administration or using bioerodible inserts are described.

1. Parenteral Administration

In some embodiments, MDNPs are formulated for administration in an aqueous solution, by parenteral injection. The formulation may also be in the form of a suspension or emulsion. In general, pharmaceutical compositions are provided including effective amounts of an active agent, targeting moiety, and optional a delivery vehicle and optionally include pharmaceutically acceptable diluents, preservatives, solubilizers, emulsifiers, and/or carriers. Such compositions include the diluents sterile water, buffered saline of various buffer content (e.g., Tris-HCl, acetate, phosphate), pH and ionic strength and optionally additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Pulmonary, Topical and Mucosal Administration

Compositions of MDNPs can be formulated for application topically, by instillation or by inhalation. In some embodiments, MDNPs are formulated for administration to the mucosa, such as the lungs, mouth, eyes, lungs, nasal, oral (sublingual, buccal), vaginal, or rectal mucosa. Formulations for administration to the mucosa will typically be spray dried drug particles, which may be incorporated into a tablet, gel, capsule, suspension or emulsion. Standard pharmaceutical excipients are available from any formulator.

In some embodiments, the MDNPs are formulated for delivery to the skin, for example, by direct application to the surface of diseased, or damaged or ruptured skin. Therefore, in some embodiments, MDNPs are formulated for delivery to a wound or site of surgery. Compositions formulated for topical delivery can include one or more penetration enhancers.

In one embodiment, the MDNPs are formulated for pulmonary delivery, such as intranasal administration or oral inhalation. The respiratory tract is the structure involved in the exchange of gases between the atmosphere and the blood stream. The upper and lower airways are called the conducting airways. The terminal bronchioli divide into respiratory bronchiole, which then lead to the ultimate respiratory zone, the alveoli, or deep lung. The deep lung, or alveoli, is the primary target of inhaled therapeutic aerosols for systemic drug delivery. Therapeutic agents that are active in the lungs can be administered systemically and targeted via pulmonary absorption. The term aerosol refers to any preparation of a fine mist of particles, which can be in solution or a suspension, whether or not it is produced using a propellant. Aerosols can be produced using standard techniques, such as ultra-sonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. One skilled in the art can readily determine a suitable saline content and pH for an innocuous aqueous solution for nasal and/or upper respiratory administration.

Compositions can be delivered to the lungs while inhaling and traverse across the lung epithelial lining to the blood stream when delivered either as an aerosol or spray dried particles having an aerodynamic diameter of less than about 5 microns.

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits. A wide range of mechanical devices designed for pulmonary delivery of therapeutic products can be used, including, but not limited to, nebulizers, metered dose inhalers, and powder inhalers, all of which are familiar to those skilled in the art.

Iii. Methods for Making Modified Dendrimer-Based Nanoparticles

Methods for the production of the MDNPs are provided. Typically, the methods include combining akylated dendrimers with one or more amphiphilic polymers in the presence of one or more therapeutic, prophylactic and diagnostic agents.

Methods for the production the MDNPs containing encapsulated agent, such as repRNA, are described. The methods can be used, for example, for the packaging of large repRNAs into MDNPs.

Generally, methods of making MDNPs do not impose any limitation on the structure of the encapsulated agent that is to be packaged within the MDNPs. For example, nucleic acids enclosed within MDNP can be long or short, single-stranded or double-stranded, and can be of any sequence. The purification of MDNPs containing therapeutic, prophylactic and diagnostic agents produced by the described methods is trivial, and can be simpler than the purification of unpackaged cargo.

When nucleic acids are enclosed with MDNPs, the nucleic acids can be at least 80% pure. In other embodiments the nucleic acid is at least 85% pure, at least 90% pure or at least 95% pure. Typically one MDNP contains at least one molecule of the nucleic acid.

In one embodiment, RNA is packaged within the MDNPs at a modified dendrimer/RNA molar ratio of about 5:1.

A. Assembly of Modified Dendrimer-Based Nanoparticles

Generally, the MDNPs are formulated by mixing of the ionizable dendrimer, hydrophilic-anchored polymer and therapeutic, prophylactic and diagnostic agents. Mixing can be carried out by any suitable means known in the art, such as using a microfluidic mixing (Khan, et al., *Nano Lett*, doi:10.1021/n15048972 (2015); Khan, et al., *Angewandte Chemie* 53, 14397-14401, doi:10.102/anie.201408221 (2014)).

Modified dendrimers and amphiphilic polymers can be combined using a suitable solvent, such as ethanol. When RNA molecules are included within MDNPs as cargo, the RNA can be diluted in a low-pH buffer, such as Citrate Buffer (pH 2-4).

B. Purification of MDNPs

Because of their distinctive size, properties and high stability, MDNPs can be easily purified from substrates following assembly. The purification of MDNPs containing range of therapeutic, prophylactic and diagnostic agents produced by the described methods is straightforward, and can be carried out using standard methods known in the art, such fast protein liquid chromatography (FPLC), filtration, sedimentation, sucrose-gradient separation, affinity tag chromatography and flow-field fractionation multi-angle light scattering (FFF-MALS). In some embodiments, the nanoparticles can be purified by filtration, for example, using 0.2 micron poly(ether sulfone) filters.

The purified nanoparticles can be characterized using any technique known in the art, such as light scattering.

In some embodiments, the particles can be characterized and/or isolated on the basis of the electro-kinetic potential, or Zeta potential of the mature particles. Zeta potential is a measure of the magnitude of the electrostatic or charge repulsion/attraction between particles. The Zeta potential of fully formed particles in PBS can range from approximately −2 mV to approximately −25 mV, inclusive, for example, −5 mV to −20 mV. Methods to measure the Zeta potential of the particles and isolate particles on the basis of Zeta potential are known in the art.

In some embodiments, the particles can be characterized and/or isolated on the basis of the molecular weight and/or hydrodynamic volume of the mature particles. Depending on generation size used in formulating the core of the particles, the molecular weight of fully formed particles can range from approximately 2,000 Da to approximately 80,000 Da, inclusive. Methods to measure the molecular weight of the particles and isolate particles on the basis of molecular weight are known in the art.

MDNPs can be formulated to contain different mass ratios of modified dendrimer to hydrophobic-anchored polymers. Typically the MDNPs include a greater mass of modified dendrimer than hydrophobic-anchored polymers. For example, MDNPs can be formulated to include a mass ratio of modified dendrimer to hydrophobic-anchored polymer of between 2:1 and 20:1, such as 5:1, 6:1, 7:1, 8:1, 9:1, 10:1, 11:1, 12:1, 13:1, 14:1, 15:1 or greater than 15:1. In a certain embodiment, MDNPs have a 11.5:1 mass ratio of modified dendrimer to hydrophobic-anchored polymer. The final concentration of therapeutic, prophylactic and diagnostic agents encapsulated within the MDNPs can be determined by theoretical mass balance calculations. Typically, the MDNPs include a greater mass of modified dendrimer than therapeutic, prophylactic and diagnostic agents. For example, MDNPs can be formulated to include a mass ratios of modified dendrimer to therapeutic, prophylactic and diagnostic agents of between 2:1 and 10:1, such as 3:1, 4:1, 5:1, 6:1, 7:1, 8:1, 9:1, 10:1, or greater than 10:1. In a certain embodiment, where the encapsulated agent includes RNA, the MDNPs have a 5:1 mass ratio of modified dendrimer to RNA.

In some embodiments, where the encapsulated agent includes DNA and/or mRNA, the MDNPs have a mass ratio of modified dendrimer to RNA ranging between 2:1 and 10:1 inclusive.

IV. Methods of Use

Methods of using the MDNPs are provided. It has been established that MDNPs provide an effective, biocompatible and non-toxic vehicle for the delivery of encapsulated agent including large nucleic acids and/or polypeptides to the cells of a subject. The MDNPs are also non-immunogenic and can persist in the serum of a subject for an extended period of time, such as for 1 day, 2 days, 3 days, 4 days, 5 days, 6 days, 7 days, several weeks or several months. For example, the MDNPs can be designed to avoid host immune surveillance to enhance the serum half-life of the MDNPs leading to internalization within the phagosome and/or lysososmal compartments of the non-phagocytic cell types.

The MDNPs are readily taken up by many cell types and efficiently deliver enclosed therapeutic, prophylactic and diagnostic agents to biological targets. For example, when MDNPs are trans-located into the cytoplasm of the host cell, the nucleic acid, small molecule and protein encapsulated agents can be deposited into the cytoplasmic space. When encapsulated agents include exogenous genes, the genes can be expressed in the host cell, giving rise to biological effector functions, such as immune modulation.

Therefore, methods of using MDNPs can include administering to a subject an effective amount of a composition including MDNPs to deliver one or more exogenous genes or polypeptides to the cells of the subject. Typically, the cells are not professional antigen-presenting cells.

MDNPs can induce a biological effect in the cells of the recipient, such as an immune-modulatory effect. For example, MDNPs can be used to stimulate an immune response to a desired antigen in the subject. In some embodiments, the MDNPs are safe and effective delivery vehicles for RNA neo-antigens that serve as an immunogens for eliciting an immune response against a disease.

Methods to prevent, reduce, or inhibit the expression or function of a target gene in a subject are also provided.

A. Methods of Delivering Nucleic Acids and Polypeptides

It has been established that MDNPs can provide effective delivery of nucleic acid therapeutic, prophylactic and diagnostic agents, including large repRNAs, to the interior of cells, leading to enhanced expression of exogenous genes in target cells. Typically, the expression of genes encoded by repRNA is greater in the subject when the repRNA is delivered within MDNPs than when RNA is delivered alone. For example, delivery of repRNAs encoding one or more exogenous genes encapsulated within MDNPs to cells can enhance the translation of exogenous mRNA sequences within the cells and maintain prolonged expression of exogenous peptides, as compared to administration of equal amounts of the pure repRNA alone, or as compared to the delivery of non-replicating mRNAs encapsulated within MDNPs to the cells.

The MDNPs protect nucleic acids from degradation until the particles are internalized into the host cell. It may be that MDNPs are internalized into the cell by generalized endocytosis. The MDNPs can deliver exogenous nucleic acids and polypeptides to eukaryote cells in vivo or in vitro. Typically, the delivery requires contact and internalization of the MDNPs by the target cells. Internalization can occur through one or more different mechanisms. The contacting between the MDNPs and target cells can be induced occur in vivo or in vitro. Generally, the contacting occurs in vivo.

Therefore, in some embodiments, the MDNPs are administered to a subject. In some embodiments, the MDNPs are directly administered to a specific bodily location of the subject. In further embodiments, the route of administration targets the MDNPs directly to a specific organ.

Pharmaceutical compositions including MDNPs can be administered in a variety of manners, depending on whether local or systemic administration is desired, and depending on the area to be treated. Injectable formulations can be prepared in conventional forms, either as liquid solutions or suspensions, solid forms suitable for solution of suspension in liquid prior to injection, or as emulsions. In certain embodiments, the compositions are administered locally, for example, by injection directly into a site to be treated. In some embodiments, local delivery can reduce side effects or toxicity associated with systemic delivery and can result in enhanced outcome due to an increased localized dose.

The compositions can be injected or otherwise administered directly to one or more surgical sites. Typically, local injection causes an increased localized concentration of the MDNP compositions which is greater than that which can be achieved by systemic administration.

In some embodiments, systemically administered MDNPs persist in the blood stream and release the encapsulated agent to target cells over a period of time. Preferably, the steady release maintains a desired concentration of exogenous nucleic acids or polypeptides in the target cells.

Compositions of MDNPs can be administered during a period before, during, or after onset of symptoms of a disease, or any combination of periods before, during or after onset of one or more disease symptoms. For example, the subject can be administered one or more doses of the composition every 1, 2, 3, 4, 5, 6 7, 14, 21, 28, 35, or 48 days prior to the onset of disease symptoms, (i.e., prior to the predicted onset). The subject can be administered one or more doses of the composition every 1, 2, 3, 4, 5, 6, 7, 14, 21, 28, 35, or 48 days after the onset of disease symptoms. In some embodiments, the multiple doses of the compositions are administered before an improvement in disease condition is evident. For example, in some embodiments, the subject receives 1, 2, 3, 4, 5, 6 7, 14, 21, 28, 35, or 48 doses over a period of 1, 2, 3, 4, 5, 6 7, 14, 21, 28, 35, or 48 days or weeks before an improvement in the disease or condition is evident.

Thus, compositions including one or more MDNPs can be administered at different times in relation to a diagnosis, prognosis, surgery or injury depending on the desired effects of the nucleic acids or polypeptides that are delivered to the target cells. The timing of commencement of administration of the MDNPs should be determined based upon the needs of the subject, and can vary accordingly.

In some embodiments, a single dose of MDNPs is delivered to a subject as one or more bolus doses to raise the blood concentration of the MDNPs, or the blood concentration of the payload of the MDNPs to a desired level. The bolus can be given by any means, such as via injection. The placement of the bolus dose can be varied depending upon the desired effect and the target organ or tissue to be treated. In a particular embodiment, a bolus is given prior to the administration of other dosage forms.

For example, the MDNPs can be engineered to impart different residency times in the blood stream, for example, by modification of one or more of targeting moieties, pegylation, polymer surface density, etc. Thus, the desired blood concentration of MDNPs can be maintained for a desired period of time using a combination of formulations, administered at the same time, or as a series of administrations over a period of time, as desired.

B. Vaccination

In some embodiments, MDNPs can deliver exogenous proteins and/or nucleic acids to a subject to stimulate desired immune responses in the subject. The delivery of antigen via the MDNPs confers protective immunity to infectious agents such as viruses and bacteria. The non-immunogenic nature of the modified dendrimers, even at doses 50 times higher than those that protect against Ebola challenge (Khan, et al. *Nano Lett*, doi:10.1021/nl5048972 (2015); Khan, et al. *Angewandte Chemie* 53, 14397-14401 (2014)) is a property that favors efficient transgene expression, as any stimulation of innate immunity is due to the expression of the mRNA payload only.

Methods for vaccination using large, self-amplifying RNA replicons enclosed within MDNPs are provided which allow potent and persistent presentation of antigen to the immune system without stimulating IFN responses early upon injection. A strong IFN response would likely impede alphaviral replication and thus limit antigen dose over time. (Zhang, et al., J Virol 81, 11246-11255, (2007); White, et al., *J Virol* 75, 3706-3718 (2001)).

Experiments conducted with the MDNPs including repRNAs encoding the OVA peptide, HA antigen and EBOV GP antigen peptides (discussed below), demonstrate that MDNPs can deliver repRNAs to cells to generate a strong immune response against a range of viruses, and also against the OVA peptide.

Other proteins could be substituted for these peptides. These could include proteins from pathogenic microbes such as viruses, bacteria, fungi, protozoa, as well as cancer antigens. Therefore, the MDNPs can serve as a safe and effective platform for the delivery vaccine agents, such as RNA-encoded antigens and neo-antigens, targeting many different pathogenic microbes.

Typically, MDNP-mediated delivery of exogenous antigen to the cells of a subject results in the production of antibodies and other biomolecules capable of recognizing and neutralizing the antigen. Antigen that has been arrayed on the surface of antigen-presenting cells (APC) can be presented to a "helper" T cell, such as an antigen-specific naive CD4+ T cell. Such presentation delivers a signal via the T cell receptor (TCR) that directs the T cell to initiate an immune response that will be specific to the presented.

Therefore, the MDNPs can be used to initiate, moderate or enhance a humoral and/or cellular immunity to an encoded antigen. For example, the MDNPs deliver exogenous nucleic acids and/or proteins in an amount effective to induce, enhance or otherwise moderate the biological activities of immune cells, such as macrophages, B-cells, T-cells, dendritic cells and NK cells.

In some embodiments, administration of the MDNPs including nucleic acid sequences encoding an antigen to a subject confers immunity to the antigen to the subject. Immunity can manifest in the production of a reservoir of memory T cells (i.e., memory CD8+ T cells) and/or antigen-specific B cells in the subject sufficient to provide rapid immune cellular and/or humoral immune responses to repeat exposure of the antigen. Preferably, administration of the MDNPs including nucleic acid sequences encoding an antigen confers protection against infection or disease caused by the organism(s) from which the antigen is derived.

Typically, administration of the MDNPs including nucleic acid sequences encoding an antigen to a subject enhances the uptake and delivery of antigen to the antigen presenting cells of the subject relative to administration of equal amounts of the antigen or nucleic acid encoding the antigen alone. Therefore, administration of antigen to a subject via the MDNPs can enhance the immune response to the antigen in the subject relative to administration of equal amounts of the antigen or nucleic acid encoding the antigen alone. For example, MDNPs can increase, prolong or otherwise enhance presentation of the encoded antigen at the surface of antigen presenting cells of the subject.

Vaccines can be administered prophylactically or therapeutically. Vaccines can also be administered according to a vaccine schedule. A vaccine schedule is a series of vaccinations, including the timing of all doses. Many vaccines require multiple doses for maximum effectiveness, either to produce sufficient initial immune response or to boost response that fades over time. Vaccine schedules are known in the art, and are designed to achieve maximum effectiveness. The adaptive immune response to one or more antigen delivered in the MDNPs can be monitored using methods known in the art to measure the effectiveness of the vaccination protocol.

In some embodiments, MDNPs deliver exogenous proteins and/or nucleic acids to a subject and stimulate immune responses specifically to antigen that is expressed and biologically-processed by the host cells. Therefore, methods for vaccination using nucleic acids encoding antigens deliver by the MDNPs can provide immunity to antigen including post-translational modifications specific to the host subject. For example, vaccination using nucleic acids encoding antigen delivered by the MDNPs can provide immunity to proteins containing post-translational modifications native to the host, such as glycosylation, lipidation (including myristoylation, palmitoylation, isoprenylation), sulfation, oxidation, phosphorylation, adenylation, methylation and amidation. The immune responses generated by a subject to these post-translationally-modified peptide antigens can be the same or different to immune responses raised in the same host against the non-natively expressed or post-translationally modified form of the same antigenic peptide.

1. Vaccination Strategies for Multiple repRNAs

As described above, MDNPs can include two or more different repRNAs. The two or more different repRNAs can be engineered to express the same or different exogenous immunogenic antigens.

In some embodiments, nanoparticle vaccines include combinations of different species of RNAs, such as mRNAs and repRNAs, each with different antigen production kinetics. By "multiplexing" RNAs with different kinetics, MDNP/RNA vaccines can engineered to express one or more antigens at different times following administration. The multiplexed MDNP/RNA vaccines can include a mixture of distinct MDNPs, each enclosing different RNA species, or alternatively each MDNP can be engineered to include more than one RNA species.

When MDNPs are engineered to include one species of RNA, such as a single species of repRNA encoding a single antigen, vaccines can be designed by mixing a desired amount of each MDNP to create a combined MDNP vaccine, having the desired expression kinetics.

Due to the finite persistence of RNA encoding exogenous antigens in the cells of a subject, MDNP-based RNA vaccines are self-limiting and only produce antigens for a finite amount of time until the host eliminates the RNA and all vaccine products ale cleared by the body. Antigen production occurs in host cell cytoplasm, and the genetic material in the nucleus of the cell is never manipulated. The inherent self-amplification of repRNAs enables small increases in vaccine dose to result in a non-linear increase in antigen production. Therefore, in some embodiments, MDNPs including two or more different repRNAs expressing the same antigen can be used to induce expression of the antigen in the cells of a recipient with different expression kinetics. For example, the delivery of two or more different repRNAs expressing the same antigen can give rise to a different serum half-life of the expression product. For example, the repRNAs can induce expression of the same antigen at a different rate within the recipient cells. Therefore, when different repRNAs give rise to expression of the same antigen at different rates, the total serum half-life of the antigen can be extended relative to that when only one of the species of repRNA is delivered.

In some embodiments, the encapsulated agent of MDNPs is engineered to include more than one RNA species, to provide expression of antigens over prolonged or defined periods of time following administration. For example, MDNPs can include mRNA and one or more repRNAs encoding the same or different antigens to provide distinct and different expression kinetics for the antigen(s) within a subject.

In some embodiments, the MDNPs deliver cargo, such as RNA neo-antigens, to a subject to provide two or more distinct phases of expression of the antigen in the subject. For example, mRNAs and/or repRNAs encoding an antigen can give rise to a first "expression phase" of an antigen associated with translation of one RNA species, leading to an increase in serum concentration of the antigen. As antigen expression diminishes, and antigen serum concentration decreases, a second "expression phase" of the same or different antigen, associated with translation of a second RNA species, leads to a subsequent increase in serum concentration of antigen. Therefore, when MDNPs including two or more different repRNAs expressing antigen are used for vaccination, it can be desirable to engineer MDNP therapeutic, prophylactic and diagnostic agents to provide a primary (i.e., "prime") increase in the serum concentration of the antigen(s), followed by a secondary or further subsequent (i.e., "boost") increases in the serum concentration of the antigen(s), based on only a single administration of the MDNP vaccine. For example, MDNPs enclosing more than one repRNA can provide "Self-boosting" vaccines (see FIGS. 10A-10B).

The selection of repRNA genomes can influence the expression of antigens encoded by the repRNA. For example, the serum concentration of an antigen at a given time point following administration of MDNP/repRNA vaccines can be correlated with a specific repRNA genotype (see FIGS. 5A-5G and FIGS. 6A-6G).

Modifications to the nucleic acid sequence of a repRNA associated with changes in the expression of encoded gene products can be used to assist in the design of modified repRNAs engineered to provide desired expression kinetics. In some embodiments, repRNAs are designed for including within multiplexed vaccines, based on determination of a serum concentration and serum half-life for a specific antigen or group antigens.

Therefore, repRNAs having different expression kinetics of encoded antigens for including within "self-boosting" MDNP-mediated vaccines can be developed by altering the nucleic acid sequences of the repRNA. For example, when an alphavirus-derived repRNA is used to deliver an exogenous antigen in host cells, alteration of one or more of the non-structural proteins of the repRNA can be carried out to impact the expression of exogenous genes encoded by the repRNA.

In other embodiments, the MDNP vehicles can be designed to enter cells and deliver therapeutic, prophylactic and diagnostic agents at a certain rate, for example, by modification of the composition of the MDNP to alter the serum half-life of the MDNP in vivo.

In further embodiments, MDNP are delivered to more than one bodily locations, for example by the same or different administration routes, leading to different serum half-life and cellular-uptake kinetics of the MDNP and subsequent differences in the location and rate of antigen expression.

In some embodiments, when MDNPs are used to deliver repRNAs to express antigen in the cells of a subject, a smaller molar amount of the repRNA is required to produce the same antigen-specific immune response in the subject as compared to the molar amount of mRNA delivered by MDNPs to produce the same antigen-specific immune response. Generally, a smaller amount of MDNPs including repRNA can be required to produce an antigen-specific immune response in a subject as compared to the amount of MDNPs including protein antigen or mRNA encoding the same antigen. Therefore, MDNPs including repRNA can be used to induce an antigen-specific immune response in a subject that reduces any undesirable effects associated with the introduction the MDNPs into a subject.

Methods for screening of different vaccine agents delivered by the MDNPs are also provided. Typically the methods included vaccinating a subject with MDNPs including one or more distinct antigens or nucleic acids encoding antigens and assessing the immune response in the subject. The adaptive immune response to one or more antigen delivered in the MDNPs can be monitored using methods known in the art to measure the effectiveness of the vaccination protocol. For example, the duration and extent of antigen-specific T-cell activation can be used as a marker for antigen expression kinetics. Antigen-serum concentration can also be used to determine antigen-expression kinetics.

The results can be compared to a control, such as a subject vaccinated with a different antigen or combination of antigens using the same or different delivery vehicles, same or different protocol, vaccination schedule or administration. In some embodiments, a suitable control is an unvaccinated subject.

2. Pathogens/Diseases to be Vaccinated Against

MDNPs can deliver protein and nucleic acid antigen to a subject in an amount effective to vaccinate the subject from one or more diseases and disorders. The MDNPs can serve as a vaccination platform for a wide variety of microbial pathogens, such as bacterial, viral, fungal and protozoan pathogens.

In some embodiments, the target of the vaccine could be a type of cancer cell as a cancer treatment. Alternately, the target could be any of a large number of microbial pathogens. Exemplary diseases that can be vaccinated against include disease for which vaccines are currently available. Alternatively or in addition, MDNPs can serve as a platform for inducing immunological tolerance to a subject to one or more allergens, such as food allergens and environmental allergens.

a. Cancer

In certain embodiments, MDNPs can be used to immunize a subject against cancer. The MDNPs can be administered to a subject diagnosed with cancer (i.e., as a therapeutic vaccine), or to a subject having a predisposition or risk of developing cancer (i.e., as a prophylactic vaccine). In some embodiments, the compositions of MDNPs are administered to a cancer patient in addition to one or more additional therapeutic agents.

To create an ideal cancer therapy, bioinformatics is used to sequence each patient's unique tumor exome to identify neoantigens. Then, corresponding mRNAs of these neoantigens are used to generate the antigens necessary to create immunity. Finally, these mRNAs are delivered using an adjuvant-free nanotechnology delivery platform capable of activating both the cytotoxic T cell and humoral arms of the immune system in order to create durable and long-term protection against new tumor growth and metastases.

In some embodiments, the MDNPs include one or more tumor antigens or one or more nucleic acids expressing a tumor antigen. The MDNPs can be used to provide immunity and therapeutic activity against tumor cells and non-tumor cells located within a tumor or a tumor environment. MDNPs can be formulated to provide protective and/or therapeutic activity against solid tumors and cancers of the blood. Exemplary tumor cells include, but are not limited to, tumor cells of cancers, including leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease, non-Hodgkin's disease; multiple myelomas such as, but not limited to, smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer such as but not limited to papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers including, but not limited to, Cushing's disease, prolactin-secreting tumor, acromegaly, and diabetes insipius; eye cancers including, but not limited to, ocular melanoma such as iris melanoma, choroidal melanoma, and ciliary body melanoma, and retinoblastoma; vaginal cancers, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including, but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. Cancers that can be prevented, treated or otherwise diminished by the MDNPs include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, papillary adenocarcinomas, and gastric cancer (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America). In some embodiments, MDNPs can be used to immunize a subject against one or more cancers for which no alternative vaccine is available.

b. Infectious Diseases

MDNPs can deliver antigens to the APC of a subject in an amount effective to vaccinate the subject from one or more infectious diseases caused by a wide variety of microbial pathogens, such as bacterial, viral, fungal and protozoan pathogens.

In some embodiments, the target of the vaccine could be any of a large number of microbial pathogens. Exemplary diseases that can be vaccinated against include disease for which vaccines are currently available, including Anthrax; Diseases (e.g., cervical cancer, cancer of the esophagus) caused by Human Papillomavirus (HPV); Diphtheria; Hepatitis A; Hepatitis B; Haemophilus influenzae type b (Hib); Influenza viruses (Flu); Japanese encephalitis (JE); Lyme disease; Measles; Meningococcal; Monkeypox; Mumps; Pertussis; Pneumococcal; Polio; Rabies; Rotavirus; Rubella; Shingles (Herpes Zoster); Smallpox; Tetanus; Toxoplasmosis; Typhoid; Tuberculosis (TB); Varicella (Chickenpox); Yellow Fever.

In some embodiments, MDNP can be used to immunize a subject against an infectious disease or pathogen for which no alternative vaccine is available, such as diseases including, but not limited to, malaria, streptococcus, Ebola Zaire, HIV, Herpes virus, hepatitis C, Middle East Respiratory Syndrome (MERS), Sleeping sickness, Severe Acute Respiratory Syndrome (SARS), rhinovirus, chicken pox, hendra, NIPA virus, Zika Virus, and others.

In some embodiments, the disease is a pathogen that infects non-mammalian subjects, such as birds. Exemplary avian subjects include domesticated birds (i.e., poultry), such as chickens, ducks, geese, pheasants and other commercial fowl, or pet birds such as parakeets and parrots. For example, bacterial hybrid vectors can be useful to vaccinate birds against Infectious Bursal Disease (IBD). IBD, also known as Gumboro disease, a viral disease affecting the Bursa of Fabricius of young chickens. Other diseases and disorders of poultry that can be vaccinated for using the described bacterial hybrid vectors include Influenza, Ranikhet; Mareks disease, fowl pox, fowl cholera, egg drope syndrome, infectious coryza, coccidiosis, avian encephalitis, avian influenza, chicken infectious anemia and salmonella.

c. Allergies

In certain embodiments, MDNPs can be used to immunize a subject against an allergen. The MDNPs can be administered to a subject diagnosed with an allergy or to a subject having a predisposition to an allergy. In some embodiments, the compositions of MDNPs are administered to a patient having an allergy in addition to one or more additional therapeutic agents.

Allergies are abnormal reactions of the immune system that occur in response to otherwise harmless substances. An allergy is a type of immune reaction in which the immune system responds to foreign microorganisms or particles by producing specific antibodies capable of binding to allergens such as pollen, dust, animal hairs, etc. Allergic reactions that can be treated include delayed hypersensitivity reactions and immediate hypersensitivity reactions.

Allergies that can be treated include allergic responses in the skin, such as dermatitis, the upper airways and eyes, such as allergic rhinitis, hay fever, asthma, and conjunctivitis (pink eye) in the gastrointestinal tract, such as food allergies, and blood stream, such as urticaria and hives, angioedema, anaphylaxis, or atopic dermatitis.

C. Gene Targeting

MDNPs can be used in gene targeting strategies for the delivery of RNAs that have interfering activity (iRNA) against a specific target gene within a specific target organism. In some embodiments, the iRNA can induce sequence-specific silencing of the expression or translation of the target polynucleotide, thereby down-regulating or preventing gene expression. For example, MDNPs can be used to deliver iRNA to induce the complete lack of expression of the target gene. In some embodiments, the iRNA can reduce the level of expression of the target gene below that of an untreated control.

In some embodiments, MDNPs are used to deliver RNA is a double-stranded small interfering RNA (siRNA) polynucleotides. Typically, small interfering RNAs are between 21 and 23 nucleotides in length. The siRNAs can be expressed within the host cell.

In other embodiments MDNPs are used to deliver micro RNA (miRNA) polynucleotides. miRNA is a small RNA that adopts a hairpin conformation. The miRNA can be cleaved into biologically active dsRNA within the target cell by the activity of the endogenous cellular enzymes, for example the enzyme Dicer and Dicer-like enzymes. In other embodiments the RNA polynucleotide is a long double stranded RNA molecule (dsRNA) that is at least 24 nucleotides in length. The dsRNA is processed into a biologically active siRNA of 21-23 nucleotides by the activity of the endogenous cellular enzymes, for example the enzyme Dicer and Dicer-like enzymes within the target organism. The dsRNA contains a nucleotide sequence that is complimentary to one or more genes that are to be targeted for down-regulation.

The one or more target genes can be of any desired sequence. In some embodiments, the sequence of the RNA is 100% complementary to the sequence of the target gene. In other embodiments the RNA is less than 100% complementary to the target gene. In certain embodiments, the RNA is at least 95%, at least 90%, at least 85% or at least 80% complementary to the nucleotide sequence of the target gene, so that sequence variations that can occur, for example due to genetic mutation, evolutionary divergence and strain polymorphism can be tolerated.

In some embodiments, the MDNPs can be used in gene targeting strategies. For example, MDNPs can be used to deliver an agent that induces a single or a double strand break in the target cell's genome. An exemplary system for induces a single or a double strand break in the target cell's genome is a CRISPR/Cas system. CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, *Science,* 15: 339 (6121): 819-823 (2013) and Jinek, et al., *Science,* 337 (6096): 816-21 (2012)). By transfecting a cell with the required elements including a Cas gene and specifically designed CRISPRs, the organism's genome can be cut and modified at any desired location.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA: tracrRNA duplex as described in Cong, *Science,* 15: 339 (6121): 819-823 (2013) and Jinek, et al., *Science,* 337 (6096): 816-21 (2012)). A single fused crRNA-tracrRNA construct can also be referred to as a guide RNA or gRNA (or single-guide RNA (sgRNA)). Within an sgRNA, the crRNA portion can be identified as the 'target sequence' and the tracrRNA is often referred to as the 'scaffold'. Therefore, in some embodiments, the MDNPs are used to deliver sgRNA.

D. Delivery of Additional Active Agents

In some embodiments, the MDNPs are used for the delivery of additional active agents, such as small molecule therapeutic agents, into the cells of a subject for the treatment of a disease or disorder. In certain embodiments, the MDNPs are used to selectively target one or more specific cell type of a subject for the delivery of therapeutic, prophylactic and diagnostic agents to that cell type.

Therefore in some embodiments, MDNPs can provide an effective therapeutic strategy against infectious disease, cancer, inflammatory disease, etc.

E. Dosages and Effective Amounts

In some in vivo approaches, the compositions of MDNPs are administered to a subject in a therapeutically effective amount. The term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease or disorder, and the treatment being effected.

For all of the compounds described, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired.

Generally dosage levels of between 0.001 and 100 mg/kg of body weight daily are administered to subjects such as mammals, most preferably, humans. Generally, for intravenous injection or infusion, dosage may be lower. Preferably, the compositions are formulated to achieve a modified prokaryotic cell serum level of between about 1 and about 1000 μM.

For example, MDNPs can be in an amount effective to deliver antigen to a subject and induce the proliferation and clonal expansion of B cells, T cells or induce the migratory or chemotactic activity of macrophages. Therefore, In some embodiments, the MDNPs including encapsulated agent are in an amount effective to stimulate a primary immune response to an antigen in a subject. In a preferred embodiment the effective amount of MDNPs does not induce significant cytotoxicity in the cells of a subject compared to an untreated control subject. Preferably, the amount of MDNPs is effective to prevent or reduce the infection or onset of a disease or disorder in a subject compared to an untreated control.

In another embodiment, the MDNPs are in an amount effective to decrease the amount of expression of a target gene, or to prevent or decrease the serum concentration of a target gene product in a subject.

In a particular embodiment, MDNPs are in an amount effective to induce presentation of an antigen by antigen-presenting cells. For example, MDNPs can be in an amount effective to induce T cell activation in response to an exogenous polypeptide encoded by a gene delivered to the cells of a subject by the MDNPs. In a further embodiment, the one or more MDNPs are in an amount effective to decrease the amount of antigen required to stimulate a robust or protective immune response to the antigen in a subject. The MDNPs can be effective to induce the production or antibodies to an antigen encoded by the MDNPs.

Thus, the MDNPs can be effective to enhance the amount of antigen-specific immune cells in a subject. For example the amount of antigen-specific immune cells in a subject can be increased relative to the amount in an untreated control. For example, MDNPs can be effective to induce several signaling pathways controlling cellular immune activities, including cellular proliferation, chemotaxis and actin reorganization. Preferably the effective amount of MDNPs does not cause cytotoxicity. The effective amount of MDNPs to provide adaptive immunity to an encoded antigen or allergen should not generate a significant systemic increase in inflammatory cytokine production, including IFN.

In some embodiments, MDNP can be used to immunize a subject against a cancer, an infectious disease or an allergen using only a single dose. Therefore, in some embodiments, only a single administration is required with no boosting. In other embodiments, enhanced or prolonged immunity, such as protective immunity, is achieved when one or more additional doses are used to boost the immune response to a first or previous administration.

Typically, the absence of a cytokine response to the nanoparticle delivery vehicles in vivo precludes the development of anti-vector immunity. Therefore, in some embodiments, administration of MDNPs can be carried out repeatedly using the same or different doses of MDNPs containing the same or different RNAs encoding antigens, for example, to provide immunity to a variety of different antigens or allergens in the same subject.

F. Controls

The effect of MDNPs can be compared to a control. Suitable controls are known in the art and include, for example, untreated cells or an untreated subject. In some embodiments, the control is untreated tissue from the subject that is treated, or from an untreated subject. Preferably the cells or tissue of the control are derived from the same tissue as the treated cells or tissue. In some embodiments, an untreated control subject suffers from, or is at risk from the same disease or condition as the treated subject. For example, in some embodiments, an untreated control subject does not raise an immune response to an antigen.

G. Combinations

MDNPs can be administered alone, or in combination with one or more additional active agent(s), as part of a therapeutic or prophylactic treatment regime. The MDNPs can be administered on the same day, or a different day than the second active agent. For example, compositions including MDNPs can be administered on the first, second, third, or fourth day, or combinations thereof.

The term "combination" or "combined" is used to refer to either concomitant, simultaneous, or sequential administration of two or more agents. Therefore, the combinations can be administered either concomitantly (e.g., as an admixture), separately but simultaneously (e.g., via separate intravenous lines into the same subject), or sequentially (e.g., one of the compounds or agents is given first followed by the second).

In some embodiments, the additional prophylactic or therapeutic agents can be vaccines for a specific antigen. The antigen can be the same or different to that encoded by the MDNPs.

In some embodiments, the MDNPs are useful as an agent to enhance the immune response to an antigen in a subject relative to the immune response raised to the same antigen in the absence of the MDNP delivery vehicles.

When MDNPs are used to induce an immune response, for example, to one or more antigens or allergens encoded by RNA encapsulated within the MDNPs, the administration of an effective amount of the MDNPs does not require the co-administration of an adjuvant to elicit the desired immune response. Therefore, in some embodiments, the MDNPs are administered in the absence of an adjuvant, or immuno-stimulatory molecule.

EXAMPLES

Example 1. Construction of MDNPs Containing RNA Molecules for Use as Vaccines Materials and Methods Plasmids and Cloning Conventional mRNAs, without chemical modification or stabilizing UTRs, were produced by cloning the antigen of interest into the HindIII and XbaI sites in the multiple cloning site of the mammalian expression plasmid pcDNA3-EGFP (a gift from Doug Golenbock (Addgene plasmid #13031) after excision of the eGFP coding sequence flanked by those restriction sequences. PCR products containing a Kozak consensus sequence (Kozak, M. *Nucleic Acids Res* 15, 8125-8148 (1987)) followed by the desired antigen coding sequence were inserted using the In-Fusion (Clontech Laboratories Inc.) cloning kit.

Venezuelan Equine Encephalitis Virus (VEEV)

VEEV replicon RNA vectors were produced by cloning antigens into the VEEV replicon plasmid pTK126, based on the wild-type TRD strain, kindly provided by Tasuku Kitada (Weiss Lab, MIT) to replace the mVenus coding sequence that lays downstream of the VEEV subgenomic promoter sequence. Luciferase-expressing VEEV replicon pTK158 was also provided by Tasuku Kitada (Weiss Lab, MIT).

Semliki Forest Virus (SFV)

SFV replicon RNA vectors were produced by cloning antigens into a modified version of the plasmid pSFV1 (Liljestrom, P. & Garoff, H. *Biotechnology* (N Y) 9, 1356-1361 (1991)), called pSFV1-JC1, which was constructed by restriction digestion of pSFV1-GFP (kindly provided by Giuseppe Balistreri, Ari Helenius lab, ETH Zurich, Institute of Biochemistry) at sites HindIII and XbaI followed by ligation of the PCR fragment spanning positions 8,145 to 9,226 with the addition of a custom cloning site linker immediately upstream of the fragment to reconstruct the original plasmid but carrying a unique BamHI restriction site in place of the cGFP coding sequence that was downstream of the sub-genomic promoter, which served as the site of insertion for antigen coding sequences.

Influenza Virus (HA) Antigen

The influenza HA coding sequence was amplified from the commercially available expression-ready influenza A H1N1 (A/WSN/33) cDNA Clone, Codon Optimized, full-length ORF (Sino Biological Inc. product VG11692-C).

Ebola Zaire Virus (EBOV) Antigen

EBOV GP and VP40 coding sequences were amplified from pWRG7077-GP and pWRG7077-VP40, respectively.

Ovalbumin (cOVA) Antigen

The cytoplasmically-restricted ovalbumin (cOVA) coding sequence was amplified by PCR from the vector pCI-neo-cOVA (Yang, et al., *Proc Natl Acad Sci USA* 107, 4716-4721, doi:10.1073/pnas.0911587107), a gift from Maria Castro (Addgene plasmid #25097), and was cloned into pcDNA3 or pSFV1-JC1 using the In-Fusion cloning kit according to the manufacturer's instructions.

Ovalbumin (OVA) and Luciferase

RNAs for studies of luciferase and cOVA expression in tissue culture, and OT-1 stimulation in vivo were generated from linearized plasmid vectors by in vitro transcription with MEGAscript kits (Life Technologies), 5' capped to produce cap-0 structured 7-methylguanylate 5' ends using ScriptCap m7G Capping System kits (CellScript Inc.), and 3' poly(A)-tailed using A-Plus Poly(A) Polymerase Tailing kits (CellScript Inc.), all according to the manufacturer's protocols. For all other experiments, RNAs were synthesized essentially the same way except for inclusion of 2'-O-methyltransferase (from ScriptCap™ 2'-O-Methyltransferase kits, CellScript Inc., according to the provided protocol) in the capping step to methylate the cap-adjacent 5' nucleotide of the RNA, thus producing a cap-1 structure and ensuring more efficient protein translation. Conventional mRNA was synthesized from the pcDNA3-derived plasmids carrying the antigen cloned into the HindIII/XbaI sites using T7 RNA polymerase after linearization with SacI. These mRNAs contained virtually no 5' or 3' UTR sequences, save for the short vector-derived space intervening between the T7 promoter and Kozak consensus sequence at the start codon, and between the stop codon and a restriction site downstream of the SacI restriction site used for linearization. SFV-based RNA replicons were constructed from the pSFV1-JC1 derived plasmids using Sp6 RNA polymerase transcription after linearization with SpeI.

Modified Dendrimer Synthesis 2-tridecyloxirane was synthesized by the dropwise addition of 1-pentadecene (TCI) to a 2× molar excess of 3-chloroperbenzoic acid (Sigma) in dichloromethane (BDH) under constant stirring at room temperature. After reacting for 8 hours, the reaction mixture was washed with equal volumes of super saturated aqueous sodium thiosulfate solution (Sigma) three times. After each wash, the organic layer was collected using a separation funnel. Similarly, the organic layer was then washed three times with 1 M NaOH (Sigma). Anhydrous sodium sulfate was added to the organic phase and stirred overnight to remove any remaining water. The organic layer was concentrated under vacuum to produce a slightly yellow, transparent oily liquid. This liquid was vacuum distilled (~50 mTorr, ~80° C.) to produce clear, colorless 2-tridecyloxirane. Generation 1 poly(amido amine) dendrimer with an ethylenediamine core (Dendritech, Inc.) was then reacted with 2-tridecyloxirane.

The stoichiometric amount of 2-tridecyloxirane was equal to 1.5× the total number of amine reactive sites within the dendrimer (2 sites for primary amines and 1 site for secondary amines). Reactants were combined in cleaned 20 mL amber glass vials. Vials were filled with 200 proof ethanol as the solvent and reacted at 90° C. for 7 days in the dark under constant stirring to ensure the completion of the reaction. The crude product was mounted on a Celite™ 545 (VWR) pre-column and purified via flash chromatography using a CombiFlash Rf machine with a RediSep Gold Resolution silica column (Teledyne Isco) with gradient elution from 100% CH2Cl2 to 75:22:3 CH2Cl2/MeOH/NH4OH$_{aq}$ (by volume) over 40 minutes. Thin layer chromatography (TLC) was used to test the eluted fractions for the presence of modified dendrimers using an 87.5:11:1.5 CH2Cl2/MeOH/NH4OHaq (by volume) solvent system. Modified dendrimers with different levels of substitution appeared as a distinct band on the TLC plate. Fractions containing unreacted 2-tridecyloxirane and poly(amido amine) dendrimer were discarded. Remaining fractions were combined, dried under ramping high vacuum for 12 hours and stored under a dry, inert atmosphere until used. All products contained a mixture of conformational isomers.

Assembly and Purification of MDNPs Containing RNA

Nanoparticles were formulated using a microfluidic mixing device as described by Khan, et al., *Nano Lett*, doi: 10.1021/nl5048972 (2015); Khan, et al., *Angewandte Chemie* 53, 14397-14401, doi:10.102/anie.201408221 (2014).

Briefly, modified dendrimer and 1,2-dimyristoyl-sn-glycero-3-phosphoethanolamine-N-[methoxy (polyethylene glycol)-2000] (Avanti Polar Lipids) were combined in ethanol.

RNA was diluted with UltraPure, DNase/RNase-Free, endotoxin free distilled water (Invitrogen) and sterile 100 mM pH 3.0 QB Citrate Buffer (Teknova, Inc.) to a final citrate concentration of 10 mM. The ethanol and citrate streams were loaded into gastight glass syringes (Hamilton Co.) and using a microfluidic mixing device, the ethanol and citrate streams were combined and mixed in a 1:3 volumetric flow rate ratio (combined total flowrate equal to 5.3 mL/min) to produce nanoparticles. Using glassware washed for 24 hrs. in 1.0 M NaOH (Sigma) for endotoxin removal and sterilized in a steam autoclave, nanoparticles were dialyzed against sterile, endotoxin-free PBS using 20,000 MWCO Slide-A-Lyzer G2 dialysis cassettes. Dialyzed nanoparticles were sterile filtered using 0.2 micron poly(ether sulfone) filters (Genesee Scientific) and characterized with a Zetasizer NanoZS machine (Malvern). The concentration of RNA was determined by theoretical mass balance calculations and confirmed by NanoDrop measurement (Thermo Scientific). The final nanoparticles contained a 11.5:1 mass ratio of modified dendrimer to 1,2-dimyristoyl-sn-glycero-3-phosphoethanolamine-N-[methoxy (polyethylene glycol)-2000] and a 5:1 mass ratio of modified dendrimer to RNA. The size distribution of the MDNPs was assessed by dynamic light scattering and transmission electron microscopy.

Results

Figure 2D:
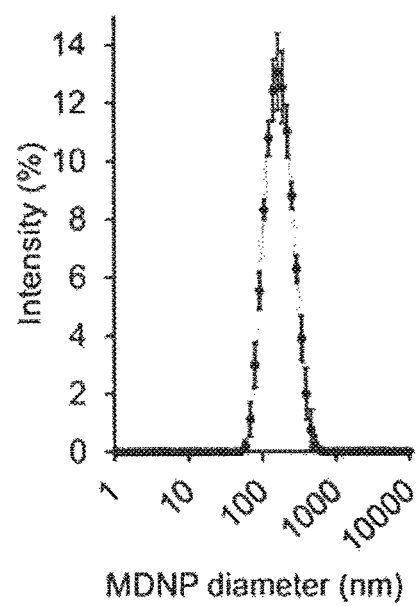
FIG. 2D is a line graph showing Intensity (%) over MDNP (Modified dendrimer nanoparticle) diameter (nm) on a logarithmic scale. Error bars±S.D. and n=3.

A MDNP vaccine platform was developed for the delivery of molecules such as replicating RNAs (repRNA) to the cells of a subject using an adjuvant-free nanotechnology delivery system. Towards this goal, a unique, highly efficient delivery method for large self-amplifying mRNA delivery was developed through the use of modified, ionizable and amphiphilic dendrimers (see FIGS. 1A-1C and FIGS. 2A-2C). Transmission electron microscopy of MDNPs, and analysis of size distribution of nanoparticles indicated that low polydispersity particles (FIG. 2D) were routinely produced using this method.

This MDNP vaccine platform is highly flexible, and can be rapidly tailored to the unique needs of each patient on the order of days. The ability to simultaneously generate multiple antigens (multiplexing) in host cells was demonstrated.

MDNP composed of replicons can be used for vaccination (i.e., as a modified dendrimer vaccine (MDV) platform). The MDV is a three component system, including an ionizable dendrimer-based nanomaterial, an amphiphilic PEG and RNA are combined to form the final vaccine nanoparticle.

Mdnp Deployment Strategies

As a vaccine, the MDNPs can be deployed in a broad range of different ways. In one example, the MDNPs include one type of amplifiable payload: replicons (FIG. 1A). Once released inside the cell cytoplasm, replicons are translated by the ribosomes to create both RNA dependent RNA polymerases (RdRp) and antigens. The RNA dependent RNA polymerase (RdRp) makes more copies of the full-length replicon, or copies of antigen only by virtue of a subgenomic promoter. The ribosome continue to translate the full-length replicon copies or the shorter antigen-only (conventional) mRNAs. For this strategy, one type of amplifiable payload is delivered into the cytoplasm of cells.

In another strategy, the MDNP simultaneously carries two types of amplifiable payloads: replicons and mRNAs that contain the 3' and 5' untranslated regions (UTRs) of a replicon (FIG. 1B). In this strategy, the RdRp can start copying at the beginning of the replicon or at the subgenomic promoter. The first is the replicon. The second are mRNAs that incorporate the 5' and 3' untranslated regions (UTRs) of the replicon. The RdRp created by ribosomal translation of the replicon can act in three ways: (1) to replicate the entire replicon; (2) to replicate the mRNA only by starting at the replicon's subgenomic promoter; and (3) to replicate the modified mRNA with replicon UTRs. For this strategy, the two types of amplifiable payloads are co-delivered into the cytoplasm of cells. The short mRNA that is made at the subgenomic promoter can only be translated by ribosomes and cannot be copied by RdRp because it lacks replicon UTRs. However, the RdRp can replicate the mRNA with replicon UTRs. Thus, the inclusion of mRNA with replicon UTRs increases the overall efficiency of the system because two amplifiable payloads are simultaneously delivered into cells, instead of one.

MDNPs are capable of activating both the cytotoxic T cell and humoral arms of the immune system in order to create durable and long-term protection against one or more target antigens. MDNP vaccines were rapidly generated over the order of days, which contrasts to the many months required for conventional vaccine production. Because of its flexibility, the MDNP platform can easily leverage the readily available exome sequence data from tumor cell models of pancreatic cancer, colon carcinoma, and leukemia (Bhadury, et al., Oncogenesis 2, e44, doi:10.1038/oncsis.2013.8), for the rapid creation of customized cancer vaccines.

Example 2. Modified Dendrimer RNA Nanoparticles are Stable in Serum at 37° C. And at 4° C.

Materials and Methods

Statistical Analyses

Means were compared by ANOVA with Tukey multiple comparison corrections. For survival curves, the Mantel-Cox test was used. P values below 0.05 were considered statistically significant.

Primary Cells and Cell Lines

C2Cl2 mouse myoblasts (ATCC CRL-1772) and L6 rat myoblasts (ATCC CRL-1458) were maintained in DMEM supplemented with 10% FBS. For differentiation, C2Cl2 cells were allowed to grow to confluency and then maintained in DMEM supplemented with 10% horse serum (Sigma) for five days, by which point the majority of the monolayer exhibited large contiguous fused myotube-like structures. DC2.4 cells were maintained in RPMI supplemented with 10% inactivated FBS, 1% L-glutamine, and 60 uM 2-mercaptoethanol. Mouse embryonic fibroblasts (MEFs) were obtained from Lonza and maintained in DMEM supplemented with 10% FBS. Human foreskin fibroblasts (HFFs) were maintained in DMEM supplemented with 10% FBS, 2 mM glutamine, 10 mM Hepes pH 7.5, and 20 µg/mL gentamicin. MDNP-treatment experiments were performed by applying 400 ng encapsulated RNA per well on 70-90% confluent cell monolayers in 96-well dishes and assaying by luciferase assay (see main text Materials and Methods) after 24 hours.

Tissue Culture Protein Expression Assays

Luciferase gene expression in nanoparticle-treated cells was measured using the Steady-Glo Luciferase Assay System (Promega Corporation) according to the manufacturer's protocol. Expression of cOVA, influenza HA, and EBOV GP, in RNA-transfected BHK21 cells was assayed by immuno-blotting. Cells were lysed and proteins extracted in RIPA-benzonase buffer (20 mM Tris (pH 8), 137 mM NaCl, 0.5 mM EDTA, 10% glycerol, 1% Nonidet P-40, 0.1% SDS, 1% deoxycholate, 2 mM $MgCl_2$, 25 U/µl benzonase [EMD Millipore], protease inhibitors [complete, Mini, EDTA-free, Roche Life Science, used according to the manufacturer's recommendations]), and separated by SDS-PAGE before transfer to PVDF membranes for immunoblotting. Membranes were blocked with 10% milk in TBS-T and incubated with the following antibodies for detection in blocking buffer for 2-4 hours at room temperature: for cOVA detection, rabbit polyclonal to ovalbumin, HRP conjugated, ab20415 (Abcam plc) diluted 1:3000; for HA detection, single-chain alpaca nanobody VHH68 (Dougan, et al., Nature 503 (7476): 406-409 (2013)) diluted 1:1000 followed by anti-penta-His HRP conjugate (Qiagen) diluted 1:5000; for EBOV GP detection, mouse monoclonal 6D8 diluted 1:1000 followed by anti-mouse HRP diluted 1:10000. Enhanced luminol-based detection was performed using Western Lightning-ECL kits (Perkin Elmer Inc.). Cell surface expression of influenza HA was assayed by dissociation of transfected cell monolayer by trypsinization, washing once in growth medium, and staining for 15 min. on ice with Alexa Fluor 647-conjugated VHH68 in PBS. Cells were washed twice with PBS and surface staining was measured by FACS on a BD LSR II Flow Cytometer (BD Biosciences).

Real-Time Analysis of Nanoparticle Disassembly by FRET

Fluorescence Resonance Energy Transfer (FRET) was used to estimate the stability of nanoparticles under simulated intramuscular conditions. Desalted, HPLC-purified RNA duplexes labelled at the 5' end of the sense strand with either Alexa Fluor594 or Alexa Fluor647 dyes were purchased from Integrated DNA Technologies. Nanoparticles with equimolar amounts of both types of RNA were formulated and diluted to a final RNA concentration of 2 µg/mL. When in close contact (i.e. within the intact MNDP), the RNAs would act as a Fluorescence Resonance Energy Transfer (FRET) pair.

In quadruplets, 100 µL of the diluted nanoparticles were added each well of an opaque black 96 well plate. 100 µL of 50% AB human serum (Invitrogen), which had been diluted in PBS, was added to each well. Negative control wells contained free siRNA. Positive control wells contained PEI nanoparticles. PEI nanoparticles were formed by the repeat pipetting of 800 MW PEI (Sigma) with RNA in a 5:1 PEI to RNA mass ratio in a 10 wt % sucrose solution. The plate was sealed with a clear adhesive plate seal and placed into a Tecan Infinite M200 microplate reader set to 37° C. When the MDNPs disassembled, the released RNAs would no longer be close enough to generate a FRET signal. To measure FRET, samples were excited at 540 nm and the fluorescent intensity was read at 690 and 620 nm every 5 minutes for 2 hours. FRET was calculated as the 690 nm/620 nm fluorescent intensity signal ratio. Negative controls were free RNA. PBS was used to determine background levels. FRET signal was normalized to the value of the completely ruptured nanoparticles, which were determined after adding octyl β-D-glucopyranoside (Sigma) to a final in-well concentration of 2 wt % and mixing for 1 hour at 37° C.

Analysis of Nanoparticle Disassembly Following Storage at 4° C.

To determine vaccine stability at 4° C., nanoparticles containing luciferase replicon RNA were created and stored at 4° C. for extended periods of time. HeLa cells were treated with a fixed amount of the nanoparticles and luciferase expression was assayed after 14 hours.

Results

Nanoparticle-based vaccines should elicit robust antigen expression, protect the RNA payload from environmental RNase activity, and retain these properties over extended periods of storage, ideally without the need for a cold chain.

Figure 2E:
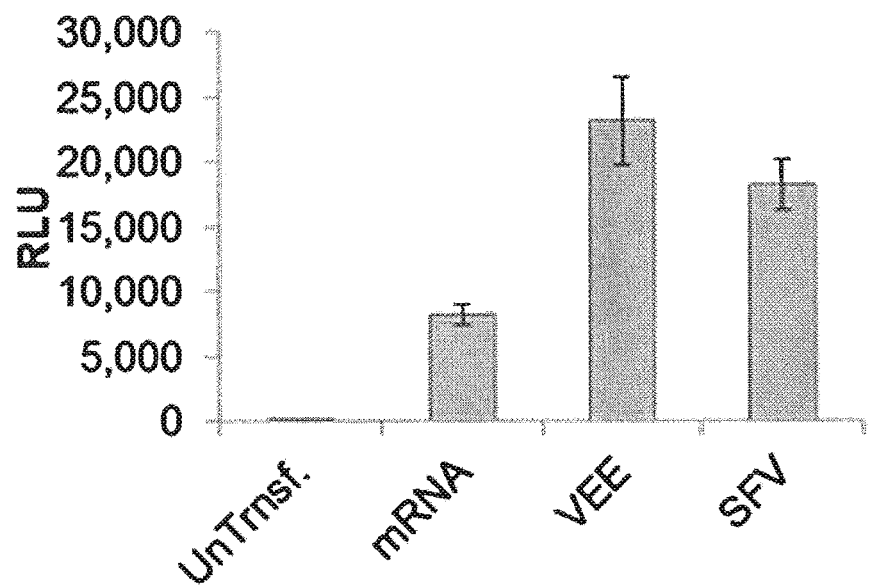
FIG. 2E is a histogram showing Firefly luciferase activity (RLU) in BHKs cells mediated by Untransformed BHK cells, as well as BHK cells transformed with conventional mRNA and replicon RNAs based on VEE and SFV genomes. Error bars±S.D. of technical triplicates.

To test whether MDNPs exhibited these characteristics, VEEV replicon RNA encoding firefly luciferase was selected as a model nanoencapsulation cargo. Luciferase was chosen because VEEV-driven expression in tissue culture was strongest of the three RNA vectors tested (conventional mRNA, VEEV replicon, and SFV replicon) (FIG. 2E). The VEEV replicon RNA was therefore used in the formulation of MDNPs using a microfluidic-based production method (Khan, et al. Nano Lett, doi:10.1021/nl5048972 (2015); Khan, et al. Angewandte Chemie 53, 14397-14401, doi:10.1002/anie.201408221 (2014)).

Monodisperse particles (average diameter 100-150 nm as assessed by dynamic light scattering) optimized for intramuscular injection were routinely produced by this method. The stability of the MDNPs was estimated by nano-encapsulating FRET pair-labeled RNA followed by incubation in 50% human serum for 2 hours at 37° C. Ruptured particles release their labeled RNA payloads, which diminishes the intensity of the FRET signal.

The more stable MDNP nanomaterial was synthesized using 2-tridecyloxirane while the less stable control MDNP used 1,2-Epoxydodecane. Nanoencapsulation in the MDNP provides superior protection because nanoparticles remain intact and do not release their RNA payloads while in whole human serum. Because of this stability, the RNA payloads are protected from endonuclease degradation.

Figure 2F:
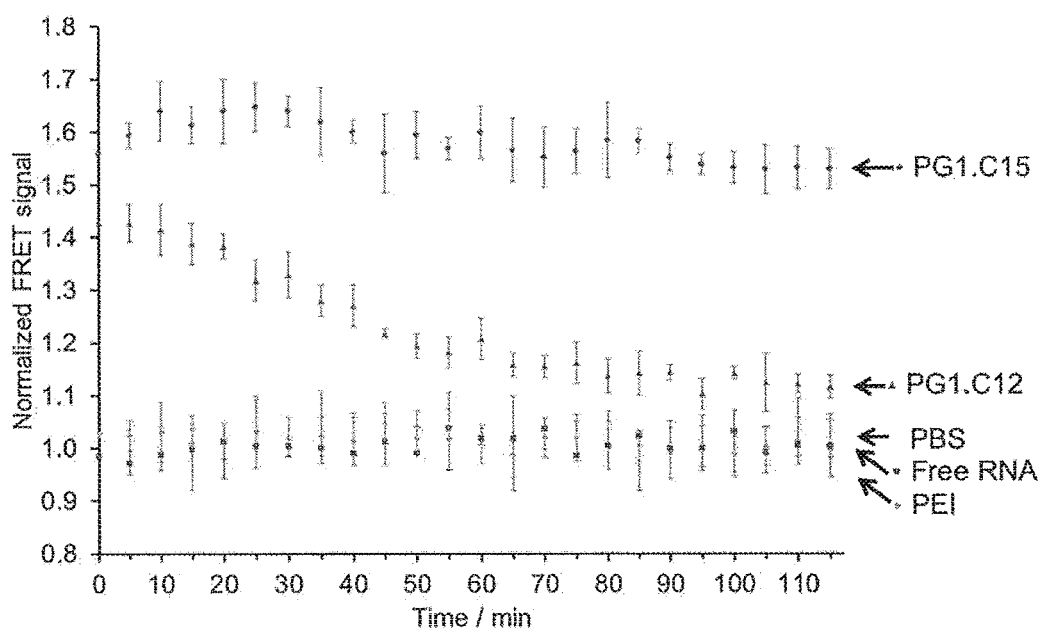
FIG. 2F is a line graph showing Normalized FRET signal (0.9-1.7) over Time for a period of 0-110 mins for each of PG1.C12 (▲); PG1.C15 (●); PEI (◇); Free RNA (■) and PBS (x), respectively. N=4-8 and error bars+S.D.

MDNPs remained stable and maintained a strong FRET signal when compared to chemically-ruptured MDNP, free RNA, and RNA nano-encapsulated in the cationic polymer polyethylenimine (FIG. 2F).

Figure 2G:
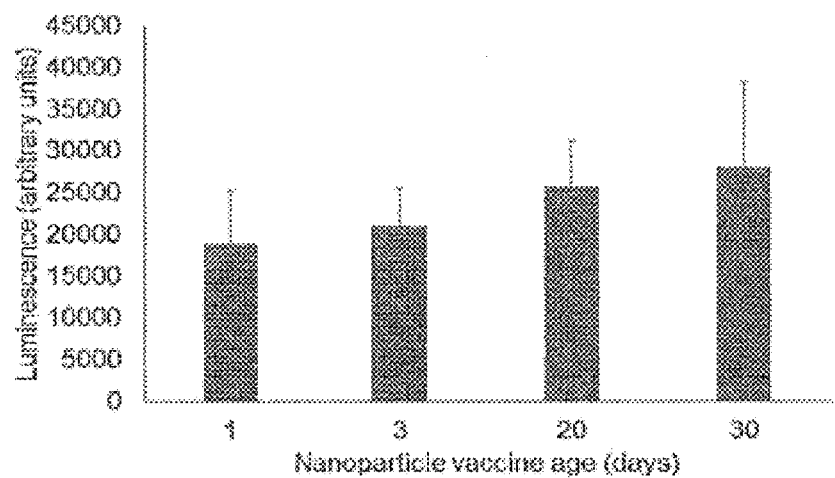
FIG. 2G is a histogram showing Luminescence (arbitrary units) ranging from 0-45,000 over Nanoparticle vaccine age for time points of 1 day, 3 days, 20 days and 30 days, respectively. N=4 and error bars±S.D.

The nanoparticles were also tested for stability over long periods of storage at 4° C. Stored MDNP preparations were applied to HeLa cells in culture to measure luciferase expression. No statistically significant changes in bioluminescence were observed when using particles stored at 4° C. for 1, 3, 20, or 30 days (FIG. 2G). Thus, after a minimum of 30 days storage, no statistically significant changes in luciferase transfection efficiency was detected by ANOVA analysis (with Tukey multiple comparison correction), indicating the particles remained stable, and the RNA payload intact.

The modified dendrimer is fully synthetic and purified, and the RNA payload is produced in the complete absence of cells. The MDNP nanomaterial has been established to avoid systemic increases in inflammatory cytokines in vivo at doses an order of magnitude greater than used for the immunizations described in Khan, et al., Angewandte Chemie 53 (52): 14397-14401 (2014); Khan, et al., Nano Lett 15 (5): 3008-3016 (2015). The particle preparations used in these studies are free of infectious contaminants and virtually endotoxin-free (<0.228 EU/mL, which is 40-fold lower than an acceptable endotoxin burden for viral/nonviral vectors (Brito et al., J Pharm Sci 100 (1): 34-37 (2011)).

Example 3. MDNPs (MDNP) Containing RNA Selectively Target and Kill Cancer Cells

Materials and Methods

The MDNP platform was used to create and assess an anti-cancer vaccine using a cancer tumor model involving cOVA-expressing tumor cells. The MDNP platform was used to vaccine mice with either conventional cOVA-expressing mRNA or Semliki Forest Virus (SFV) replicons, or Trp1-expressing VEEV replicon.

Rna Design and Expression

To create an ideal cancer therapy, bioinformatics is used to sequence each patient's unique tumor exome to identify "neoantigens". Corresponding mRNAs of these neoantigens are used to generate the antigens necessary to create immunity. Tumor cells expressing the model antigen OVA serve as a model system to test immunization against a non-wild-type protein sequence expressed in a tumor. Immunization can also be performed against antigens that are not mutated, but selectively enriched in the cancer cell type (e.g., Trp1 in melanomas). Using known methods, one or more genes are built by recursive PCR or are cloned from a cDNA or genomic library. The genes, along with promoters and terminators, are DNA sequences designed to express the desired mRNAs. DNAs of essentially any length and sequence can be produced in high yield in *Escherichia coli*. mRNA or repRNAs of any desired sequence can be produced from DNA templates by in vitro transcription techniques that are well-established in the field.

Mice

Wild-type female C57BL/6 mice were obtained from Jackson Laboratory and used between 5 and 8 weeks of age. Mice were housed at the Whitehead Institute for Biomedical Research and were maintained according to protocols approved by the MIT Committee on Animal Care.

Tumor Cell Lines cOVA and Trp1-expressing tumor cells (B16 cells) were maintained in culture at 37° C. and 5% CO2, and in DMEM with 10% FBS. In order to generate tumors, 500,000 cOVA-expressing cells were injected subcutaneously into the backs of wild-type female BL/6 mice. ~300,000 cells were injected for Trp1 study.

Strategy

Figure 3:
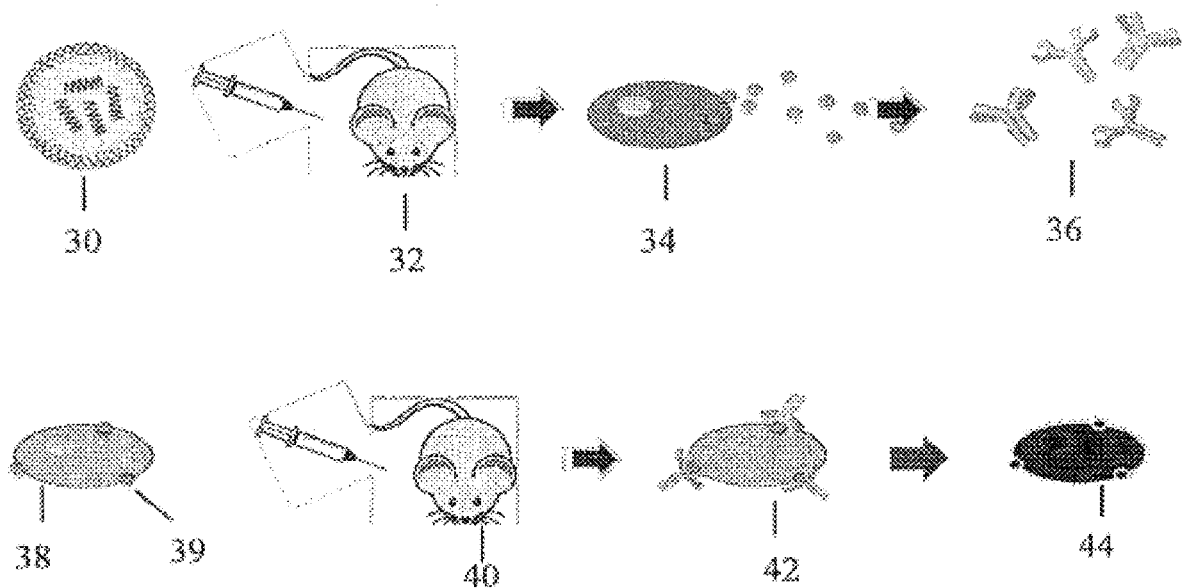
FIG. 3 is a schematic representation showing of an exemplary Vaccination regimen, using Modified dendrimer nanoparticles (30), intramuscular injection into test animals (32), production and release of a tumor-associated antigen in the muscle cells (34) and subsequent immune responses to antigens, resulting in production of antigen-specific antibodies and cytotoxic T cells (36); and preparation of tumor cells expressing antigen (38) by injection of tumor cells into the immunized mice (40), leading to recognition of tumor cells (42) and destruction of the tumor cells by the immune system (44).

At days 0 and 16, animals were vaccinated with 4 µg doses of modified dendrimer nanoparticle (MDNP) replicon vaccine. At day 28, 250,000 tumor cells were injected into mice for tumor development, as illustrated in FIG. 3. For Trp1 immunization, a single 40 µg dose was given four weeks before challenge.

Vaccination

Mice (2 per group) were treated with a combined 8 µg dose of naked cOVA mRNA (mRNA naked), naked cOVA SFV replicon (SFV rep naked), cOVA mRNA modified dendrimer nanoparticle vaccine (mRNA MDNP) or SFV cOVA modified dendrimer nanoparticle vaccine (SFV MDNP). Unimmunized mice received no treatment. After vaccination, mice were injected with 500,000 cOVA-expressing tumor cells (B16-OVA). Over the course of 1 month, all treatments utilizing the modified dendrimer platform developed no tumors.

In a more rigorous experiment, 10 mice per group were immunized a single time with 40 µg of naked or MDNP-delivered VEEV replicon expressing the model melanoma tumor antigen Trp1. Mice were challenged with 300,000 tumor cells that naturally express endogenous Trp1 (wild-type B16 cells).

Results

Figure 4A:
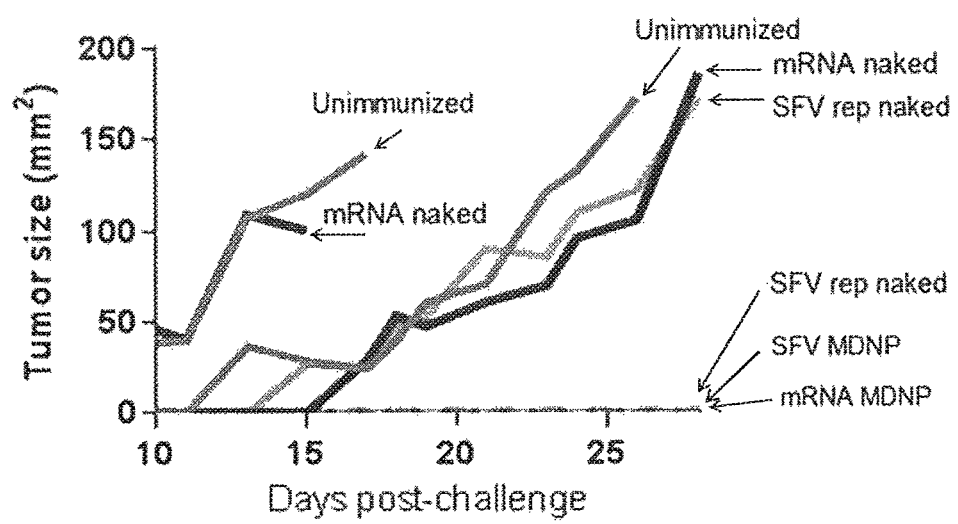
FIG. 4A is a line graph showing tumor size (0-200 mm2) over time (n=2, 10-28 Days post challenge) for each of unimmunized; mRNA naked; SFV rep naked; mRNA MDNP; and SFV MDNP, respectively.
Figure 4B:
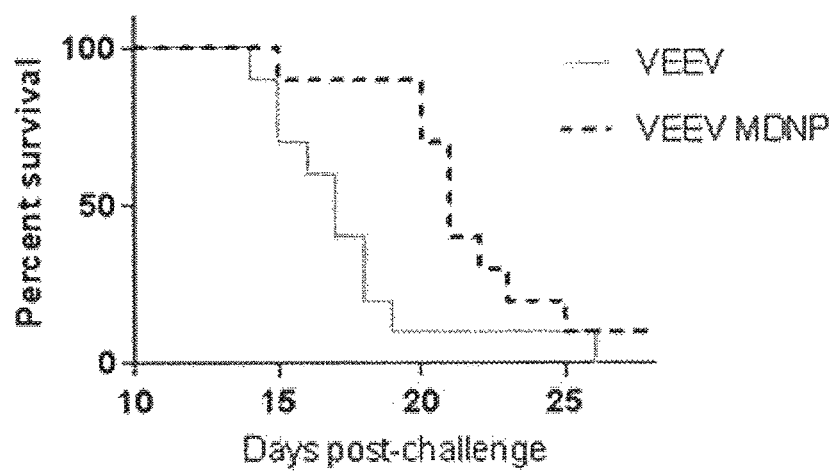
FIG. 4B is a line graph showing (%) Survival of mice (n=10) over time (10-28 Days post challenge) for each of unimmunized; mRNA naked; SFV rep naked; mRNA MDNP; and SFV MDNP, respectively.
Figure 5A:
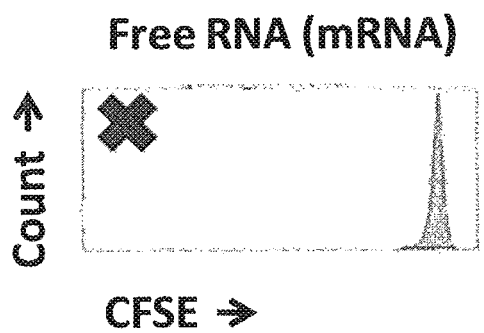
Figure 5B:
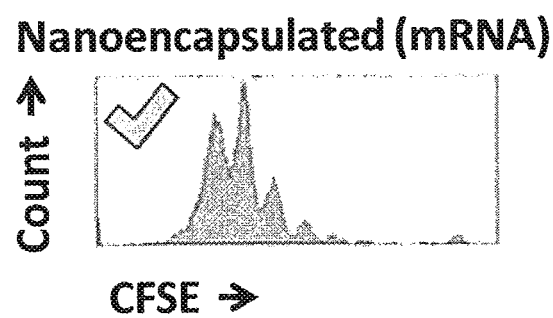
Figure 5C:
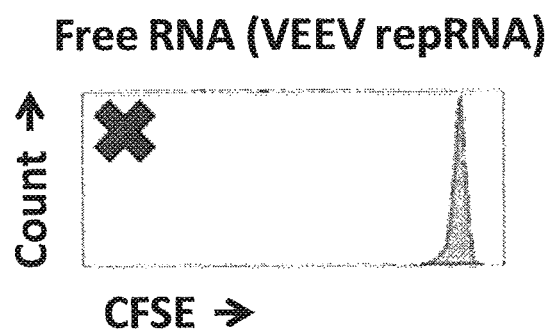
Figure 5G:
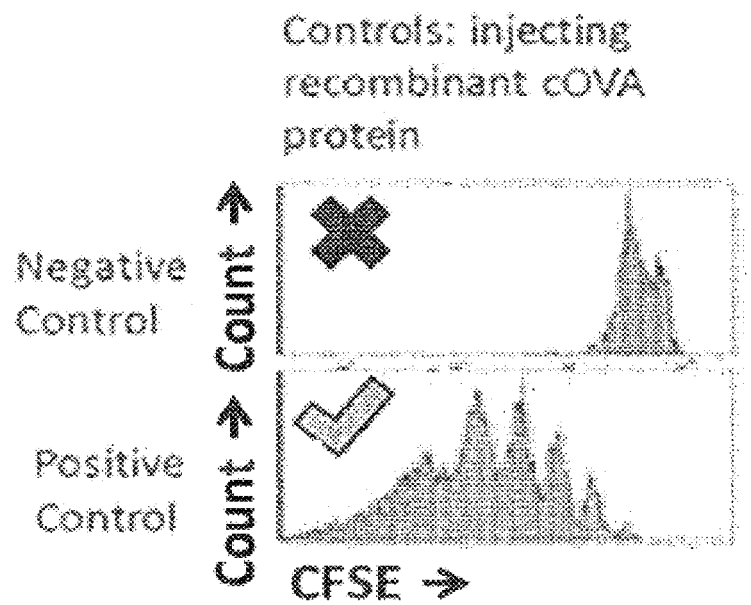
Figure 6A:
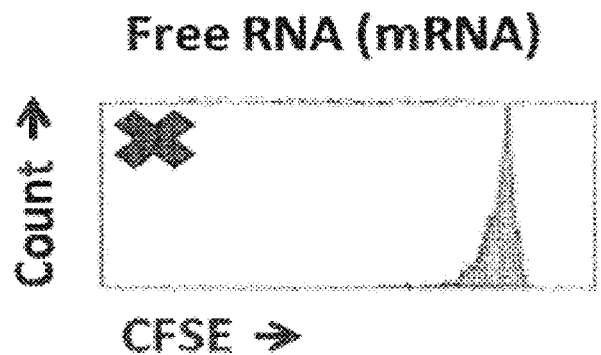
FIGS. 6A-6G are graphs showing Count (cells) over CFSE for Free mRNA (FIG. 6A) and Nanoencapsulated mRNA (FIG. 6B); Free VEE repRNA (FIG. 6C) and Nanoencapsulated VEEV repRNA (FIG. 6D); and Free SFV repRNA (FIG. 6E) and Nanoencapsulated SFV repRNA (FIG. 6F).
Figure 6B:
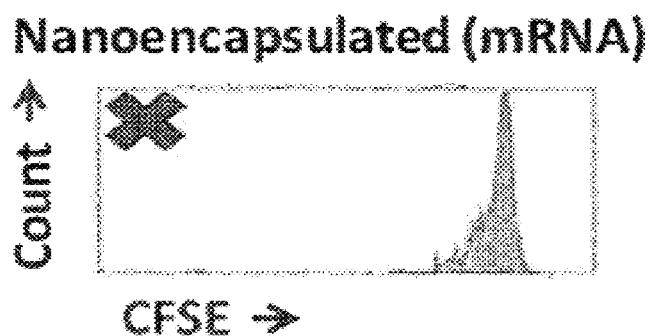
Figure 6C:
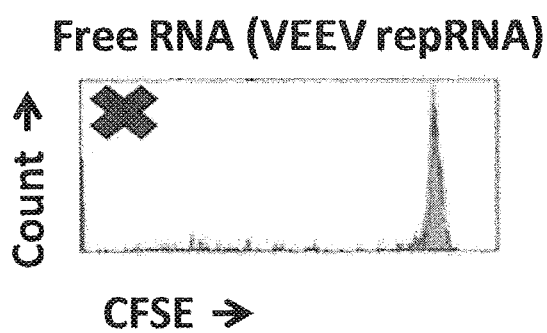
Figure 6D:
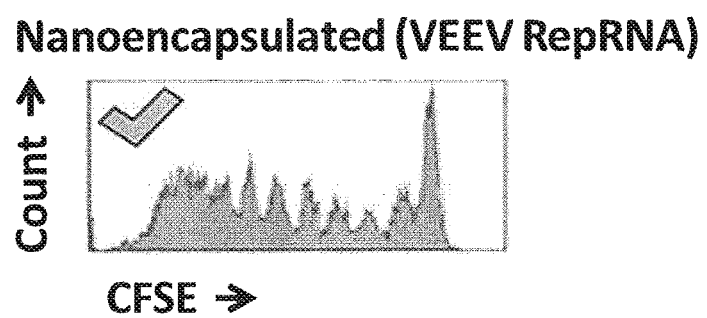
Figure 6E:
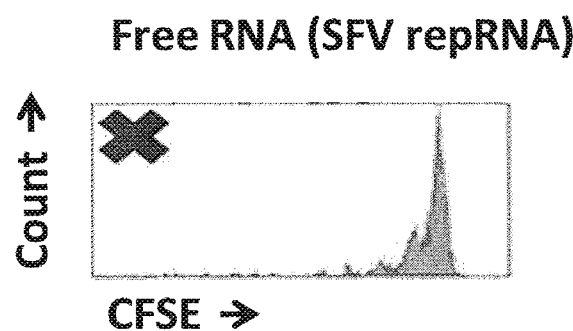
Figure 6F:
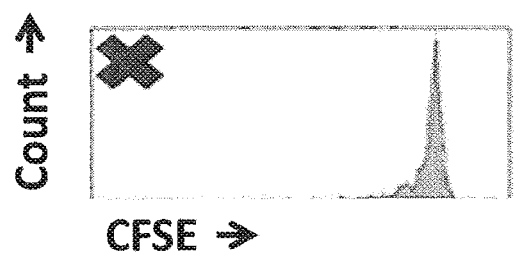
Figure 6G:
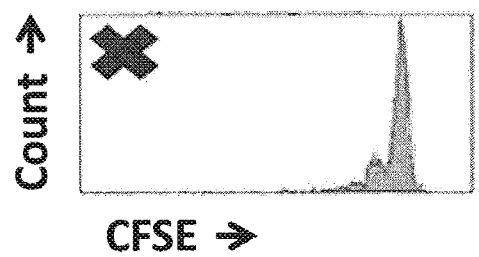

Unimmunized mice, as well as mice immunized with naked mRNA showed aggressive tumor development, which necessitated euthanasia. Naked SFV replicon injections resulted in variable results as one animal showed no tumor development at all. By contrast, all animals vaccinated with conventional cOVA mRNA and SFV cOVA replicon via the MDNP platform showed no tumor development and 100% survival (FIGS. 4A-4B). For the more rigorous Trp1 immunization study, which represents a more realistic tumor vaccination model, a single bolus injection of Trp1 VEEV replicon delivered by MDNP conferred a significant improvement in survival time (p=0.022 by Mantel-Cox test).

The MDNP is a multiplatform technology that can be used for many types of vaccinations. It can be used to generate immunity against deadly viral infections with as little as one dose. Future cancer vaccine work will leverage the multiplexing and hyperplexing capabilities of MDNP by incorporating RNA payloads that simultaneously generate immunity against many different cancer-specific antigens.

Example 4. RNAs Nanoencapsulated in Modified Dendrimers Stimulate Antigen-Specific T Cells In Vivo Materials and Methods Strategy Upon successful delivery, translation of RNA vector-encoded protein, in combination with the ability of in vitro-transcribed, exogenous RNA to activate cellular pattern recognition receptors including Toll-like receptors (TLRs), (Heil, et al. *Science*, 303, 1526-1529 (2004); Kariko, et al., *J Biol Chem*, 279, 12542-12550 (2004)), acid-inducible gene 1 (RIG-I) (Pichlmair, et al. *Science*, 314, 997-1001 (2006)), and RNA-dependent protein kinase (PKR) (Levin, et al., *J Biol Chem* 256, 7638-7641 (1981)) should elicit transgene-derived peptide display on Class I MHC molecules and stimulate CD8+ T cells. A cytoplasmically expressed ovalbumin fragment (cOVA) (Yang, et al., *Proc Natl Acad Sci USA*, 107, 4716-4721 (2010)) was chosen as a model intracellular antigen, and conventional mRNA, VEEV replicon, and SFV replicon RNAs were produced to express this protein.

Cell Lines

All cells were maintained at 37° C. and 5% $CO_2$. BHK21 cells were kindly provided by Tasuku Kitada (Weiss Lab, MIT) and maintained in EMEM supplemented with 5% FBS and 2 mM sodium pyruvate. Unless otherwise specified, BHK21 cells growing in log phase were transfected at 50-75% confluency using TransIT-mRNA transfection kits (Mirus Bio LLC) according to the manufacturer's protocols. HeLa cells were maintained in DMEM with 10% FBS.

Mice

Wild-type female C57BL/6 and Balb/cJ mice were obtained from Jackson Laboratory and used between 5 and 8 weeks of age. C57BL/6 Ptprca mice to serve as recipients of adoptive cell transfer were maintained in-house and used between 5 and 8 weeks of age. OT-1/Rag2−/− mice were maintained in-house by inbreeding of original founders purchased from Taconic.

Mice were housed at the Whitehead Institute for Biomedical Research and were maintained according to protocols approved by the MIT Committee on Animal Care. Mice were intramuscularly vaccinated with the indicated MDNP at Day 0 and Day 21.

Ifn Signaling Reporter Cell Assays

B16 cells carrying a SEAP reporter gene under the control of a combined IFN-α/β-inducible ISG54 promoter and ISRE regulatory element and lacking IFN-γ receptor activity ["type I" reporter cells (B16-BLUE™ IFN-α/β cells; Invivogen], or carrying the same reporter construct and lacking type I IFN receptor activity ["type II" reporter cells (B16-BLUE™ IFN-γ cells; Invivogen)] were transfected with 5-methylcytidine/pseudouridine base-modified mRNA as a control (5meC/Ψ mRNA; Trilink) or VEEV replicon RNA using TransIT-mRNA reagents. SEAP activity in the culture medium was quantified by colorimetric assay 20 h post-transfection. After 20 hours, 20 µL culture supernatant was analyzed for SEAP activity by adding to 180 µL of Quantiblue reagent (Invivogen) in flat-bottom clear 96-well dishes and allowing color to develop for 30 minutes. Absorbance was measured at 650 nm. VEEV replicon stimulates the type I IFN response in mouse cells.

Tetramer Staining Analysis

100 µL of blood from immunized mice was obtained by check bleed into K2EDTA microtainer collection vials (BD Biosciences), and erythrocytes were lysed using VersaLyse buffer (Beckman Coulter) for 10 minutes at room temperature. PE-conjugated SIINFEKL-specific tetramer (MBL International) staining was carried out along with APC-conjugated anti-CD8 clone 53-6.7 (BD Biosciences) for 30 minutes at room temperature in PBS+1% inactivated FBS. Cells were washed and analyzed by FACS as described in the main text. For MDNP mRNA immunization experiments, six mice were immunized and randomly divided into two groups of 3; one group was bled on days 4 and 12, the other on days 8 and 16 to prevent multiple collections in less than a week's span.

Quantifying mRNA Levels in Tissues 11 days post-immunization, mice were euthanized by $CO^2$ asphyxiation. Organs and tissues were immediately harvested, and frozen in liquid nitrogen. Frozen tissues were pulverized to form a powder, and tissue lysates were prepared in Tissue and Cell Lysis Buffer (Epicentre) supplemented with 0.5 mg/mL Proteinase K (Epicentre). The mixture was mixed at 1400 RPM for 2 hours at 65° C. and centrifuged at 16,000 RCF to remove any debris. The mRNA levels in the supernatant (lysate) were quantified using the QuantiGene 2.0 luminescent-based branched DNA assay kit and QuantiGene 2.0 probes against cOVA and Gapdh (Affymetrix) according to the manufacturer's protocol. Luminescent signal was measured with a Tecan Infinite 200 PRO plate reader. To avoid signal saturation and to ensure all luminescent signals remained within their linear regions, a standard curve for each tissue and target gene was constructed using samples from PBS-treated mice to determine the optimal dilutions for assay samples. The relative expression in treated groups was determined by calculating the ratio of target gene luminescence to Gapdh housekeeper gene luminescence. All values were normalized to the target:housekeeper gene ratio from PBS-treated mice.

T Cell Intracellular Cytokine Staining Assay

Splenocytes were isolated from mice 9 days after 40 µg MDNP-immunization, and cultured in growth medium (all components from Life Technologies unless otherwise indicated: RPMI 1620 with GlutaMAX supplemented with 8% FBS, 1 mM non-essential amino acids, 1 mM sodium pyruvate, 10 mM HEPES, 50 µM 2-mercaptoethanol (Sigma), and penicillin/streptomycin). Cytokine expression in response to stimulation with the immunodominant H-2Kb-restricted MHC class I OVA-derived peptide SIINFEKL (InvivoGen), or EBOV GP-derived WE15 peptide (WIPYFGPAAEGIYTE) was assayed by intracellular cytokine staining and FACS analysis essentially as described by Martins, et al., PLOS One 9(2):e89735(2014). Briefly, $1\times10^7$ splenocytes/mL were cultured in the presence of IL-2 (10U/ml), anti-CD28+antiCD49d (0.5 µg/mL each; BioLegend), and BFA (2 µg/mL final; Sigma) with or without 2 µg/ml peptide. The IL-2, anti-CD28, and anti-CD49d were omitted for stimulation with SIINFEKL, as the splenic response to this peptide in OVA vaccinated mice is apparent even without exogenous co-stimulation. Cultures stimulated non-specifically with 0.1 µg/mL PMA and 1 µg/mL ionomycin were used as single-color antibody staining controls for FACS analysis. After 6 hours in culture, cells were stained using the BD cytofix/cytoperm kit (BD Biosciences) according to the manufacturer's protocol with FITC-conjugated anti-CD8 (BioLegend), APC conjugated anti-CD4 (BioLegend), PE-conjugated anti-IFNg (BD Biosciences), and Pacific Blue-conjugated IL-2 (BioLegend). Stained samples were analyzed by FACS on a BD LSR II Flow Cytometer (BD Biosciences).

Adoptive Transfer and OT-1 Proliferation Assays

OT-1 cells were isolated from the mesenteric and inguinal lymph nodes and spleens of transgenic 6-12 week old OT-1/Rag2−/− C57BL/6 mice, and resuspended in PBS. The cells were labeled for 5 min. at room temperature with CFSE (Sigma) at a final concentration of 5 uM, then washed once in RPMI supplemented with 10% FBS before resuspension in PBS for injection. Wild-type CD45.1 mice 4-8 weeks of age received 1.5 million labeled OT-1 cells by i.v. injection. Four days after adoptive transfer, inguinal lymph nodes were dissected and lymphocytes isolated for FACS analysis. Cells were stained with 7-AAD (BD Biosciences), Alexa Fluor 700- or APC-conjugated anti-CD45.1, PE-Cy7- or APC-Cy7 conjugated anti-CD45.2, and Pacific blue- or PE-conjugated anti-CD8. Stained samples were analyzed by FACS on a BD LSR II Flow Cytometer (BD Biosciences).

T Cell Activation Assay

Splenocytes were isolated from mice and plated at a density of 10 million cells/ml in 96 well culture plates in the presence of growth medium (all components from Life Technologies unless otherwise indicated: RPMI 1620 with GlutaMAX supplemented with 8% FBS, 1 mM non-essential amino acids, 1 mM sodium pyruvate, 10 mM HEPES, 50 µM 2-mercaptoethanol (Sigma), and penicillin/streptomycin) only or 2 µg/ml OVA-derived peptide in growth medium. Peptides used were the immunodominant H-2Kb-restricted MHC class 1 OVA-derived peptide SIINFEKL (InvivoGen) or the H-2 I-Ab MHC class II restricted peptide ISQAVHAAHAEINEAGR (InvivoGen). After 5 days in culture, the concentration of 1:20 diluted supernatant IFNγ was quantified using IFNγ ELISA kits (BD Biosciences).

Results

The MDNP-encapsulated RNAs were successfully expressed in a broad variety of cell types in culture, including the human epithelial cell line HeLa, murine and human primary fibroblasts, the mouse dendritic cell line DC2.4, the murine and rat skeletal myoblast cell lines C2C12 and L6, and differentiated mouse myotubes derived from the C2C12 cell line (see Table 1). Intramuscular injection of MDNP was observed to drive readily detectible gene expression at the site of injection in vivo.

TABLE 1

MDNP delivery of firefly luciferase-encoding mRNA payloads to multiple cell types in culture

| | | Treatment | |
|---|---|---|---|
| Cell type | Species/origin | PBS | MDNP Luc mRNA |
| HeLa | Human epithelial | 162.9 ± 8.1 | 1,769.3 ± 255.9 |
| HFF | Human primary fibroblast | 160.8 ± 15.2 | 586.0 ± 113.6 |
| C2C12 | Mouse skeletal myoblast | 51.5 ± 3.6 | 1,971.6 ± 617.4 |

TABLE 1-continued

MDNP delivery of firefly luciferase-encoding mRNA
payloads to multiple cell types in culture

| Cell type | Species/origin | Treatment | |
|---|---|---|---|
| | | PBS | MDNP Luc mRNA |
| L6 | Rat skeletal myoblast | 16.8 ± 3.6 | 191.4 ± 26.8 |
| MEF | Mouse primary fibroblast | 108.3 ± 27.6 | 454.3 ± 128.2 |
| DC2.4* | Mouse dendritic cell | 16.5 ± 3.6 | 69.2 ± 14.0 |

Expression measured by luciferase assay as described in SI Materials and Methods, and reported in RLU ± SD of three biological replicates. HFF, human foreskin fibroblast; MEF, mouse embryonic fibroblast; RLU, relative light unit.
*No signal observed for unmodified mRNA, so base-modified (5-methyl-cytidine and pseudouridine) mRNA was used.

To test whether or not an immune response was induced using the MDNP system, a cytoplasmically expressed ovalbumin fragment (cOVA) was used as a model intracellular antigen. conventional mRNA, VEEV replicon RNAs, and SFV replicon RNAs were produced to express this protein.

The cOVA protein contains the dominant epitopes recognized by CD8 and CD4 T cells (Yang, et al., Proc Natl Acad Sci USA, 107, 4716-4721 (2010)). Expression of cOVA expression 14 hrs. post-transfection in BHK21 cells was confirmed by immunoblot using conventional TransIT transfection reagents, with the VEEV replicon proving to be the most efficacious.

To determine if antigen expression was sufficient to activate CD8+ T cells in vivo using MDNPs, OT-1 Rag1-KO C57BL/6 mice, a transgenic line expressing an H-2Kb restricted OVA-specific T cell receptor (TCR), were used as lymphocyte donors in an adoptive experiment.

Mice having received OT-1 T cells were given either unpackaged ("naked") RNA, or the same RNA encapsulated as MDNPs by bilateral i.m. injection. Three days post-immunization (four days post-transfer), proliferation of OT-1 T cells was assayed by CFSE dilution (FIGS. 5A-5G, FIG. 8A). Mice immunized with naked RNA failed to elicit proliferation of OT-1 cells. In mice that received RNAs via MDNPs, at least 6 rounds of proliferation were detected. Strongest proliferation was observed in mice immunized with mRNA-containing MDNPs.

Figure 7A:
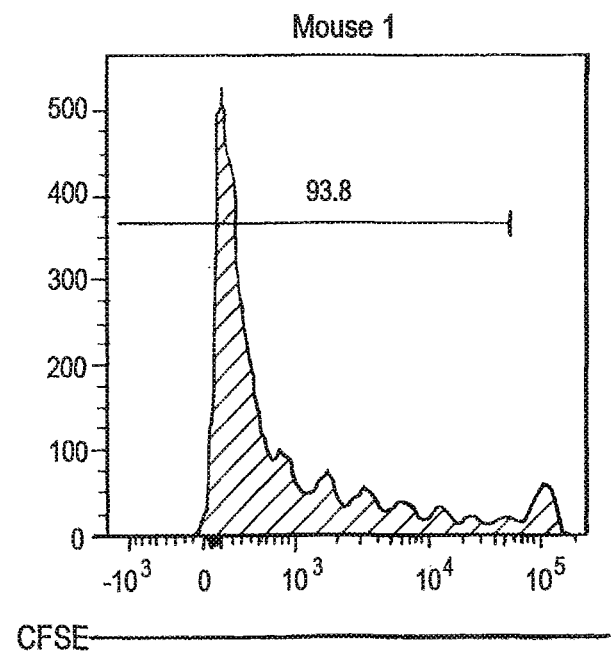
FIGS. 7A-7B are graphs of fluorescence-activated cell sorting (FACS) showing cell count over CFSE for OT-1 cells 4 days post-transfer/3 days post-immunization with 40 μg of Nanoencapsulated repRNA VEEV-cOVA MDNPs. Experimental results represent identical, independent experiments for each of two test animals, mouse 1 (FIG. 7A) and mouse 2 (FIG. 7B), respectively.
Figure 7B:
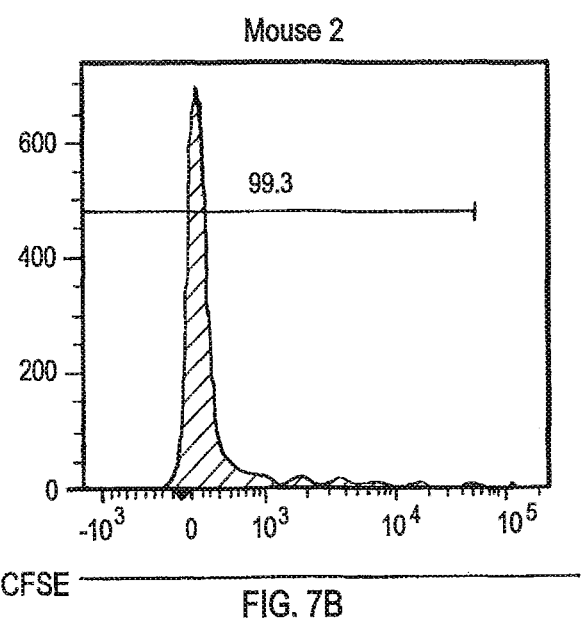

Administered doses were based on equivalent masses of injected RNA, and therefore a ~10-fold molar excess of conventional mRNA is injected relative to the replicon RNAs based on the differences in molecular weight. A ten-fold higher dose of packaged VEEV replicon RNA indeed yielded a profile of OT-1 proliferation similar to that of dendrimer-packaged mRNA. Results of OT-1 proliferation assay performed 4 days post-transfer/3 days post-immunization with 40 μg of VEEV-cOVA MDNPs are shown in FIGS. 7A-7B.

To establish whether a single dose of MDNP-delivered RNAs can result in efficient antigen presentation, C57BL/6 mice were immunized with naked or MDNPs, and adoptively transferred CFSE-labeled OT-1 cells 10 days later.

Figure 8A:
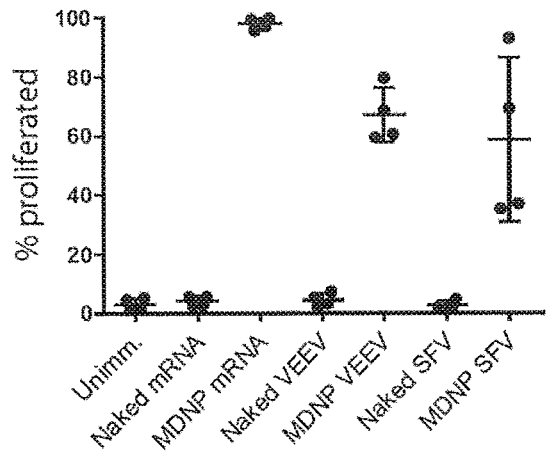
FIGS. 8A and 8B are graphs showing OT1 proliferation at day 3 (FIG. 8A) and day 14 (FIG. 8B), showing % Proliferation for each of Unimmunized sample, and each of samples immunized with naked mRNA; MDNP mRNA; Naked VEEV; MDNP VEEV; Naked SFV and MDNP SFV, respectively.
Figure 8B:
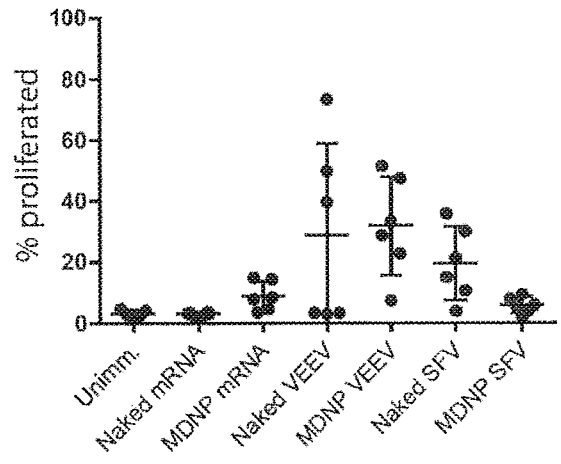

Four days post-transfer (i.e., 14 days post-immunization), proliferation was analyzed as described above (FIGS. 6A-6G). Naked mRNA immunization failed to induce proliferation of OT-1 T cells. mRNA MDNPs resulted in low, but detectable OT-1 proliferation 2/3 of the immunized mice. Immunization with naked replicon caused variable proliferation of OT-1 T cells. Mice immunized with naked SFV also exhibited highly variable results. However, with the MDNP system, the VEEV replicon RNA caused reproducible and consistent proliferation of OT-1 T cells in the majority of immunized mice (ranging from 20-50% in five of six animals) (FIG. 8B). MDNP-delivered SFV replicon RNA failed to induce OT-1 proliferation. Differences in the expression profiles of the two different alphavirus replicons, coupled with the short-term effects of nano-encapsulation may be responsible.

Figure 8C:
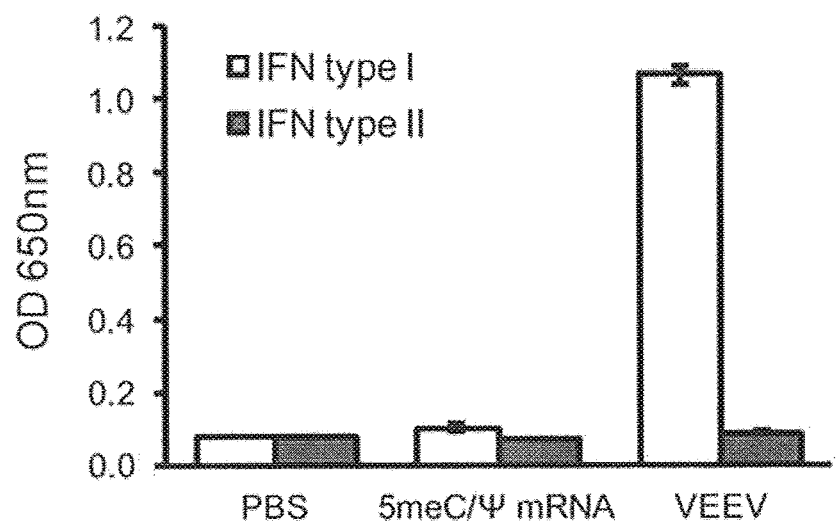
FIG. 8C is a histogram showing the relative amounts of IFN type I (a) and IFN type II (■) at OD 650, in each of PBS, 5mcC/Ψ mRNA, and VEEV samples, respectively. Error bars+SD for biological triplicates.

Therefore, MDNP-delivered VEEV replicons were pursued as a vaccine candidate. To confirm that VEEV MDNP could stimulate endogenous T-cell responses, C57BL/6 mice were immunized with a high (40-μg) dose of cOVA VEEV MDNP. After 9 d, intracellular IFN-γ and IL-2 production was measured in splenocytes stimulated in vitro with the immunodominant H2-Kb class IMHC-restricted OVA peptide SIINFEKL. In two independent experiments, >1% of endogenous CD8+ splenocytes from immunized mice contained discrete populations of strongly IFN-γ+ cells upon peptide stimulation. Eighteen days postimmunization, abundant circulating CD8+ T cells with TCR specificity for MHC class I-bound SIINFEKL, as detected by tetramer staining, were observed in similarly immunized mice. For comparison, in similar independent experiments using mRNA as the payload, fewer circulating tetramer-positive cells were detected over the course of the study, and levels were nearly undetectable by day 16. These observations, coupled with the fact that alphavirus replicons induce potent type I IFN responses (FIG. 8C), as well as apoptosis and antigen uptake by dendritic cells, further justified the selection of VEEV as the candidate payload for further experiments with a variety of target antigens. It should be noted that in MDNP VEEV-immunized animals, antigen-coding RNA was detectible by day 11 in the draining inguinal lymph nodes, raising the possibility that the immunogenic action of replicons delivered by MDNPs may not be limited to the site of injection, although the injection site is likely to be the major source of actual antigen production in vivo.

The activity of MDNP-delivered VEEV replicon construct (VEEV MDNP) was assessed as a vaccine candidate for yet another viral structural polyprotein, HIV1 Gag, as determined by Immuno-blotting performed 14 hours post-transfection with HIV1 Gag-specific goat polyclonal IgG vT-20 (Santa Cruz Biotechnology, Inc.). The VEEV replicon gave rise to clearly-visible expression of HIV1 Gag, whereas mRNA and SFV-mediated transfection did not give rise to visible expression.

Figure 9:
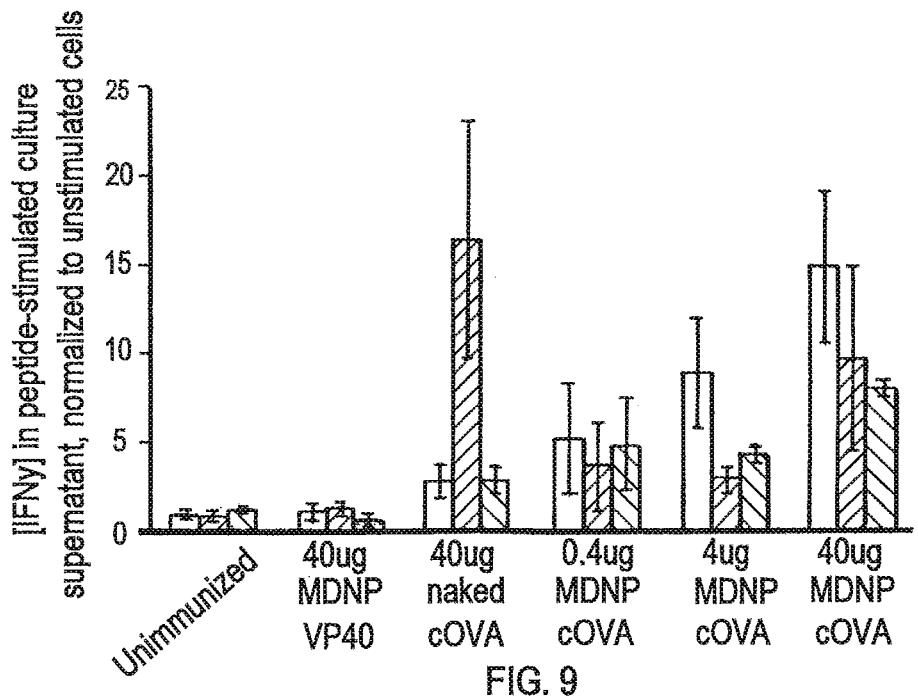
FIG. 9 is a histogram showing concentration of IFNg in peptide-stimulated culture supernatant, normalized to unstimulated cells, for each of Unimmunized, 40 μg MDNP VP40, 40 μg naked cOVA, 0.4 μg MDNP cOVA, 4 μg MDNP cOVA, and 40 μg MDNP, respectively.

To confirm that VEEV MDNP was capable of achieving endogenous T-cell responses, C57BL/6 mice were immunized with increasing doses of cOVA-expressing VEE MDNP. After 9 days, IFNg production was measured in splenocytes stimulated in vitro with either the immunodominant H2-Kb Class I MHC restricted I OVA peptide SIINFEKL (FIG. 9).

Splenocytes from control mice, or mice immunized with 40 μg of VEE MDNP encoding an irrelevant antigen failed to produce IFNγ upon peptide treatment. Splenocytes obtained from mice immunized with 40 μg of cOVA-expressing VEEV MDNP showed an 8-14 fold increase in IFNγ in response to peptide. Mice immunized with 0.4 μg or 4 μg of VEEV MDNP showed less of an increase.

Example 5. A Single Dose of HA-Expressing VEEV Replicon RNA Nanoparticles Protects Against Lethal Influenza Challenge Materials and Methods Anti-HA IgG ELISA High binding surface-treated polystyrene 96 well microplates (Corning) were coated overnight at 4° C. with 0.5 µg/ml recombinant influenza A H1N1 WSN/33 protein (Sino Biological Inc.) in PBS. Plates were blocked for 2 hrs. with blocking buffer (PBS with 10% FBS) at room temperature, and serum was applied to wells in duplicate at a 1:100 dilution in blocking buffer, and incubated for 2 hrs at room temperature. Plates were washed with wash buffer (PBS with 0.05% Tween-20), incubated at room temperature with anti-mouse IgG-HRP (GE Healthcare) diluted 1:3000 in blocking buffer for 1 hr. After 5 rounds of washing with wash buffer, plates were developed with TMB substrate (Sigma) for 20-30 mins., and the reaction was stopped by the addition of one volume of 1M HCl before reading absorbance at 450 nm.

Influenza Challenge

Balb/cJ mice (n=3) were immunized with VEE MDNPs encoding either an irrelevant antigen (cOVA) as control or the HA protein, and challenged them 14 days later with a lethal dose of influenza A/WSN/33. Immunized mice were inoculated by intranasal administration of a lethal dose ($5 \times 10^4$ CEID50) of influenza A/NWS/33 (H1N1) (ATCC), which kills 100% of infected Balb/c mice in under 9 days. Body weight was monitored daily, and mice were euthanized when over 20% loss was observed. Mice were considered recovered when pre-infection body weight was surpassed, and health monitored for an additional 3 weeks to ensure no clinical signs of infection were observed. A/WSN/33-infected animals were housed in an approved quarantine room at the Whitehead Institute.

Results

To establish whether the nanoparticle-based vaccine could elicit immunity that protects against a lethal viral challenge, RNAs that drove the expression of the influenza A/WSN/33 HA protein were generated.

In terms of the expression levels attained, VEEV replicon RNA outperformed the other constructs in tissue culture experiments. Even a 3'UTR-stabilized mRNA variant (Warren, L. et al. *Cell Stem Cell* 7, 618-630, 2010) did yield HA at levels comparable to the VEEV replicon. Correct processing and shuttling of the VEEV RNA-expressed HA protein to the cell surface was confirmed by surface immune-staining with an HA-specific single-chain antibody (Dougan, et al. *Nature* 503, 406-409, (2013)) (FIG. 11A).

Figure 11B:
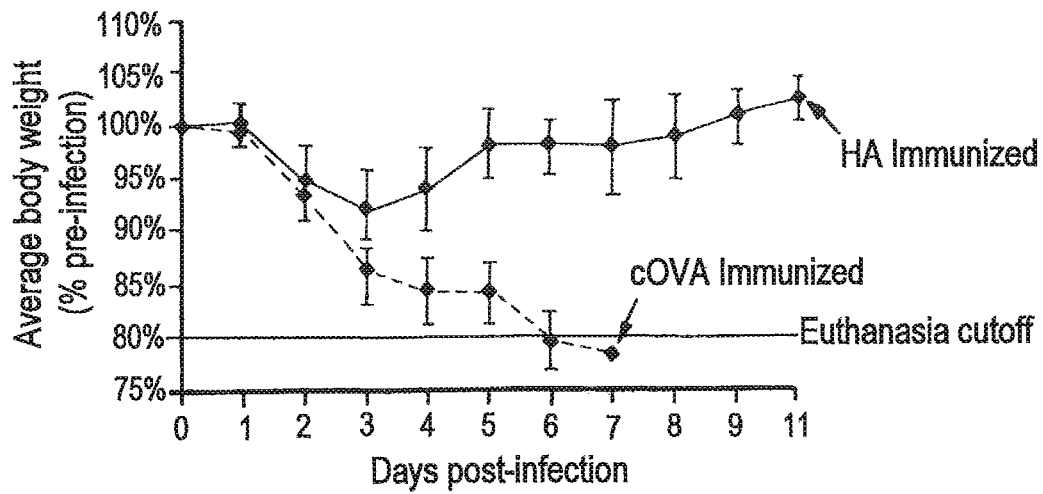
FIG. 11B is a line graph showing average body weight (% pre-infection) over time (Days post-infection) for each of cOVA immunized and HA-immunized animals, respectively. The euthanasia cutoff was at 80% pre-infection body weight, indicated by a line.
Figure 11C:
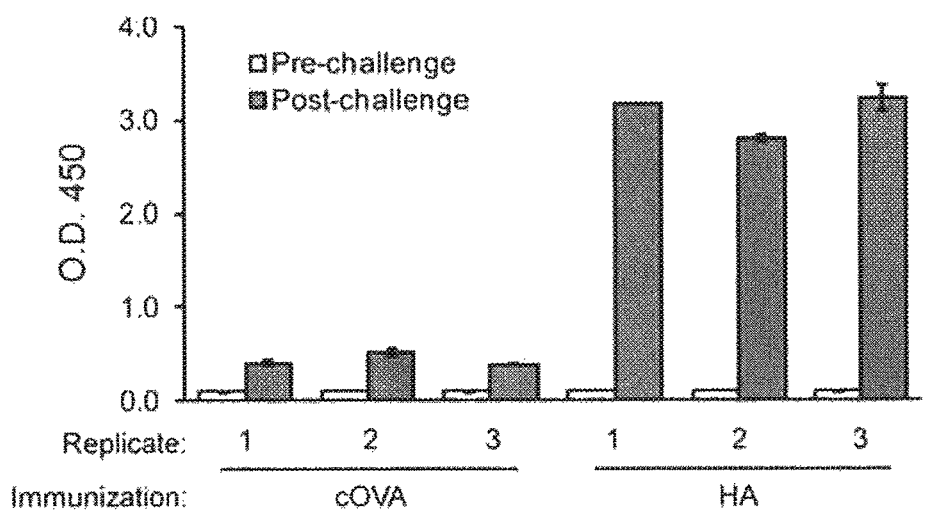
FIG. 11C is a histogram showing O.D. at 450 nm for each pre and post-challenge cOVA-immunized mice nos. 1-3; and HA-immunized mice nos. 1-3, respectively.

Control mice succumbed to infection by day 7, whereas HA-expressing nanoparticle-immunized mice survived challenge for at least 3 weeks, with no remaining clinical signs of infection at the time of termination of the experiment (FIG. 11B). No anti-HA IgG was detected in the sera of mice 7 days post-immunization, or in control mice at the time of sacrifice (6 or 7 days post-infection (FIG. 11C). At 7 days post-challenge HA-reactive IgG was readily detectable in the surviving mice immunized with HA-encoding VEEV replicon nanoparticles (FIG. 11C-11D), indicating that priming with the modified dendrimer mRNA vaccine potentiated a humoral response.

Example 6. Modified Dendrimer Nanoparticle-Delivered VEE Replicon RNAs Protect Mice from Lethal ZEBOV Challenge Materials and Methods Ebola glycoprotein (GP) was selected as the antigen to generate immunity against live Zaire Ebola virus. VEE-GP and VEE-GP/VP40 MDNPs (MDNP) vaccine candidates were compared for their ability to protect mice against a lethal EBOV challenge.

COVA MDNPs encode an irrelevant antigen and are used as a negative control. Unpackaged, naked GP replicon was used a nanoparticle-free control.

EBOV GP Immunization 10 mice for each group (VEE-GP or VEE-GP/VP40, n=10 each) were vaccinated with 4 µg of RNA nanoencapsulated in modified dendrimers by bilateral intramuscular (i.m.) injection, and boosted at day 21 with the same dose. Serum was collected at days 14, 35, and 48 to measure circulating EBOV GP-specific IgG titers by ELISA.

To measure cytokine production, three mice from each group were euthanized on day 25 to isolate splenocytes for ELISpot assays and intracellular cytokine staining. The remaining 7 mice were challenged at day 49, with mouse-adapted EBOV by intraperitoneal (i.p.) injection.

EBOV GP Serum ELISA

ELISA plates were coated at 4 degree overnight with recombinant mammalian Ebola GP at 2 µg/ml in PBS. Plates were washed 3× with PBS-T (PBS, 0.1% Tween-20) and then blocked 2 hours at RT with PBS-T 5% non-fat milk. Serum was diluted by half-log dilutions starting at 1:100 and incubated for 1 hour on GP-coated plates. Plates were then washed 3× with PBS-T, incubated with the indicated secondary HRP-antibody for 45 minutes, and then washed 3× with PBS-T. ELISA was developed using TMB substrate/stop solution and measured on a Tecan plate reader. Absorbance cut-off was determined as background+0.2 O.D.

EBOV Challenge

Mice were inoculated with a target titer of 1,000 pfu of ma-EBOV (Kuhn J H, et al. *Arch Virol*, 158 (6): 1425-1432 (2013)). All studies were conducted in the USAMRIID Biosafety Level 4 containment facility. Beginning on Day 0 and continuing for the duration of the in-life phase, clinical observations were recorded and animals were closely monitored for disease progression. Moribund animals were euthanized based on Institutional approved clinical scoring.

Dose-Response Experiments

For testing the response to different doses of vaccine, mice were vaccinated at day 0, day 21 and challenged with live virus on day 49. For a high-dose prime-only experiment, mice were vaccinated at day 0 and challenged with live virus on day 28.

Figures 11D, 12A:
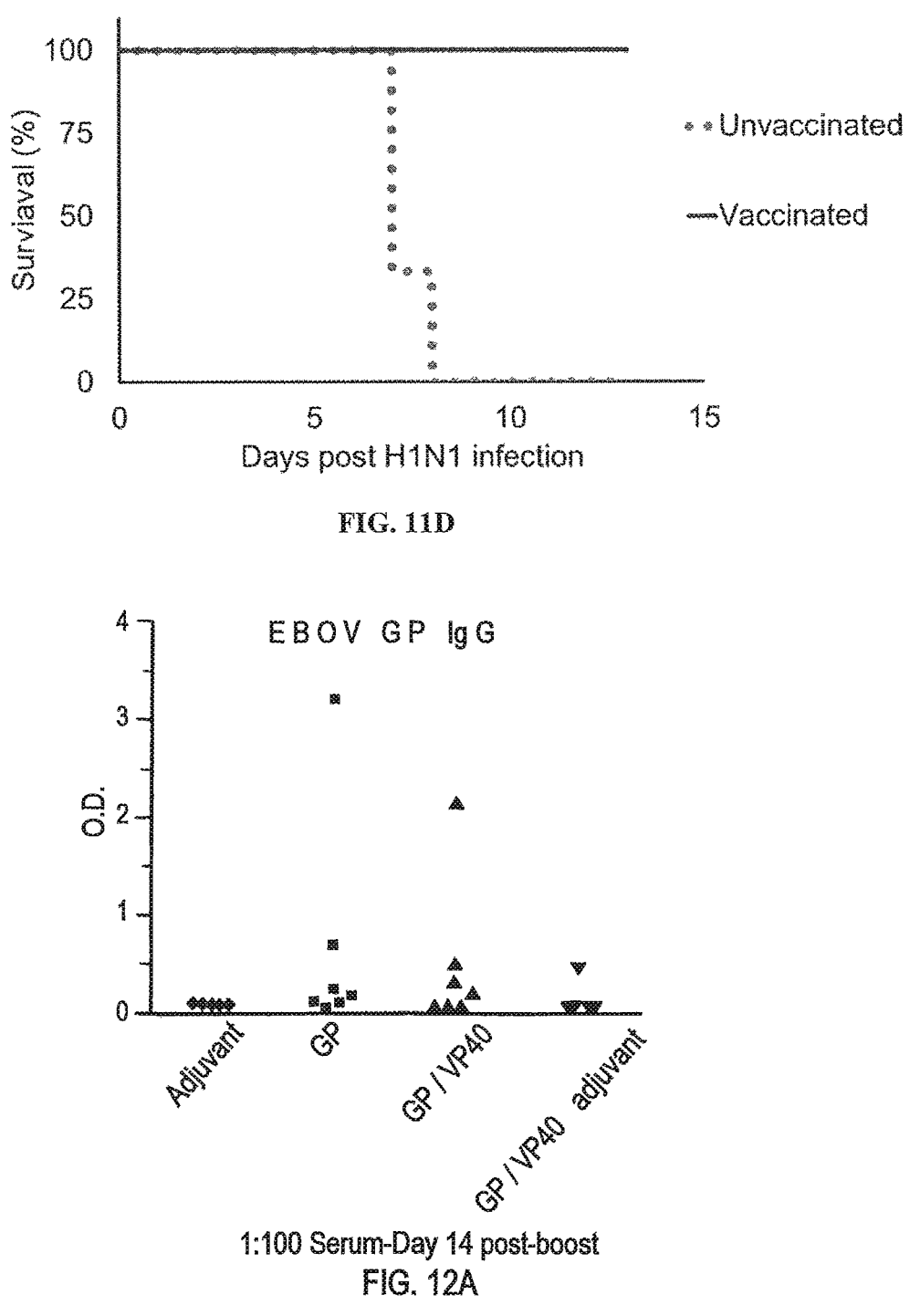

Results cOVA controls showed no protection against lethal Ebola challenge. Further, serum IgG specific for EBOV GP was negligible in the majority of immunized mice by day 14, as determined by ELISA against ZEBOV VLPs, and remained at comparable levels at day 48 (FIG. 12A).

Figure 12B:
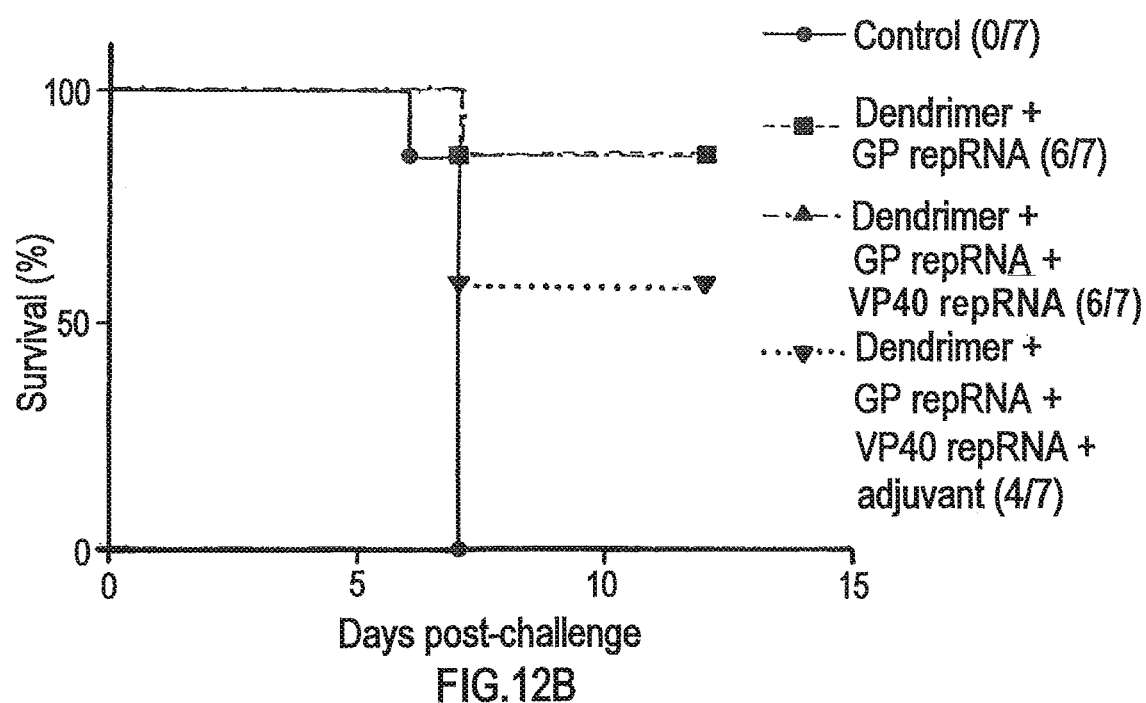
FIG. 12B is a line graph showing percent murine survival following challenge with Ebola virus (EBOV) for animals in an unimmunized control (●; 0/7); immunized with GP (■; 6/7); immunized with GP/VP40 (▲; 6/7); and immunized with Poly/GP/VP40 (▼; 4/7), respectively.

After challenge, all control (unimmunized) mice succumbed to infection by day 7 post-infection, while only 1/7 of either immunization group (VEE-GP or VEE-GP/VP40) died. Six of seven mice in the groups immunized with VEEV GP or the VEEV GP/VP40 mixture never developed clinical signs of infection throughout the study period (FIG. 12B).

Figure 13A:
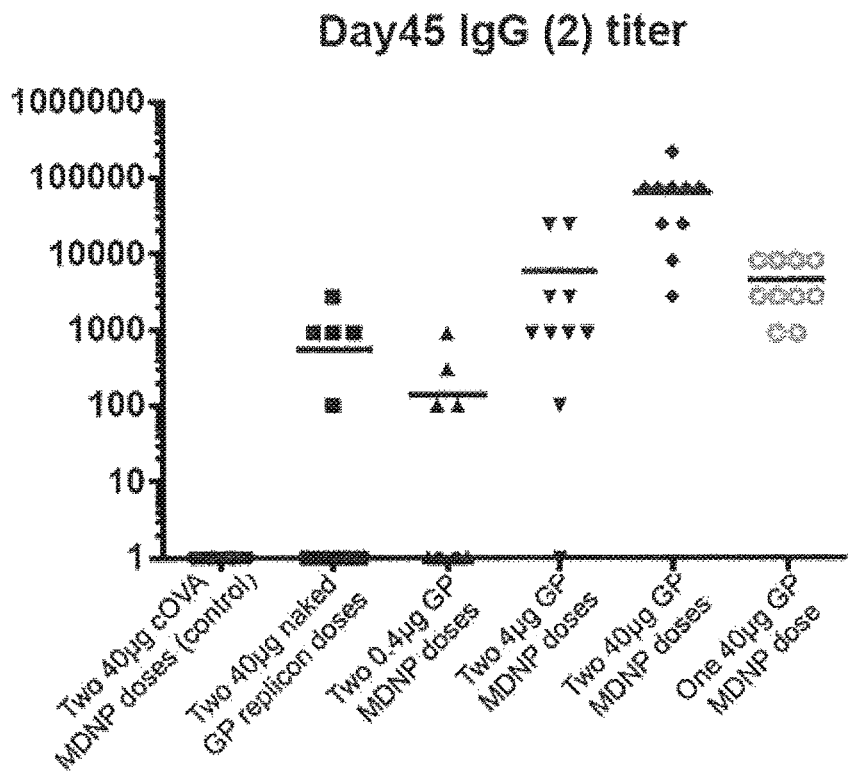
FIG. 13A is a graph showing antibody titer for each of Two 40 μg cOVA MDNP doses (control); Two 40 μg naked GP replicon doses (■); Two 0.4 μg GP MDNP doses (▲); Two 4.0 μg GP MDNP doses (7); Two 40 μg GP MDNP doses (♦); and One 40 μg GP MDNP dose (○), respectively.

In the dose-response experiments, no antibody titers were observed for cOVA MDNP controls. 2×40 μg naked GP replicon groups showed similar titers to the low dose 2×0.4 μg GP MDNP doses (FIG. 13A). A dose-response in antibody titers was observed for animals that received 2 doses of MDNPs.

Notably, the single dose of 40 μg GP MDNP produced high antibody titers with excellent precision (low standard deviation).

Figure 13B:
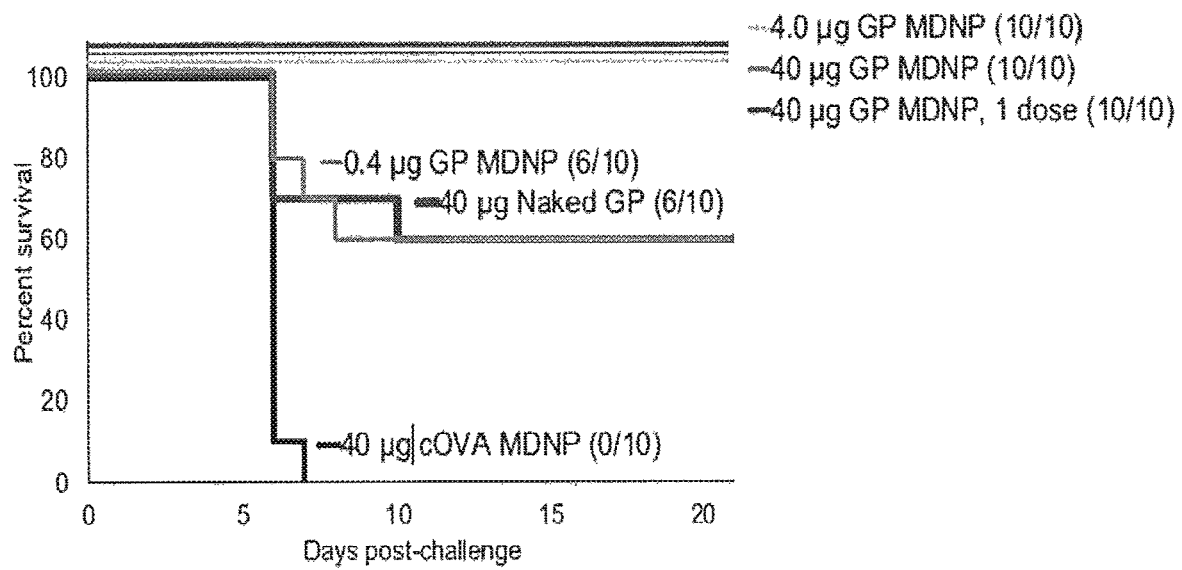
FIG. 13B is a line graph showing percent murine survival following challenge with Ebola virus (EBOV) for animals unimmunized with Two 40 µg cOVA MDNP doses (control); Two 40 µg naked GP replicon doses; Two 0.4 µg GP MDNP doses; Two 4.0 µg GP MDNP doses; Two 40 µg GP MDNP doses; and One 40 µg GP MDNP dose, respectively.

All mice in cOVA MDNP group died by day 7. The 2×4 μg, 2×40 μg and 1×40 μg GP MDNP groups showed 100% survival. The group receiving 2×40 μg naked GP replicon showed similar survival kinetics to the group receiving 2×0.4 μg GP MDNP dose (FIG. 13B).

Taken together, the protection data demonstrate that MDNPs confer protection in two mouse models of lethal viral infections. The non-immunogenic nature of the modified dendrimers, even at doses 50 times higher than those that protect against Ebola challenge (FIG. 12B) (Khan, et al. *Nano Lett*, doi:10.1021/nl5048972 (2015); Khan, et al. *Angewandte Chemie* 53, 14397-14401, doi:10.1002/anie.201408221 (2014)) is a property that favors efficient transgene expression, as any stimulation of innate immunity is due to the expression of the mRNA payload only. This method is compatible with large, self-amplifying RNA replicons and allows potent and persistent presentation of antigen to the immune system without stimulating IFN responses early upon injection. A strong IFN response would likely impede alphaviral replication and thus limit antigen dose over time. (Henriksen-Lacey, et al. *Mol Pharm.* 8, 153-161 (2011); Zhang, et al., *J Virol.*, 81, 11246-11255 (2007).

The choice of RNA vector, be it conventional or replicon, is a parameter critical to determining the intensity and persistence of antigen expression. Replicons based on RNA viruses of the alphavirus family including SFV, EEV, VEE and SIN, have served as vaccine vectors due to their relatively small size, case of genetic manipulation, and ability to replicate autonomously in host cell cytoplasm in the absence of all structural genes.

When delivered as replication-deficient pseudoviral particles, these vectors require complementation of structural genes in cell culture systems. (Ying, et al., *Nat Med* 5, 823-827 (1999)). Cationic liposomes can serve as a synthetic delivery method for a chimeric SIN/VEEV replicon vaccine in vivo, (Geall, et al., *Proc Natl Acad Sci USA* 109, 14604-14609 (2012); Bogers, et al. *J Infect Dis*, doi:jiu522 [pii] 10.1093/infdis/jiu522 (2014)) although protection against lethal pathogen challenges has yet to be reported. Rapid delivery of the replicon limits innate immune activation. Replication presumably proceeds robustly until the single-cycle restricted intracellular production of antigen triggers an immune response adequate to clear the replicon. (Liljestrom & Garoff, *Biotechnology* (N Y) 9, 1356-1361 (1991).

The fully synthetic nature of the MDNP delivery system is a key advantage. It requires no steps that depend on live cells for production, and in principle allows rapid screening of many individual vaccine candidates. Doses safe and effective in mice (up to at least 40 μg) are an order of magnitude greater than those needed to achieve significant protective immunity (FIGS. 13A-13B).

It should be possible to multiplex antigen composition so that several individual antigens could be formulated to yield a broadly multivalent vaccine. Ease of purification and scalability as well as avoiding the need for a cold chain favor further development of the synthetic nanoparticle-based platform.

Example 7. Modified Dendrimer Nanoparticle-Delivered VEE Replicon RNAs Protect Mice from Lethal *Toxoplasma Gondii* Challenge Materials and Methods The wild-type PRU-delta HXGPRT strain of *T. gondii* parasites, a gift from the Jeroen J.P. Sacij Lab, was prepared as previously described. Mice were inoculated with tachyzoites. Animals were monitored for clinical signs of sickness, including weight loss, poor grooming, lethargy, squinting, dehydration and drops in body temperature. Mice were euthanized if they experienced over 10% weight loss, severe dehydration, severe lethargy and/or significant drops in body temperature.

Results

Figure 14A:
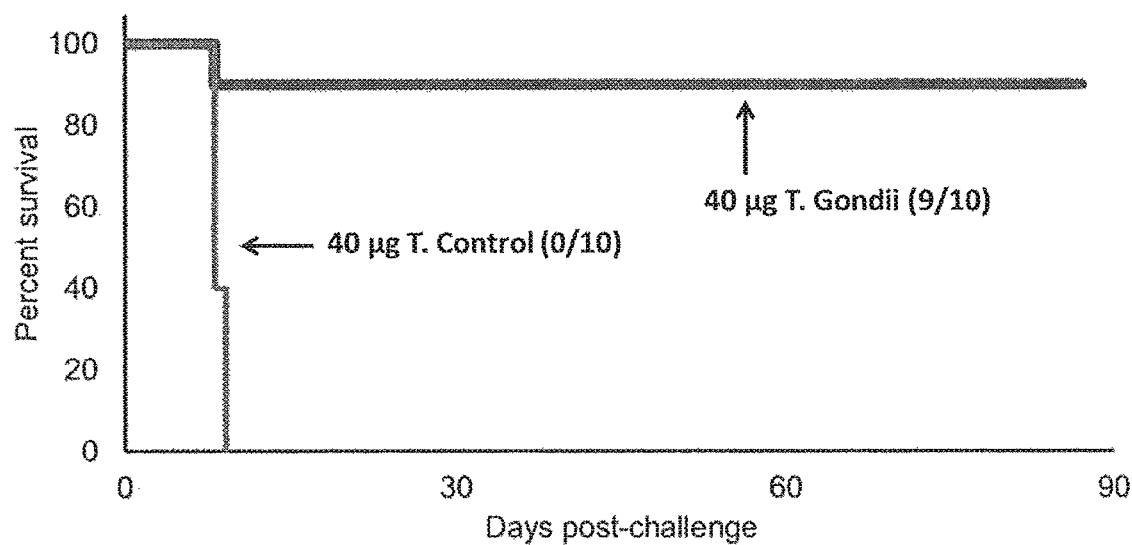
FIG. 14A is a line graph showing % survival over time post *T. gondii* infection (Days) for vaccinated (-) and unvaccinated (Control) mice, respectively.
Figure 14B:
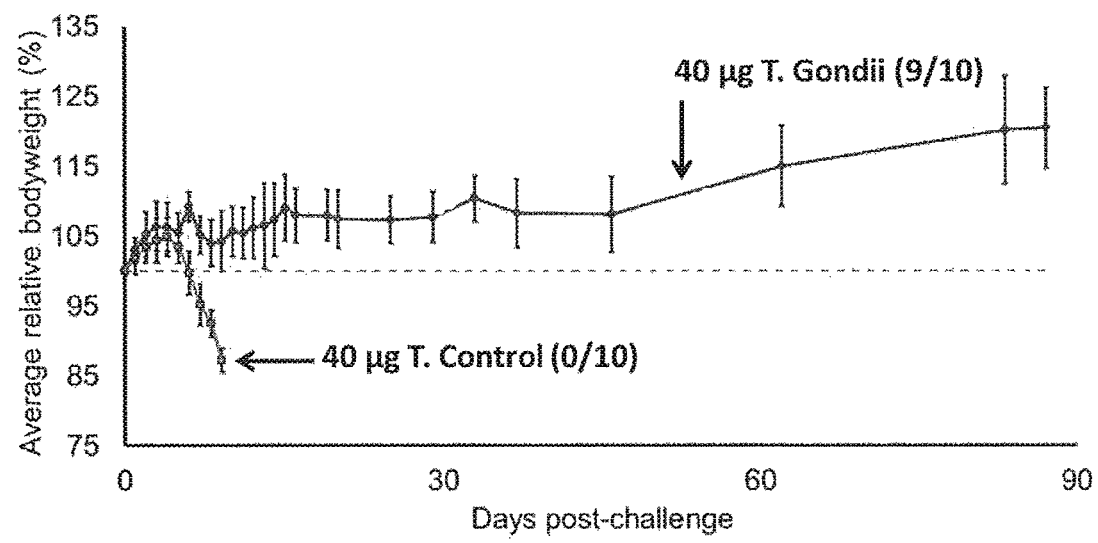
FIG. 14B is a line graph showing average relative bodyweight (%) over time post *T. gondii* infection (Days) for vaccinated (●) and unvaccinated (□; Control) mice, respectively.
Figure 14C:
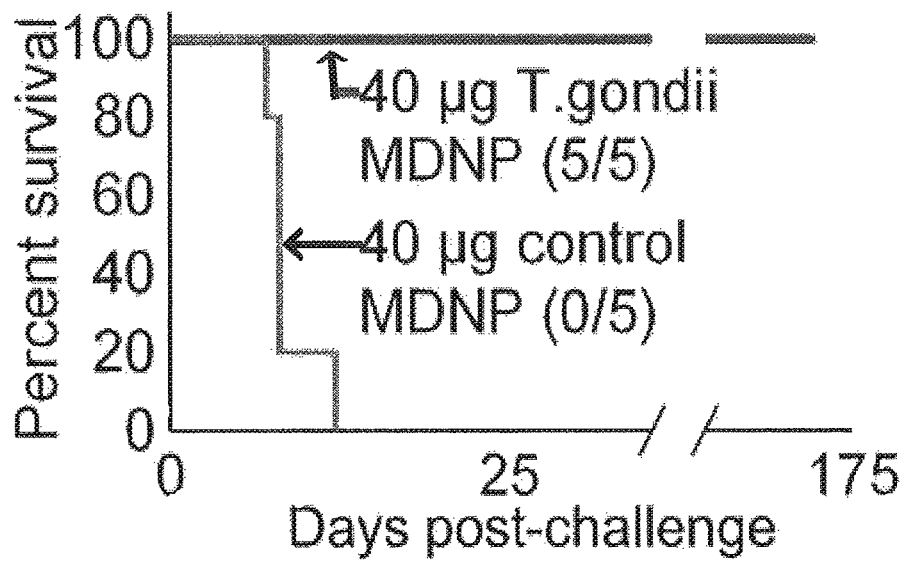
FIG. 14C is a line graph showing % survival over days post challenge with *T. gondii* (0-175 Days) for vaccinated (*T. gondii*) and unvaccinated (T. Control) mice, respectively.
Figure 14D:
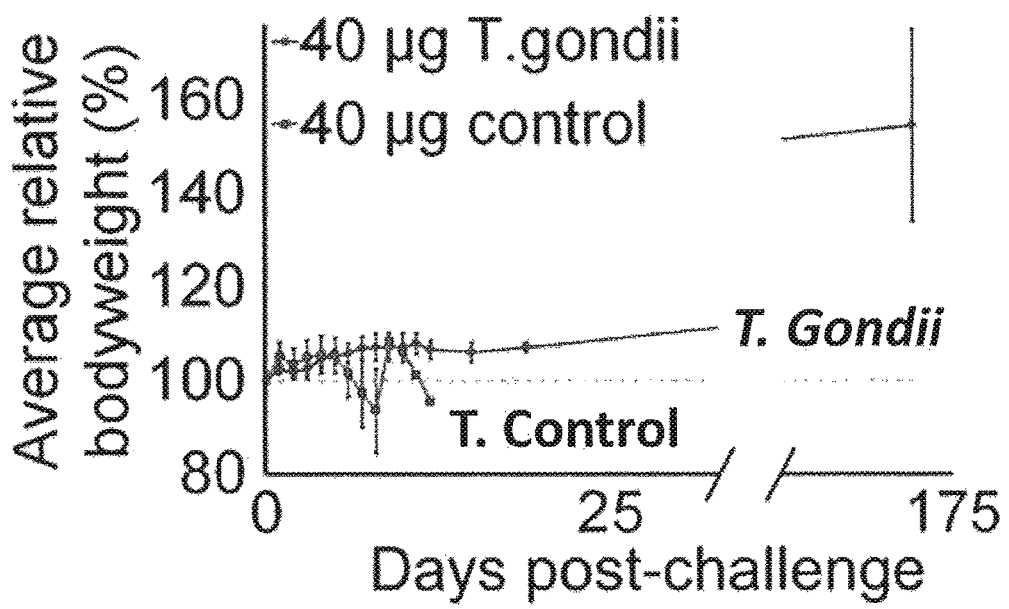
FIG. 14D is a line graph showing average relative bodyweight (%) over time post *T. gondii* infection (0-175 Days) for vaccinated (●) and unvaccinated (□; T. Control) mice, respectively.

As a demonstration of the MDNP's large payload capacity, a hexaplex vaccine was produced for *T. gondii*. *T. gondii* is an apicomplexan protozoan that infects one-third of world's population through contaminated food, can cause cerebral toxoplasmosis in immunocompromised individuals and has no approved, human vaccine, despite efforts to generate immunity though injection of live/attenuated parasites, DNA and peptides (Zhang, et al., *Expert Review of Vaccines*, 12(11): 1287-1299(2013)). The annual cost of this illness in the United States is estimated to be $3 billion (Hoffmann, et al., *Journal of Food Protection*, 75(7): 1292-1302(2012)). After confirming the ability to simultaneously express multiple replicons co-formulated into a single MDNP, a multiplexed *T. gondii* MDNP vaccine was produced. Six *T. gondii*-specific antigens, GRA6; ROP2A, ROP18, SAG1, SAG2A and AMA1, were encoded into VEEV replicons and equimolar amounts were co-formulated into MDNPs. These antigens were selected because they represent proteins expressed in multiple lifecycle stages of the parasite and are conserved across multiple strains and types. Animals were vaccinated with a single 40 μg dose of vaccine (6.67 ug per replicon, which is within the effective dose range established for Ebola in FIGS. 12A and 12B). As a control, animals were treated with a matching dose of MDNPs carrying VEEV HA as an irrelevant antigen. 32 days post-immunization, animals were challenged with lethal doses of the *T. gondii* type II strain PRU (FIGS. 14A-14B). By day 12, all control animals succumbed to infection. The remaining animals vaccinated with the hexaplex MDNP vaccine survived for over six months with no clinical indications. In a similar long-term experiment to test for single-dose efficacy, 100% protection was observed when mice were challenged 32 days after receiving one 40 μg *T. gondii* vaccine (FIG. 14C,14D). This is the first demonstration of a fully protective, single-dose mRNA replicon nanoparticle vaccine for *T. gondii*.

Example 8. Modified Dendrimer Nanoparticle-Delivered VEEV Replicon RNAs Elicit Humoral and Cellular Adaptive Immune Response Against Zika Virus Materials and Methods Antigenic components of a different pathogen, the Zika virus, were selected as another antigen to generate immunity against Zika virus peptides. Vaccine candidates were compared for their ability to elicit humoral and cellular adaptive immune responses against Zika virus in mice.

The MDNP formulation against Zaire Ebola virus (see Example 6, above) was used as a negative control vaccine.

Results

Figure 15A:
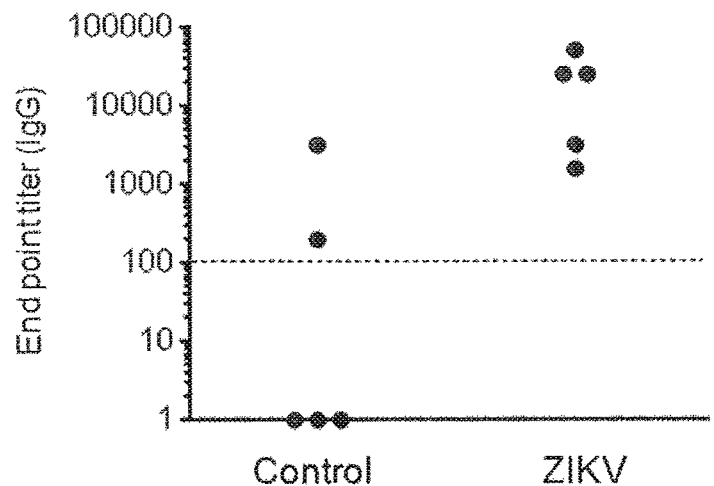
FIG. 15A is a graph showing (IgG) antibody Endpoint titer for each of two MDNP vaccines, control (NP formulation against Zaire Ebola virus); and ZIKV (NP formulation against Zika virus), respectively.
Figure 15B:
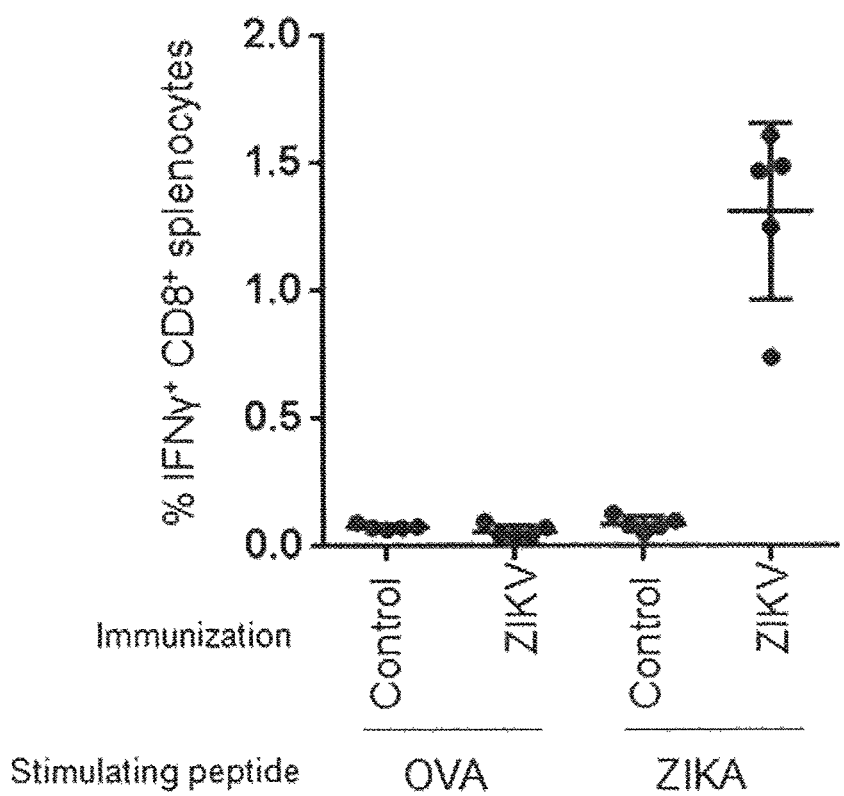
FIG. 15B is a graph showing percent IFNγ CD8+ splenocytes following immunization for each of two MDNP vaccines, control (NP formulation against Zaire Ebola virus); and ZIKV (NP formulation against Zika virus), independently, upon stimulation with either the OVA (Control) peptide, or ZIKA (Zika virus-derived peptide), respectively.

Humoral (FIG. 15A) and cellular (FIG. 15B) adaptive immune responses were raised against Zika virus in 100% of NP vaccinated mice, as compared with mice vaccinated with a control vaccine (NP formulation against Zaire Ebola virus).

SUMMARY

Figure 10A:
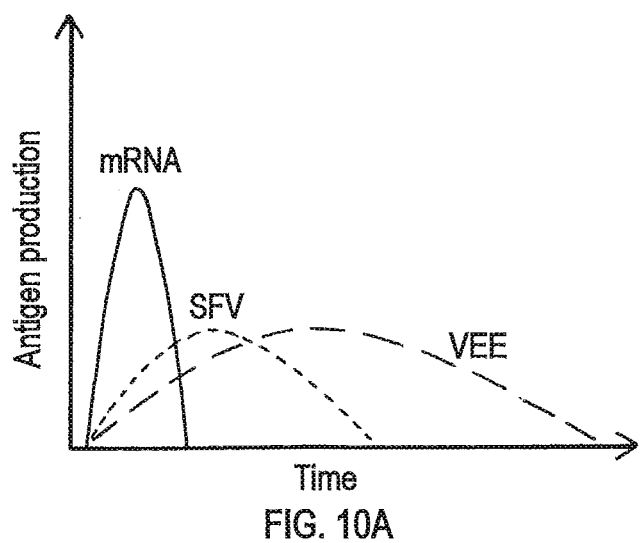
FIG. 10A is a cartoon representation of the time course for expression, showing antigen production over Time from Nanoecapsulated mRNA, SFV and VEE, respectively.
Figures 10B, 11A:
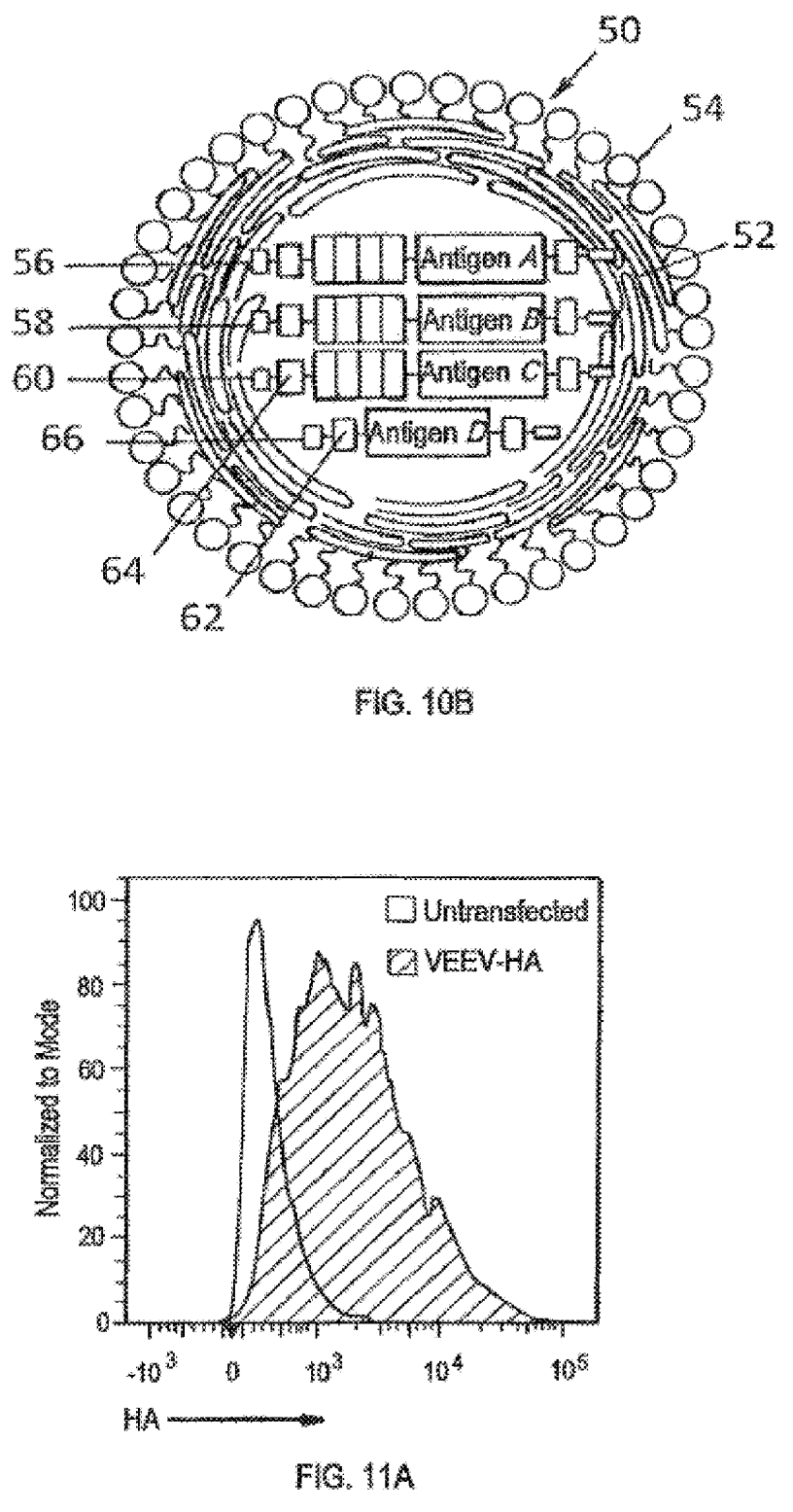

Gene-based approaches to vaccines have a number of potential advantages over conventional methods, as they are fully synthetic, rapidly customizable, and can be produced in adjuvant-free preparations (Srivastava, et al., *Annals of internal medicine,* 138 (7): 550-559 (2003)). Current virus-based vaccine production methods are time consuming; they require over 5 months of lead time, and output can be complicated by scale-up and yield issues, as experienced in the 2009 H1N1 pandemic (Partridge, et al., *Vaccine* 28 (30): 4709-4712 (2010)). Vaccines based on gene delivery by viral vectors such as adenovirus, rVSV, AAV, or CMV face the additional challenge of pre-existing or induced anti-vector immunity, which precludes repeated administration. The MDNP platform can better respond to sudden outbreaks, evolving pathogens, and individual patient needs due to its flexibility, safety and efficiency. With this platform, the timeline of production from initial access to the relevant DNA sequences to milligram-scale, injection-ready MDNP vaccine is only 7 days. By facilitating replicon delivery to the cytosol, the MDNPs drive endogenous antigen production that stimulates both T cell and antibody responses. Furthermore, because nano-encapsulation is RNA sequence independent, a variety of different replicons, each encoding a unique antigen, can be created and co-encapsulated (FIGS. 10A, 10B). The attainable doses (up to at least 40 µg) are an order of magnitude greater than those needed to achieve significant protective immunity (FIGS. 12A, 12B, 13A, 13B, 14A, 14B, 15A, 15B). Assuming this range of therapeutic index translates to humans, there is the potential to incorporate multiple, distinct antigens into a single formulation.

As a vector for immunization, mRNA has been investigated with varying degrees of success, particularly in the field of cancer immunotherapy (Van Lint, et al. *Expert Review of Vaccines,* 14(2): 235-251(2015)). Several factors complicate and limit the efficacy of mRNA-based therapeutics: (1) RNA molecules are susceptible to intracellular and extracellular degradation; (2) mRNA expression is transient; and (3) translational repression can occur in response to RNA (Baum A & Garcia-Sastre A (2010) Induction of type I interferon by RNA viruses: cellular receptors and their substrates (Baum & Garcia-Sastre, *Amino Acids,* 38(5): 1283-1299(2010); Heil, et al. *Science* 303(5663): 1526-1529 (2004); Kariko, et al., *The Journal of biological chemistry* 279(13): 12542-12550(2004); Pichlmair, et al. *Science* 314 (5801): 997-1001(2006); Levin et al., Journal of biological chemistry 256(14): 7638-7641(1981). Nevertheless, administration of naked antigen-encoding mRNA can confer anti-tumor immunity when injected directly into lymph nodes (Kreiter, et al. *Cancer Res,* 70(22): 9031-9040(2010); Van Lint, et al., *Cancer Res.,* 72(7): 1661-1671(2012)). Immunogenicity and/or toxicity of delivery compounds that could be used to deploy the vaccine by more amenable routes poses an additional complication. Cationic lipids, efficacious in some applications (Geall, et al., *Proc Natl Acad Sci USA* 109(36): 14604-14609(2012); Bogers, et al. *The Journal of infectious diseases*(2014)), can be toxic when used at higher doses and if incompletely complexed (Hofland, et al., *Proc Natl Acad Sci USA* 93(14): 7305-7309(1996); Cullis, et al., *Advanced drug delivery reviews* 32(1-2): 3-17(1998); Lv, et al., *J. Control. Release,* 114(1): 100-109(2006)). Furthermore, cationic lipids can be immunogenic, which can limit transgene expression and raise safety concerns (Henriksen-Lacey M, et al., *Mol Pharm* 8(1): 153-161(2011)). IFN production in response to lipid-complexed mRNA can limit efficacy of mRNA-based vaccines (Pollard C, et al., *Molecular therapy: the journal of the American Society of Gene Therapy,* 21(1): 251-259(2013)). Various nanoparticle formats have demonstrated varying levels of efficacy through intradermal (Hoerr, et al., *Eur J Immunol* 30(1): 1-7(2000)), intrasplenic (Zhou, et al., *Human gene therapy* 10(16): 2719-2724(1999)), subcutaneous (Pollard C, et al. *Molecular therapy: the journal of the American Society of Gene Therapy* 21(1): 251-259. (2013)), intravenous (Hoerr, et al., *Eur J Immunol* 30(1): 1-7(2000), Mockcy, et al., *Cancer Gene Ther* 14(9): 802-814(2007)), and even intranasal (Phua, et al., *Sci Rep* 4: 5128(2014)) routes of administration. Successful applications of RNA nanoparticle-based vaccines that are independent of ex vivo transfection of antigen presenting cells are limited in animal models (reviewed in (Ulmer, et al., *Vaccine* 30(30): 4414-4418(2012); and (Weiner, *Molecular therapy: the journal of the American Society of Gene Therapy* 21(3): 506-508(2013))), and few such approaches have made it to clinical trials. While correlates of immune protection in humans have been reported, clinical efficacy has been disappointing (Weide, et al., *J Immunother* 31(2): 180-188(2008); Weide, et al., *J Immunother,* 32(5): 498-507(2009). Rittig, et al. *Molecular therapy: the journal of the American Society of Gene Therapy* 19(5): 990-999(2011); Kreiter, et al., *Curr Opin Immunol,* 23(3): 399-406(2011)). Replicons based on RNA viruses of the alphavirus family such as SFV, VEEV, and SIN have served as vaccine vectors, usually delivered as replication-deficient pseudoviral particles generated though complementation of structural genes in cell culture (Lundstrom, Viruses 7(5): 2321-2333(2015)).

Previously, PRINT protein particles were explored for the non-viral in vitro delivery of mRNA replicons (Xu, et al. *Molecular Pharmaceutics* 10(9): 3366-3374(2013)). However, only two non-viral in vivo delivery methods have been reported. These include a cationic nano-emulsion, comprised cationic lipid DOTAP emulsified with the constituents of the MF59 adjuvant (Brito, et al. *Molecular Therapy* 22(12): 2118-2129(2014); Bogers, et al. *Journal of Infectious Diseases* 211(6): 947-955(2015).), and a DLinDMA-centric lipid nanoparticle (Hekele A, et al. *Emerging Microbes and Infections* 2(2013); Geall, et al., *Proc Natl Acad Sci USA* 109(36): 14604-14609(2012)), both of which are 5-component systems. While these have been used as a synthetic delivery method for a chimeric SIN/VEEV replicon vaccine in vivo, they have yet to show protection against lethal pathogen challenges (Hekele A, et al. *Emerging Microbes and Infections* 2(2013); Gcall, et al., *Proc Natl Acad Sci USA* 109(36): 14604-14609(2012)). In contrast, the MDNP approach, a fully synthetic 3-component system that utilizes ionizable delivery materials, lipid-anchored PEG and replicons, confers protection in mouse models of lethal virus and protozoan infection. This is the first fully synthetic RNA-based replicon system capable of generating protective immunity against a broad variety of pathogens in lethal challenge models. This work also demonstrates that the choice of RNA payload, be it conventional mRNA or replicon, can significantly affect the intensity and persistence of antigen expression (FIGS. 2F-2G, FIGS. 8a-8b).

The MDNP delivery technology does not generate a systemic increase in inflammatory cytokine production, including IFN, when using doses 500 times higher than those required for Ebola and *T. gondii* protection (Khan O F, et al., *Angewandte Chemie* 53(52): 14397-14401(2014); Khan O F, et al. *Nano Lett* 15(5): 3008-3016(2015)). This is helpful because a strong, early IFN response may impede alphaviral replication and thus limit the dose of antigen over time (White et al., *J Virol* 75(8): 3706-3718(2001); Zhang, et al., *J Virol* 81(20): 11246-11255(2007)). Furthermore, complete protection in both disease models and prolonged antigen-specific T cell responses (at least 10 days post vaccination) were achieved in the absence of adjuvants, which are commonly used to increase the inflammatory response (Schijns et al., *Expert Rev Vaccines* 10(4): 539-550(2011)).

The lack of a systemic cytokine response to the nanoparticle delivery vehicles may also prevent anti-vector immunity (Ulmer, et al., *Vaccine* 30(30): 4414-4418(2012)). Anti-vector immunity occurs when the immune system responds to and inactivates the delivery vehicle, which has been observed in, for example, virus-mediated delivery platforms (Small, et al., *Current Opinion in Virology* 1(4): 241-245 (2011); Lopez-Gordo E, et al., *Human gene therapy* 25(4): 285-300(2014);). This property may also obviate the need for homologous boosting, which has been suggested to be necessary for rVSV-based systems during recent human trials (Fuchs, et al. *Open Forum Infectious Diseases* 2(3) (2015)). This may enable repeated dosing of patients for a variety of diseases using the same delivery technology.

To better respond to evolving pathogens, sudden outbreaks and individual patient needs, a flexible, safe and efficient vaccine platform amenable to rapid production near the point of care is required. The platform developed here addresses this need by providing a synthetic system that can allow for: 1) very rapid production following target identification; 2) require minimal post-production purification; 3) have low potential for contaminating allergens; 4) allow for relatively large payloads, to allow for encapsulation of multiple antigen-producing RNAs, including replicons; 5) not require the use of additional adjuvants which can induce unfavorable immune responses and diminish endogenous mRNA production and reduce replicon self-amplification (Gupta, et al., *Vaccine* 11(3): 293-306(1993); Pollard C, et al. *Molecular therapy: the journal of the American Society of Gene Therapy* 21(1): 251-259(2013). White et al., *J Virol* 75(8): 3706-3718(2001); Zhang, et al., *J Virol* 81(20): 11246-11255(2007)); 6) induce appropriate antibody production and CD8+ T cell responses; and finally 7) generate protective immunity with a single dose to improve patient compliance and reduce healthcare worker burden.

Example 9. Modified Dendrimer Nanoparticle-Delivered Replicon RNAs Prophylactically Vaccinate Against Development of Non-Small Cell Lung Cancer To demonstrate this vaccination modality could be used for the creation of a prophylactic cancer vaccine, a replicon using the putative NSCLC-associated oncofetal antigen Hmga2 was synthesized.

Materials and Methods

Nanoparticle vaccines were creating using replicons encoding Hmga2, and mice were immunized with MDNPs encoding Hmga2. Two weeks post immunization, Hmga2+ or Hmga2-KP tumor cells were orthotopically transplanted into mouse lungs via intra-tracheal injections. N=5.

Results

Using an established model of lung adenocarcinoma, involving lung specific mutation of the Kras oncogene and the p53 tumor suppressor gene (the "KP" model of lung cancer), which utilizes viral administration of Cre recombinase to activate a latent oncogenic allele of Kras and to delete the tumor suppressor p53, the progression of non-small cell lung cancer can be examined (DuPage, et al., *Nat Protoc.;* 4(7): 1064-1072(2009)). Among other applications, the KP model has been used to follow the progressive loss of markers of differentiation in lung tumor cells over time as well as the subsequent up-regulation of protein whose expression is normally associated with embryogenesis, such as Hmga2. (Winslow, et al., *Nature,* 473 (7345), 101-104 (2011)).

Figure 16A:
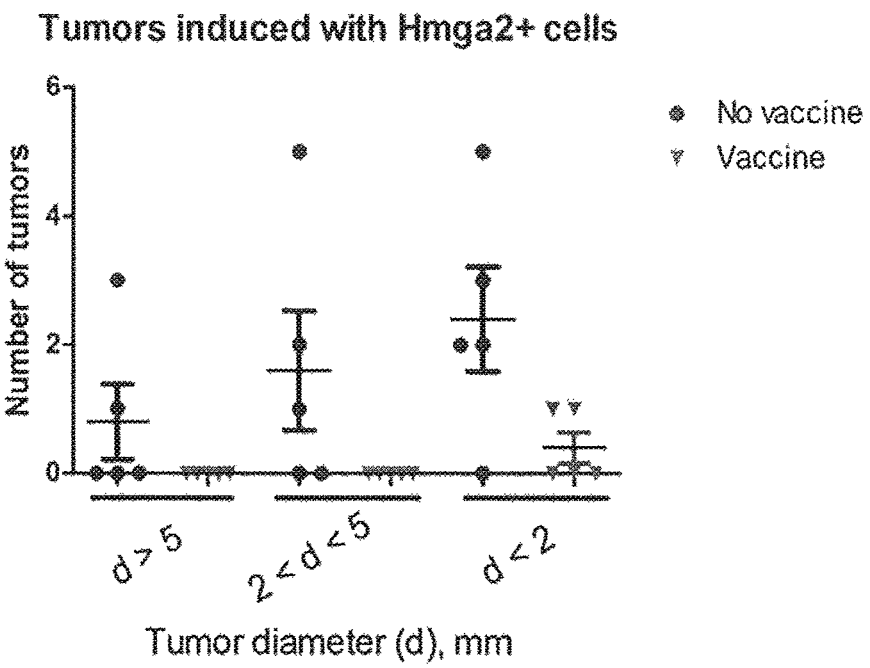
FIGS. 16A and 16B are graphs showing the number of tumors (0-6) over tumor diameter (mm) for each of d>5, 2<d<5 and d<2 groups, with (▼) and without (●) vaccine, respectively, induced with Hmga2+ cells (FIG. 16A) and Hmga2− cells (FIG. 16B).
Figure 16B:
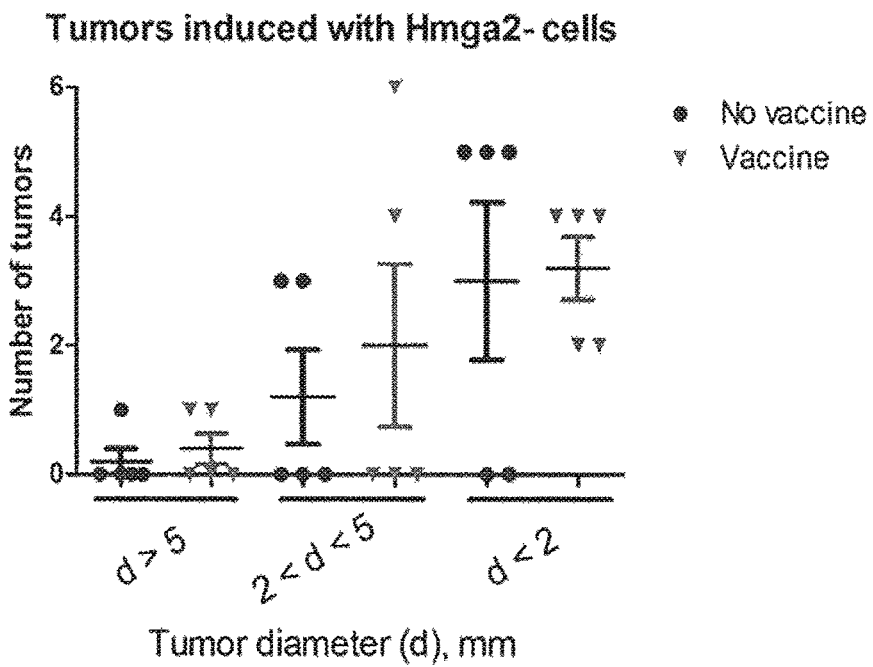

In a pilot study utilizing transplanted mouse tumor-derived cell lines, prophylactic vaccination of recipient mice suppressed the development of large and medium-sized tumors, while also patently decreasing the number of small tumors. Tumors induced with Hmga2+ KP tumor cells showed a reduction in the number and size of tumors (FIG. 16A), as compared to Hmga2− tumors (FIG. 16B), indicating antigen-specific effect. Importantly, this protective effect was dependent on antigen expression in the transplanted cells, an indication of specificity.

We claim:

1. A method for delivering a therapeutic, prophylactic and/or diagnostic agent to a subject, comprising administering to the subject a modified dendrimer nanoparticle comprising
   (i) one or more dendrimers selected from the group consisting of one to seven generation poly(ethylene imine) dendrimers and two to seven generation poly (propylene imine) dendrimers;
   (ii) one or more amphiphilic polymers, wherein the amphiphilic polymer is 1,2-dimystistoyl-sn-glycerol-3-phosphoethanolamine-N-[methoxy (polyethylene glycol)-2000]
   wherein the amphiphilic polymer is not a dendrimer; and
   (iii) one or more nucleic acids that express or encode one or more therapeutic, prophylactic and/or diagnostic agents;
   wherein the nucleic acids are encapsulated in the dendrimer nanoparticle wherein the nanoparticle does not include cholesterol.

2. The method of claim 1, wherein the nanoparticle delivers one or more replicating RNAs, and wherein the replicating RNAs express one or more proteins in the cells of a subject.

3. The method of claim 2, wherein the one or more replicating RNAs express two or more proteins in the cells of the subject, and wherein the replicating RNAs express the proteins at different rates.

4. The method of claim 1, wherein the one or more dendrimers is poly(ethyleneimine).

5. The method of claim 4, wherein the one or more dendrimers is polypropylene imine.

6. The method of claim 1, wherein the one or more dendrimers is modified by the addition of epoxide-terminated alkyl chains, in a size between 1 and 30 carbons, inclusive.

7. The method of claim 1, wherein the amphiphilic polymer comprises a hydrophilic component selected from the group consisting of polyalkylene oxides and block copolymers thereof.

8. The method of claim 1, wherein the amphiphilic polymer comprises a hydrophobic component selected from the group consisting of a lipid and a phospholipid.

9. The method of claim 7, wherein the mass ratio of dendrimer to hydrophilic component of the amphiphilic polymer is between 20:1 and 5:1.

10. The method of claim 1, wherein the nanoparticle further comprises a therapeutic, prophylactic, and/or diagnostic agent selected from the group consisting of proteins, peptides, carbohydrates, nucleic acids, lipids, drugs, and combinations thereof.

11. The method of claim 10, wherein the nucleic acids are selected from the group consisting of complementary DNA (cDNA), replicating RNA (repRNA), messenger RNA (mRNA), small interfering RNA (siRNA), transfer RNA (tRNA), guide-strand RNA (sgRNA), microRNA (miRNA), double-stranded RNA (dsRNA) that is at least 24 nucleotides in length, and combinations thereof.

12. The method of claim 11, wherein the nucleic acids comprise one or more ribonucleic acid sequences of between approximately 10 and 20,000 bases in length, inclusive.

13. The method of claim 12, wherein the mass ratio of dendrimer to ribonucleic acid is between 10:1 and 1.5:1 inclusive.

14. The method of claim 12, wherein the replicating RNA comprises a modified alphavirus replicon RNA.

15. The method of claim 1, wherein the nanoparticle comprises two or more replicating RNAs, wherein the replicating RNAs independently encode one or more antigens from an infectious agent, parasite, or abnormal proliferation disorder such as cancer.

16. The method of claim 11, wherein the nanoparticle comprises one or more replicating RNAs and one or more messenger RNAs, and wherein the messenger RNA is modified to include the 5' and 3' untranslated regions of the replicating RNA.

17. The method of claim 1, wherein the size of the nanoparticle is between 30 nm and 450 nm, inclusive.

18. The method of claim 6, wherein the epoxide-terminated alkyl chains are between 6 and 16 carbons, inclusive.

19. The method of claim 9, wherein the mass ratio of the one or more dendrimers to hydrophilic component of the amphiphilic polymer is 11.5:1.

20. The method of claim 12, wherein the ribonucleic acid sequences are between approximately 9,000 and 15,000 bases in length, inclusive.

21. The method of claim 13, wherein the mass ratio of the one or more dendrimers to ribonucleic acid is 5:1.

22. The method of claim 17, wherein the size of the nanoparticle is between 60 nm and 250 nm in diameter, inclusive.

23. The method of claim 1, wherein alkylated dendrimer consists of poly(ethyleneimine), and wherein the nucleic acid consists of replicating RNA.

* * * * *